US011102995B2

(12) United States Patent
Browne et al.

(10) Patent No.: US 11,102,995 B2
(45) Date of Patent: Aug. 31, 2021

(54) COMPOSITIONS AND METHODS FOR IMPROVING TASTE OF NON-NUTRITIVE SWEETENERS

(71) Applicant: PEPSICO, INC., Purchase, NY (US)

(72) Inventors: Damian Browne, Old Greenwich, CT (US); Winsome Johnson, Ossining, NY (US)

(73) Assignee: PEPSICO, INC., Purchase, NY (US)

( * ) Notice: Subject to any disclaimer, the term of this patent is extended or adjusted under 35 U.S.C. 154(b) by 92 days.

(21) Appl. No.: 16/330,725

(22) PCT Filed: Sep. 14, 2017

(86) PCT No.: PCT/US2017/051570
§ 371 (c)(1),
(2) Date: Mar. 5, 2019

(87) PCT Pub. No.: WO2018/053135
PCT Pub. Date: Mar. 22, 2018

(65) Prior Publication Data
US 2019/0208803 A1    Jul. 11, 2019

Related U.S. Application Data

(60) Provisional application No. 62/395,476, filed on Sep. 16, 2016.

(51) Int. Cl.
| | |
|---|---|
| *A23L 2/60* | (2006.01) |
| *A23L 27/20* | (2016.01) |
| *A23L 27/30* | (2016.01) |
| *A23L 27/00* | (2016.01) |
| *A23L 2/385* | (2006.01) |
| *A23G 3/00* | (2006.01) |
| *C07H 15/256* | (2006.01) |

(52) U.S. Cl.
CPC .............. *A23L 2/60* (2013.01); *A23G 3/00* (2013.01); *A23L 2/385* (2013.01); *A23L 27/204* (2016.08); *A23L 27/2026* (2016.08); *A23L 27/2028* (2016.08); *A23L 27/2052* (2016.08); *A23L 27/2056* (2016.08); *A23L 27/30* (2016.08); *A23L 27/36* (2016.08); *A23L 27/84* (2016.08); *A23L 27/86* (2016.08); *C07H 15/256* (2013.01); *A23V 2002/00* (2013.01); *A23V 2200/15* (2013.01); *A23V 2250/258* (2013.01); *A23V 2250/262* (2013.01)

(58) Field of Classification Search
CPC ........ A23L 2/60; A23L 27/2056; A23L 27/86; A23L 27/30; A23L 27/2026; A23L 27/204; A23L 27/2028; A23L 27/84; A23L 27/2052; A23G 3/00; C07H 15/256; A23V 2002/00; A23V 2200/15; A23V 2250/258; A23V 2250/262
USPC .................. 426/548, 590, 534, 536
See application file for complete search history.

(56) References Cited

U.S. PATENT DOCUMENTS

| | | | |
|---|---|---|---|
| 3,988,344 A * | 10/1976 | Nakaoji ............... | C07D 275/06 548/211 |
| 4,082,858 A | 4/1978 | Morita et al. | |
| 4,361,697 A | 11/1982 | Dobberstein et al. | |
| 4,892,938 A | 1/1990 | Giovanetto | |
| 5,962,678 A | 10/1999 | Payzant et al. | |
| 5,972,120 A | 10/1999 | Kutowy et al. | |
| 7,052,725 B2 | 5/2006 | Chang et al. | |
| 7,838,044 B2 | 11/2010 | Abelyan et al. | |
| 7,862,845 B2 | 1/2011 | Magomet et al. | |
| 8,329,239 B2 | 12/2012 | Ungureanu et al. | |
| 9,107,436 B2 | 8/2015 | Prukayastha et al. | |
| 9,138,011 B2 * | 9/2015 | Putter ............... | A23L 27/84 |
| 9,259,027 B2 | 2/2016 | Hayes | |
| 9,408,406 B2 | 8/2016 | Dierbach et al. | |
| 2002/0168446 A1 * | 11/2002 | Zimlich, III ............. | C12G 3/07 426/11 |
| 2006/0188629 A1 | 8/2006 | Liesen et al. | |
| 2007/0059418 A1 | 3/2007 | Catani et al. | |
| 2007/0059420 A1 | 3/2007 | Catani | |
| 2007/0116828 A1 | 5/2007 | Prakash et al. | |
| 2008/0069939 A1 | 3/2008 | Catani et al. | |
| 2008/0107787 A1 | 5/2008 | Prakash et al. | |
| 2009/0155446 A1 * | 6/2009 | Reiss ............... | A23L 27/13 426/650 |
| 2010/0021600 A1 | 1/2010 | Yagi et al. | |
| 2011/0059218 A1 | 3/2011 | Corliss et al. | |
| 2012/0269947 A1 | 10/2012 | Osanai et al. | |
| 2013/0136836 A1 | 5/2013 | Putter et al. | |
| 2013/0136838 A1 | 5/2013 | San Miguel et al. | |
| 2013/0209658 A1 | 8/2013 | Spelman et al. | |
| 2013/0251874 A1 | 9/2013 | Muller et al. | |

(Continued)

FOREIGN PATENT DOCUMENTS

| | | |
|---|---|---|
| EP | 2193723 A1 | 6/2010 |
| RU | 2440011 C1 | 1/2012 |

(Continued)

OTHER PUBLICATIONS https://webbook.nist.gov/cgi/cbook.cgi?ID=C39212232, no date.*
International Search Report and Written Opinion for International Application No. PCT/US2017/051570, International Search Authority, United States, dated Dec. 5, 2017, 10 pages.

*Primary Examiner* — Leslie A Wong

(74) *Attorney, Agent, or Firm* — Sterne, Kessler, Goldstein & Fox

(57) ABSTRACT

The present disclosure provides a novel sweetener composition of improved taste of the sweetener (e.g., reduced bitterness and/or astringency, and improved overall sweet quality of the composition); food and beverage products containing the same; and methods of making the same.

30 Claims, 68 Drawing Sheets

(56) References Cited

U.S. PATENT DOCUMENTS

| | | |
|---|---|---|
| 2013/0280400 A1 | 10/2013 | Bartoshuk et al. |
| 2015/0030721 A1 | 1/2015 | Strydom et al. |
| 2015/0086695 A1 | 3/2015 | Oglesby |
| 2015/0189904 A1 | 7/2015 | Prakash et al. |
| 2015/0237901 A1 | 8/2015 | Chaturvedula et al. |
| 2015/0320101 A1 | 11/2015 | Walton et al. |
| 2015/0327584 A1 | 11/2015 | Shi et al. |
| 2015/0366251 A1 | 12/2015 | Fischer et al. |
| 2016/0128371 A1 | 5/2016 | Prukayastha et al. |
| 2016/0183578 A1 | 6/2016 | Wonschik et al. |
| 2016/0227826 A1 | 8/2016 | Zou |
| 2016/0235095 A1 | 8/2016 | Hilmer et al. |
| 2016/0255868 A1 | 9/2016 | Panarisi et al. |

FOREIGN PATENT DOCUMENTS

| | | |
|---|---|---|
| RU | 2592549 C2 | 7/2016 |
| WO | WO-0111988 A2 | 2/2001 |
| WO | WO-2007081442 A2 | 7/2007 |
| WO | WO-2008112983 A1 | 9/2008 |
| WO | WO-2008147726 A1 | 12/2008 |
| WO | WO-2009085758 A1 | 7/2009 |
| WO | WO-2013026151 A1 | 2/2013 |
| WO | WO-2013079187 A2 | 6/2013 |
| WO | WO-2014183041 A1 | 11/2014 |
| WO | WO-2015082012 A1 | 6/2015 |
| WO | WO-2016029153 A1 | 2/2016 |
| WO | WO-2016038603 A1 | 3/2016 |
| WO | WO-2016074761 A1 | 5/2016 |

\* cited by examiner

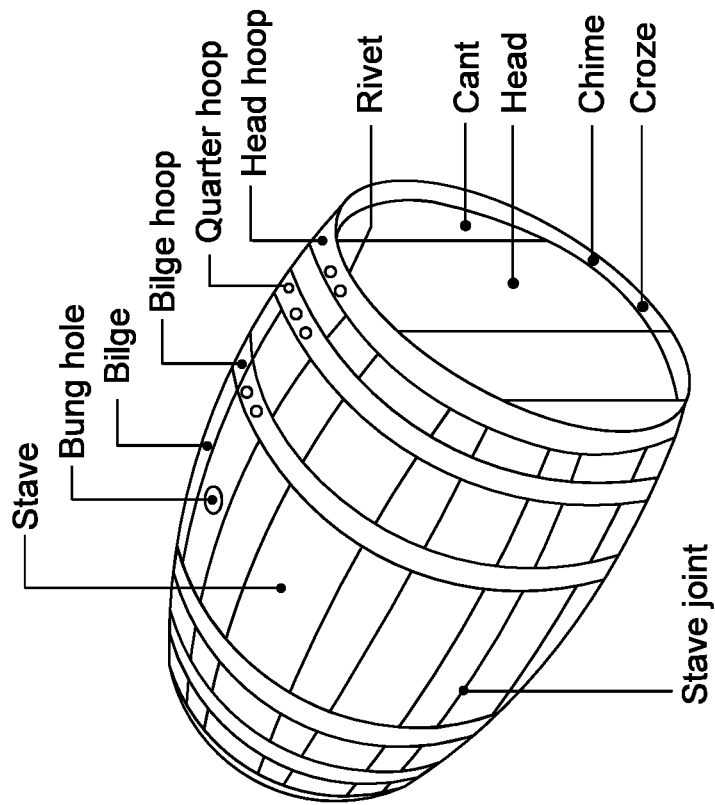
Figure 1
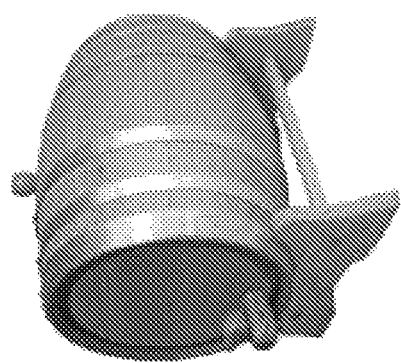

± Compound 4 (Sweet/Bitter blocker)

± Compound 7 (Aftertaste/Glucagon blocker)

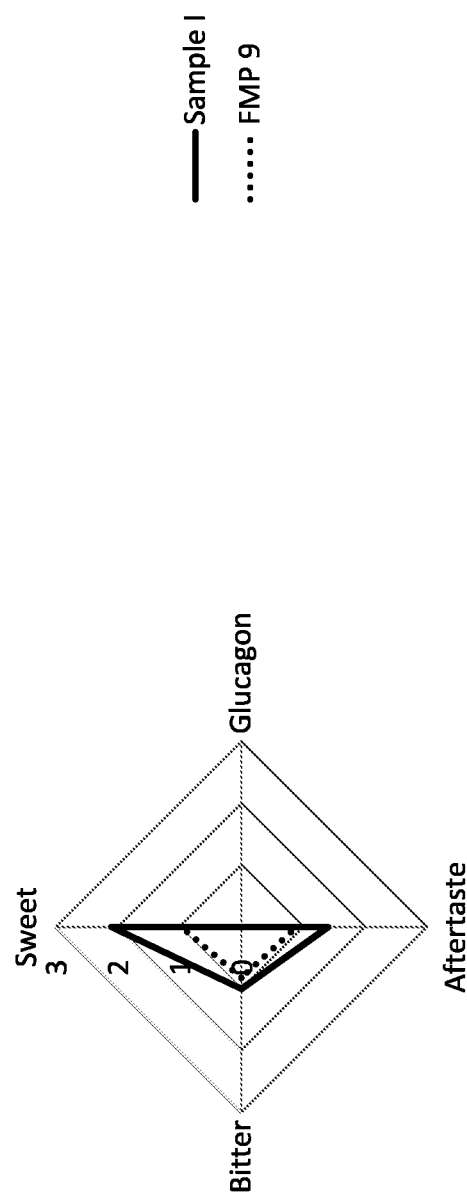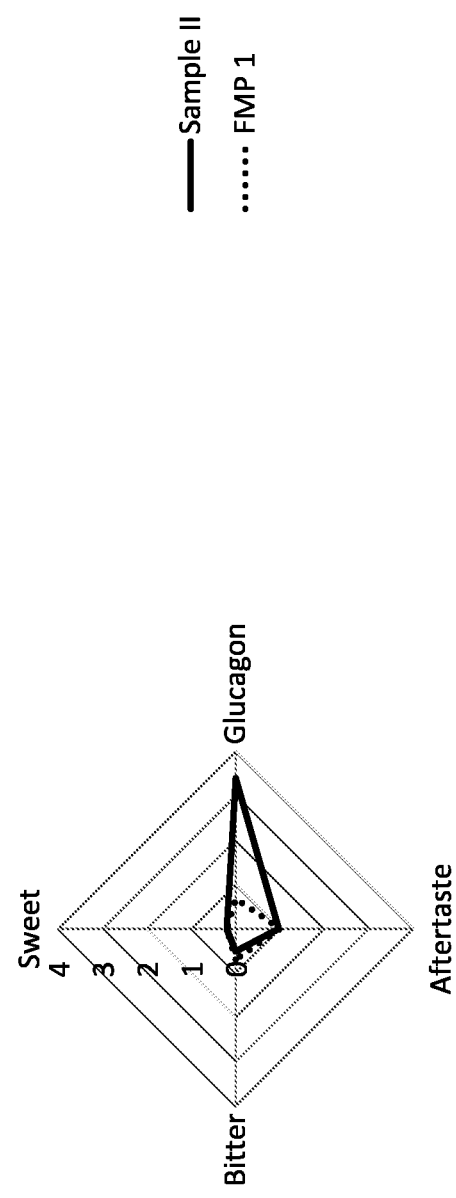
Figure 14A
Figure 14B

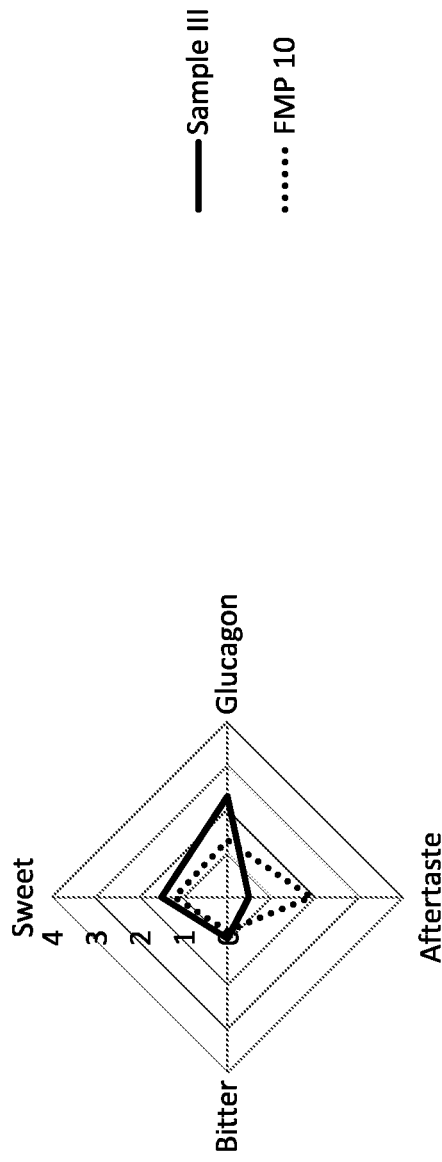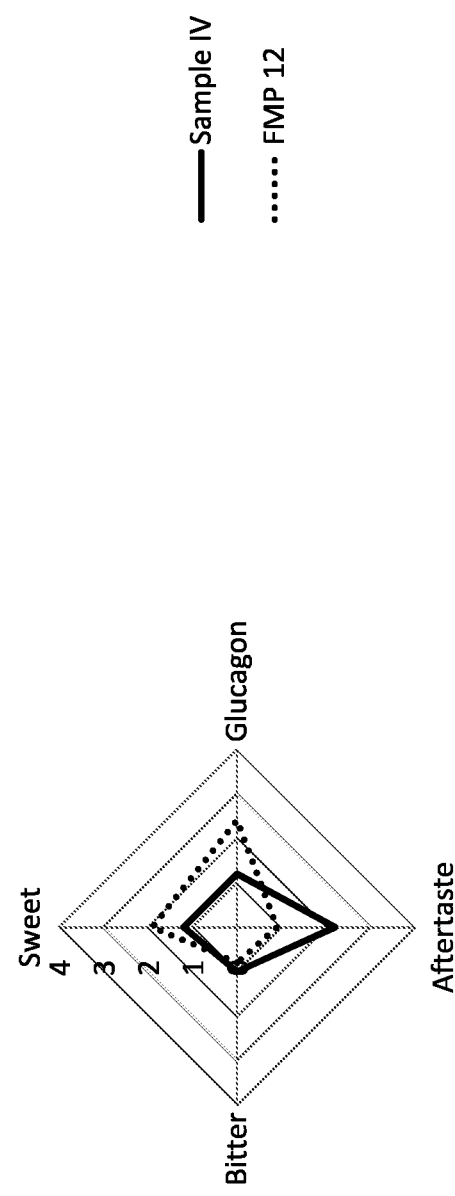
Figure 15A
Figure 15B

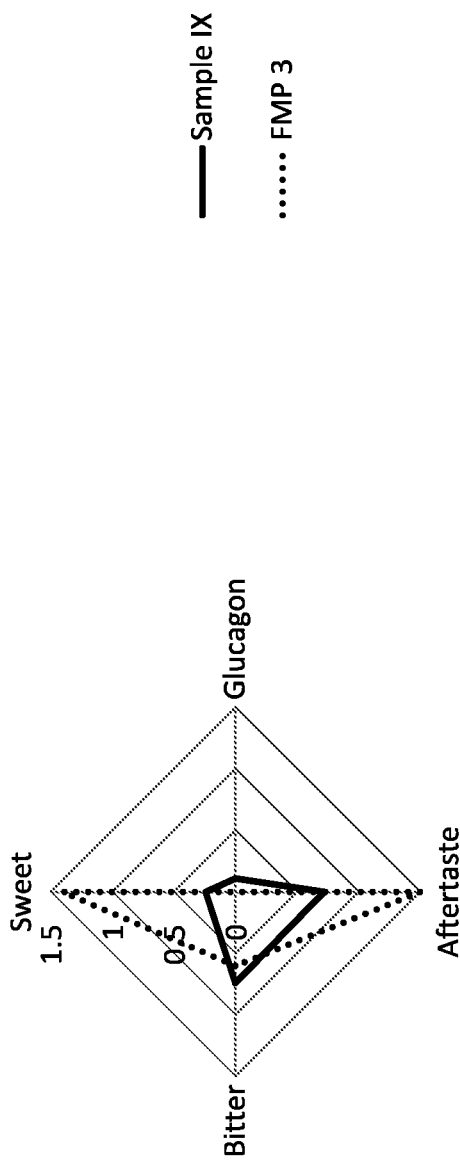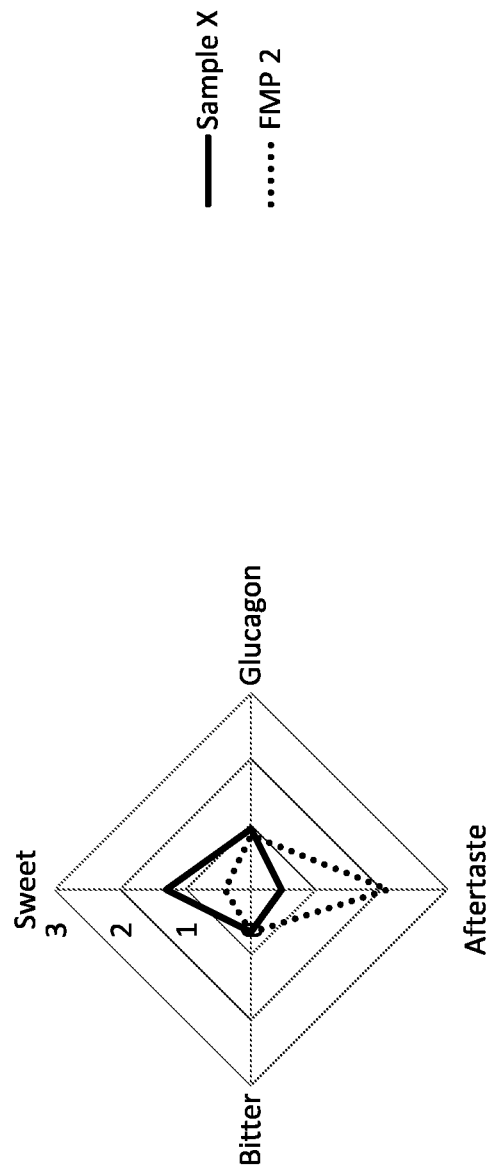

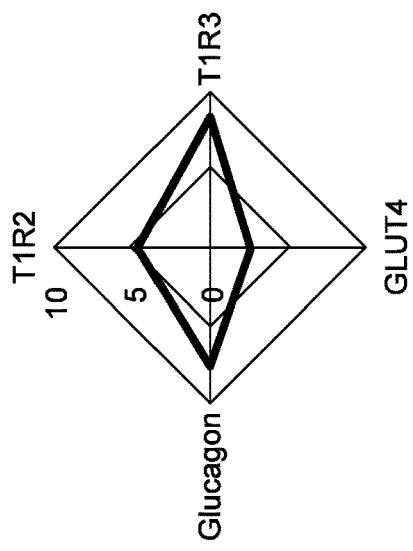
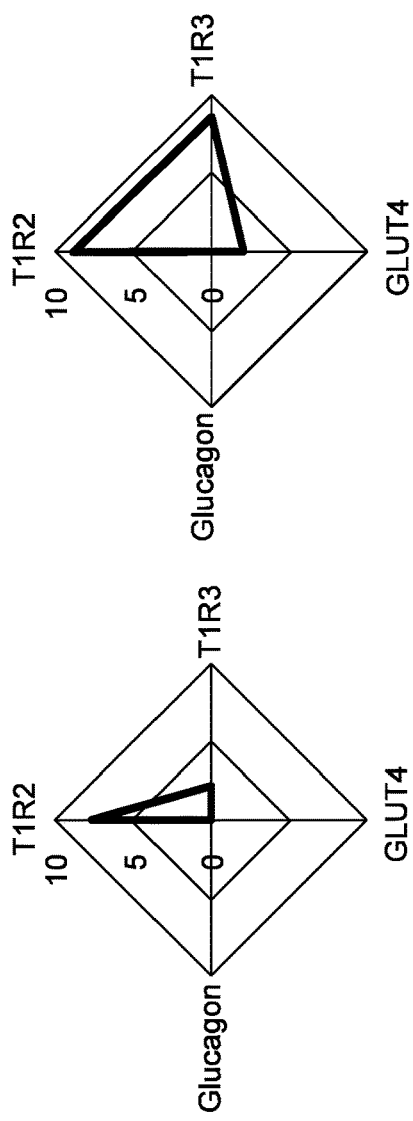
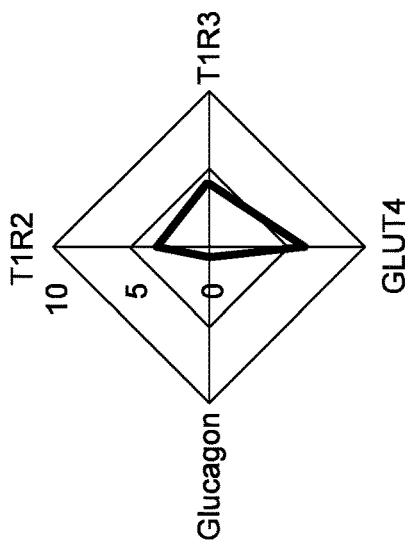
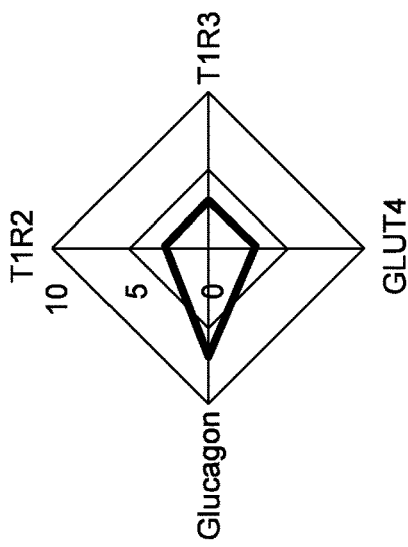
Figure 20

Figure 21

| Sample | Sweet T1R2/T1R3 | Glucagon | Aftertaste (GLUT4) | Bitter (25 T2R) | Comments |
|---|---|---|---|---|---|
| Base solution without Stevia | +/- | +/+ | +/- | +/- | |
| Base solution with 8% Stevia blend 3 | +/+ | +/- | +/+ | +/+ | |
| XI | +/+ | +/- | +/- | +/- | High sweet and low Bitterness |
| XII | +/+/+ | +/+/+ | +/+/+ | +/- | High Sweet and Aftertaste |
| XIII | +/+/+ | +/+/+ | -/- | +/+ | High Sweet and Bitterness |
| XIV | +/+ | +/+ | +/- | +/+ | High Sweet and Bitterness |
| XV | +/- | -/- | +/- | -/- | Low Sweet and no Bitterness |
| XVI | +/+ | +/+ | +/- | -/- | High sweet and no Bitterness |
| XVII | +/- | +/- | +/- | -/- | Low Sweet and no Bitterness |
| XVIII | +/+/+ | +/+ | +/+ | -/- | High Sweet and Aftertaste, and no Bitterness |
| XIX | +/+/+ | +/- | +/- | -/- | High Sweet and no Bitterness |
| XX | +/+ | -/- | +/+/+ | -/- | High Sweet and Aftertaste, and no Bitterness |
| XXI | -/- | +/+/+ | +/- | +/- | High Glucagon (sweet) and low Bitterness |

Comp'ds 2, 6 + 8% Stevia Blend 3

Comp'ds 6,10 + 8% Stevia Blend 3

Figure 35

Effect on Sweetness and Bitterness in mixture with Stevia 2000ppm

| Sample (Compounds and Stevia Blend) | Sweet T1R2/T1R3 | Glucagon | Aftertaste (GLUT4) | Bitter (25 T2R) | Comments |
|---|---|---|---|---|---|
| Base solution without Stevia | +/- | +/+ | +/- | +/- | |
| Base solution with 8% Stevia Blend 3 | +/+ | +/- | +/+ | +/+ | High Sweet, Aftertaste and Bitterness |
| Base solution with 0.2% Stevia Blend 3 | +/+ | +/- | +/+ | +/+/+ | High Sweet, Aftertaste and Bitterness |
| XXII (M10 + 8% Stevia Blend 3) | +/+ | +/- | +/- | +/- | High sweet and low Bitterness |
| XXIII (M10 + 0.2% Stevia Blend 3) | +/+ | +/- | +/+ | -/- | High Sweet and Aftertaste, no Bitterness |
| XXIV (2 + 8% Stevia Blend 3) | +/+/+ | +/+/+ | +/+/+ | +/- | High Sweet and Aftertaste |
| XXV (2 + 0.2% Stevia Blend 3) | +/+/+ | +/+ | +/+/+ | +/- | High Sweet and Aftertaste |
| XXVI (1,2,6,10 + 8% Stevia Blend 3) | -/- | +/+/+ | +/- | +/- | High Glucagon (sweet) and low Bitterness |
| XXVII (1,2,6,10 + 0.2% Stevia Blend 3) | +/+/+/+ | -/- | +/+ | +/+ | High Sweet, Aftertaste and Bitterness |
| XXVIII (iso2 + 8% Stevia Blend 3) | +/- | -/- | +/- | -/- | Low Sweet and no Bitterness |
| XXIX (iso2 + 0.2% Stevia Blend 3) | +/- | +/+ | +/- | +/+ | High Sweet (Glucagon) and Bitterness |

M10 + 8% Stevia Blend 3 isoM10 + 8% Stevia Blend 3

Comp'd 2 + 8% Stevia Blend 3

Comp'd iso2 + 8% Stevia Blend 3

Base solution with 8% Stevia Blend 3

Base solution with 0.2% Stevia Blend 3

Comp'ds 1,2,6,10 + 8% Stevia Blend 3

Comp'ds 1,2,6,10 + 0.2% Stevia Blend 3

8% Stevia Blend 4

Comp'ds 1,10 + 8% Stevia Blend 4

COMPOSITIONS AND METHODS FOR IMPROVING TASTE OF NON-NUTRITIVE SWEETENERS

This application is a 371 of PCT/US2017/051570, filed Sep. 14, 2017. PCT/US2017/051570 has priority of US62/395476 filed Sep. 16, 2016.

FIELD OF THE INVENTION

The present disclosure is directed to a novel sweetener composition having improved taste (e.g., reduced bitterness and/or astringency); and food and beverage products containing the same.

BACKGROUND OF THE INVENTION

Food and beverage manufacturers have been interested in natural, lower calorie or zero-caloric sweeteners such as steviol glycosides, including the rebaudiosides, because there is a market demand for sweeteners with lower calorie content. Rebaudioside A, for example, is currently marketed in commercially available cola products. However, replacing nutritive sweeteners with potent non-nutritive sweeteners has faced obstacles due to off-tastes associated with many non-nutritive sweeteners, including bitterness, astringency, licorice flavor, metallic taste, and/or lingering aftertastes.

Food and beverage manufacturers have attempted to improve the flavor profiles of non-nutritive sweeteners using taste masking or taste altering agents. For example, WO 01/11988 discloses a method of altering or modifying the sensory qualities of artificial or high intensity sweetener compositions by adding an effective amount of a polymeric polyphenol material (e.g., polyproanthocyanidins) extracted from plant materials (e.g., grape seeds, pine barks, lemon tree barks, oak, various berries).

Despite the disclosure of WO '988, there is still a need for compositions and methods suitable for improving the flavor profiles of non-nutritive sweeteners.

BRIEF SUMMARY

In various embodiments, the present disclosure provides a sweetener composition comprising a non-nutritive sweetener, and one or more, or two or more, or three or more, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. These compounds are present in very small amounts to modify the taste profile of the non-nutritive sweetener to reduce bitterness and/or astringency of the sweetener, and/or to improve overall sweet quality (e.g., sugar like taste and roundness) of the sweetener.

In various embodiments, the present disclosure also provides a sweetener composition comprising a non-nutritive sweetener and a flavor-modifying composition comprising one or more, or two or more, or three or more, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

The sweetener composition and/or the flavor-modifying composition of the present disclosure can be substantially free of any compounds having a molecular weight of greater than 500 daltons, greater than 1000 daltons, or greater than 2000 daltons. In certain embodiments, the compounds having a molecular weight of greater than 500 daltons, greater than 1000 daltons, or greater than 2000 daltons can be phenolic oligomers and/or polymeric polyphenols, such as polyproanthcyanidins, polymers of flavanol glycosides, polymers of hydroxycinnamic acid derivatives (esters, glycosides and amides), and/or polymers of gallic acid derivatives (esters, glycosides and amides).

Non-nutritive sweeteners suitable for combination with the compounds noted above include, but are not limited to, a steviol glycoside, Lo Han Guo sweetener, rubusoside, siamenoside, monatin, curculin, glycyrrhizic acid, neohesperidin, dihydrochalcone, glycyrrhizin, glycyphyllin, phloridzin, trilobatin, phyllodulcin, brazzein, hernandulcin, osladin, polypodoside A, baiyunoside, pterocaryoside A and B, mukurozioside, thaumatin, monellin, mabinlins I and II, phlomisoside I, periandrin I, abrusoside A, and cyclocarioside I, mogroside IV, mogroside V, or derivatives or salts thereof, or combinations thereof. In particular embodiments, the non-nutritive sweetener comprises rebaudioside A, rebaudioside D, stevioside, rebaudioside M, or combinations thereof. In certain embodiments, the non-nutritive sweetener comprises an aqueous steviol glycoside composition comprising rebaudioside D and a stevioside composition, with certain rebaudioside D to stevioside composition ratios.

The sweetener compositions of the present disclosure can be in various forms, including solid forms (e.g., granules or powders) and liquid forms (e.g., concentrate or syrup). The sweetener compositions can be used in various products, including beverage products (e.g., ready-to-drink beverages or beverage concentrates) and food products (e.g., oatmeal, cereal, and snack foods).

In typical embodiments, the ready-to-drink beverage is a non-alcoholic beverage, i.e. a beverage that is completely or substantially ethanol free. As used herein, the phrase "substantially ethanol free" means that a given ready-to-drink beverage contains no more than 1% ethanol by weight, and in certain embodiments, no more than 0.5% ethanol by weight, no more than 0.1% ethanol by weight, no more than 0.01% ethanol by weight, no more than 0.001% ethanol by weight, or no more than 0.0001% ethanol by weight. In some embodiments, the ready-to-drink beverage comprises water, a sweetener composition described herein, optionally an acidulant, and optionally a flavorant.

In some embodiments, the ready-to-drink beverage can have fewer than about 200 calories per 8 oz serving, fewer than about 150 calories per 8 oz serving, fewer than about 100 calories per 8 oz serving, fewer than about 70 calories per 8 oz serving, fewer than about 50 calories per 8 oz serving, fewer than about 10 calories per 8 oz serving, or fewer than about 5 calories per 8 oz serving. The ready-to-drink beverage can contain caffeine or can be substantially caffeine free.

In some embodiments, the ready-to-drink beverages are carbonated beverages, non-carbonated beverages, fountain beverages, frozen carbonated beverages, fruit juices, fruit juice-flavored drinks, fruit-flavored drinks, sports drinks, energy drinks, fortified/enhanced water drinks, flavored waters, soy drinks, vegetable drinks, grain-based drinks, malt beverages, fermented drinks, yogurt drinks, kefir, coffee beverages, tea beverages, or dairy beverages, and combinations thereof.

In various embodiments, the present disclosure also provides a method of making a sweetener composition comprising adding to the non-nutritive sweetener one or more, or two or more, or three or more, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. These compounds are present in an amount sufficient to modify the taste profile of the non-nutritive sweetener to reduce bitterness and/or astringency of the sweetener, and/or to improve overall sweet quality (e.g., sugar like taste and roundness) of the sweetener.

In various embodiments, the present disclosure also provides a method of making a sweetener composition, comprising adding to an aqueous solution of the non-nutritive sweetener a flavor-modifying composition comprising one or more, or two or more, or three or more, or four more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, adding the flavor modifying composition to the aqueous solution of the non-nutritive sweetener can be accomplished by contacting the aqueous solution of the non-nutritive sweetener with wood, such as a wood barrel or wood chips. In certain embodiments, the wood can be oak, chestnut, pine, redwood, acacia, or cherry wood. In particular embodiments, the wood is oak. In some embodiments, oak barrels and/or chips can be made of European or American white oak. Wood barrels or chips can be un-charred (toasted), lightly charred, medium charred, or heavily charred. The contacting can take place over a period of hours (e.g., at least about 8 hours), or days (e.g., at least 3 days), or weeks (e.g., at least 2 weeks), depending on the desired flavor profile under an appropriate temperature (e.g., about 10° C. to about 65° C.).

In some embodiments, the method further comprises filtering the aqueous non-nutritive sweetener solution after contacting to remove undesirable colors and/or odors. The filtration can be carried out by a carbon filtration or a membrane filtration.

In one embodiment, the present disclosure provides a sweetener composition comprising (1) a non-nutritive sweetener; and (2) one or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the sweetener composition comprises (1) a non-nutritive sweetener; and (2) two or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the sweetener composition comprises three or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the sweetener composition comprises four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the sweetener composition is substantially free of any compounds having a molecular weight of greater than 500 daltons, greater than 1000 daltons or greater than 2000 daltons.

In some embodiments, the present disclosure provides a sweetener composition, comprising (1) a non-nutritive sweetener; and (2) a flavor-modifying composition comprising one or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the flavor-modifying composition is substantially free of any compounds having a molecular weight of greater than 500 daltons, greater than 1000 daltons or greater than 2000 daltons.

In some embodiments, the flavor-modifying composition is an aqueous composition.

In some embodiments, the flavor-modifying composition comprises two or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the flavor-modifying composition comprises three or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the flavor-modifying composition comprises four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the compound furfural is present in an amount from about 6 ppb to about 10 ppm, from about 13 ppb to about 5 ppm, or from about 80 ppb to about 5 ppm.

In some embodiments, the compound 4-hexen-1-ol is present in an amount from about 0.6 ppb to about 1 ppm, from about 1.3 ppb to about 0.5 ppm, or from about 8 ppb to about 0.5 ppm.

In some embodiments, the compound trans-2,4-hexadienal is present in an amount from about 2.5 ppb to about 4 ppm, from about 5 ppb to about 2 ppm, or from about 30 ppb to about 2 ppm.

In some embodiments, the compound 2,4-hexadien-1-ol is present in an amount from about 0.4 ppb to about 4 ppm, from about 2 ppb to about 3 ppm, from about 4 ppb to about 1.5 ppm, or from about 24 ppb to about 1.5 ppm.

In some embodiments, the compound 5-methyl-furfural is present in an amount from about 0.3 ppb to about 1 ppm, from about 0.5 ppb to about 0.5 ppm, from about 0.7 ppb to about 0.25 ppm, or from about 4 ppb to about 0.25 ppm.

In some embodiments, the compound delta-tetradecalactone is present in an amount from about 0.1 ppb to about 0.04 ppm, from about 0.1 ppb to about 0.02 ppm, or from about 0.3 ppb to about 0.02 ppm.

In some embodiments, the compound cis-4-methyl-5-butyldihydro-2(3H)-furanone and/or trans-4-methyl-5-butyldihydro-2(3H)-furanone is present in an amount from about 0.1 ppb to about 0.5 ppm, from about 0.2 ppb to about 0.3 ppm, from about 0.3 ppb to about 0.1 ppm, or from about 1.6 ppb to about 0.1 ppm.

In some embodiments, the compound 3-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm.

In some embodiments, the compound ethyl octanoate is present in an amount from about 0.1 ppb to about 0.4 ppm, from about 0.5 ppb to about 0.2 ppm, or from about 3.2 ppb to about 0.2 ppm.

In some embodiments, the compound ethyl decanoate is present in an amount from about 0.1 ppb to about 2.4 ppm, from about 0.3 ppb to about 1.2 ppm, or from about 1.6 ppb to about 1.2 ppm.

In some embodiments, the compound ethyl hexadecanoate is present in an amount from about 0.6 ppb to about 1 ppm, from about 1.3 ppb to about 0.5 ppm, or from about 7.9 ppb to about 0.5 ppm.

In some embodiments, the compound 2-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm.

In some embodiments, the non-nutritive sweetener comprises a steviol glycoside, Lo Han Guo sweetener, rubusoside, siamenoside, monatin, curculin, glycyrrhizic acid, neohesperidin, dihydrochalcone, glycyrrhizin, glycyphyllin, phloridzin, trilobatin, phyllodulcin, brazzein, hernandulcin, osladin, polypodoside A, baiyunoside, pterocaryoside A and B, mukurozioside, thaumatin, monellin, mabinlins I and II, phlomisoside I, periandrin I, abrusoside A, and cyclocarioside I, mogroside IV, mogroside V, or derivatives or salts thereof, or combinations thereof.

In some embodiments, the non-nutritive sweetener comprises a steviol glycoside.

In some embodiments, the non-nutritive sweetener comprises stevioside, rebaudioside A, rebaudioside B, rebaudioside C, rebaudioside D, rebaudioside E, rebaudioside F, rebaudioside G rebaudioside H rebaudioside I, rebaudioside J, rebaudioside K, rebaudioside L, rebaudioside M, rebaudioside N, rebaudioside O, rebaudioside P, rebaudioside Q, steviolbioside, dulcoside A, or derivatives, or combinations thereof.

In some embodiments, the non-nutritive sweetener comprises rebaudioside A, rebaudioside D, stevioside, rebaudioside M, or combinations thereof.

In some embodiments, the non-nutritive sweetener comprises rebaudioside A, stevioside, rebaudioside D, or combinations thereof.

In some embodiments, the non-nutritive sweetener comprises an aqueous steviol glycoside composition comprising rebaudioside D and a stevioside composition.

In some embodiments, the rebaudioside D is present from about 0.5 wt % to about 1.5 wt %, from about 1 wt % to about 1.5 wt %, from about 1.3 wt % to about 1.4 wt %, or is present at about 1.3 wt %, about 1.4 wt % or about 1.5 wt % of the aqueous steviol glycoside composition.

In some embodiments, the stevioside composition and the rebaudioside D are present in a ratio of from about 1:1 to about 10:1, from about 2:1 to about 7:1, or about 2:1, about 3:1, about 5:1 or about 6:1.

In some embodiments, the stevioside composition comprises stevioside and a second steviol glycoside selected from the group consisting of rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside O, steviolbioside, rubusoside, and dulcoside A.

In some embodiments, the second steviol glycoside is rebaudioside A or rebaudioside M.

In some embodiments, the stevioside and rebaudioside A are present in a ratio of from less than 95:5 to 1:99, or from about 1:1 to about 2:98.

The present disclosure further provides a ready-to-drink beverage comprising water; a sweetener composition, optionally an acidulant selected from the group consisting of phosphoric acid, citric acid, malic acid, tartaric acid, lactic acid, formic acid, ascorbic acid, fumaric acid, gluconic acid, succinic acid, maleic acid, adipic acid, and mixtures thereof; and optionally a flavorant.

In certain embodiments, the beverage is selected from the group consisting of carbonated beverages, non-carbonated beverages, fountain beverages, frozen carbonated beverages, fruit juices, fruit juice-flavored drinks, fruit-flavored drinks, sports drinks, energy drinks, fortified/enhanced water drinks, flavored waters, soy drinks, vegetable drinks, grain-based drinks, malt beverages, fermented drinks, yogurt drinks, kefir, coffee beverages, tea beverages, or dairy beverages, and combinations thereof.

In certain embodiments, the water is carbonated water.

In certain embodiments, the flavorant comprises a cola flavorant, a tea flavorant, a caramel flavorant, and a coffee flavorant.

In certain embodiments, the ready-to-drink beverage further comprises caffeine.

In other embodiments, the ready-to-drink beverage is substantially free of caffeine.

In some embodiments, the beverage has fewer than about 200 calories per 8 oz serving.

In some embodiments, the beverage further comprises a nutritive sweetener.

The present disclosure further provides a beverage concentrate comprising water and the sweetener composition described herein.

The present disclosure further provides a food component and a sweetener composition as described herein.

The present disclosure also provides a method of making a sweetener composition, the method comprising adding to a non-nutritive sweetener one or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the method comprises adding two or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the method comprises adding three or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the method comprises four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

The present disclosure also provides a method of making a sweetener composition, comprising adding to an aqueous solution comprising a non-nutritive sweetener, a flavor-modifying composition comprising one or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In certain embodiments, the flavor-modifying composition comprises two or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In certain embodiments, the flavor-modifying composition comprises three or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, the flavor-modifying composition comprises four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

In some embodiments, adding comprises contacting the aqueous solution of the non-nutritive sweetener in an oak barrel or with oak chips.

In some embodiments, the contacting occurs at from about 10° C. to about 50° C., or from 21° C. to 40° C., for at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, or at least about 6 weeks.

In some embodiments, the method further comprises filtering the aqueous solution of the non-nutritive sweetener after the adding.

In some embodiments, the filtering comprises a carbon filtration or a membrane filtration.

In some embodiments, the aqueous solution comprises from about 1 wt % to about 25 wt %, from about 5 wt % to about 15 wt %, from about 6 wt % to about 13 wt %, or about 7 wt %, about 8 wt %, about 9 wt %, about 10 wt %, about 11 wt % or about 12 wt % of the non-nutritive sweetener.

In some embodiments, the non-nutritive sweetener comprises a steviol glycoside, Lo Han Guo sweetener, rubusoside, siamenoside, monatin, curculin, glycyrrhizic acid, neohesperidin, dihydrochalcone, glycyrrhizin, glycyphyllin, phloridzin, trilobatin, phyllodulcin, brazzein, hernandulcin, osladin, polypodoside A, baiyunoside, pterocaryoside A and B, mukurozioside, thaumatin, monellin, mabinlins I and II, phlomisoside I, periandrin I, abrusoside A, and cyclocarioside I, mogroside IV, mogroside V, or derivatives or salts thereof, or combinations thereof.

In some embodiments, the non-nutritive sweetener comprises a steviol glycoside.

In some embodiments, the non-nutritive sweetener comprises stevioside, rebaudioside A, rebaudioside B, rebaudioside C, rebaudioside D, rebaudioside E, rebaudioside F, rebaudioside G rebaudioside H rebaudioside I, rebaudioside J, rebaudioside K, rebaudioside L, rebaudioside M, rebaudioside N, rebaudioside O, rebaudioside P, rebaudioside Q, steviolbioside, dulcoside A, or derivatives, or combinations thereof.

In some embodiments, the non-nutritive sweetener comprises rebaudioside A, rebaudioside D, stevioside, rebaudioside M, or combinations thereof.

In certain embodiments, the non-nutritive sweetener comprises an aqueous steviol glycoside composition comprising rebaudioside D and a stevioside composition.

In certain embodiments, the rebaudioside D is present from about 0.5 wt % to about 1.5 wt %, from about 1 wt % to about 1.5 wt %, from about 1.3 wt % to about 1.4 wt %, or is present at about 1.3 wt %, about 1.4 wt % or about 1.5 wt % of the aqueous steviol glycoside composition.

In certain embodiments, the stevioside composition and the rebaudioside D are present in a ratio of from about 1:1 to about 10:1, from about 2:1 to about 7:1, or about 2:1, about 3:1, about 5:1 or about 6:1.

In certain embodiments, the stevioside composition comprises stevioside and a second steviol glycoside selected from the group consisting of rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside O, steviolbioside, rubusoside, and dulcoside A.

In certain embodiments, the second steviol glycoside is rebaudioside A or rebaudioside M.

In certain embodiments, the stevioside and rebaudioside A are present in a ratio of from less than 95:5 to 1:99, or from about 1:1 to about 2:98.

In certain embodiments, the sweetener composition further comprises a nutritive sweetener.

In certain embodiments, the nutritive sweetener is sucrose or high-fructose corn syrup.

BRIEF DESCRIPTION OF THE DRAWINGS/FIGURES

The foregoing summary, as well as the following detailed description of the embodiments, will be better understood when read in conjunction with the appended figures. For the purpose of illustration, the figures may describe the use of specific embodiments. It should be understood, however, that the compounds, formulations, compositions, and methods described herein are not limited to the precise embodiments discussed or described in the figures.

FIG. 1 depicts an exemplary oak barrel.

Figure 3:
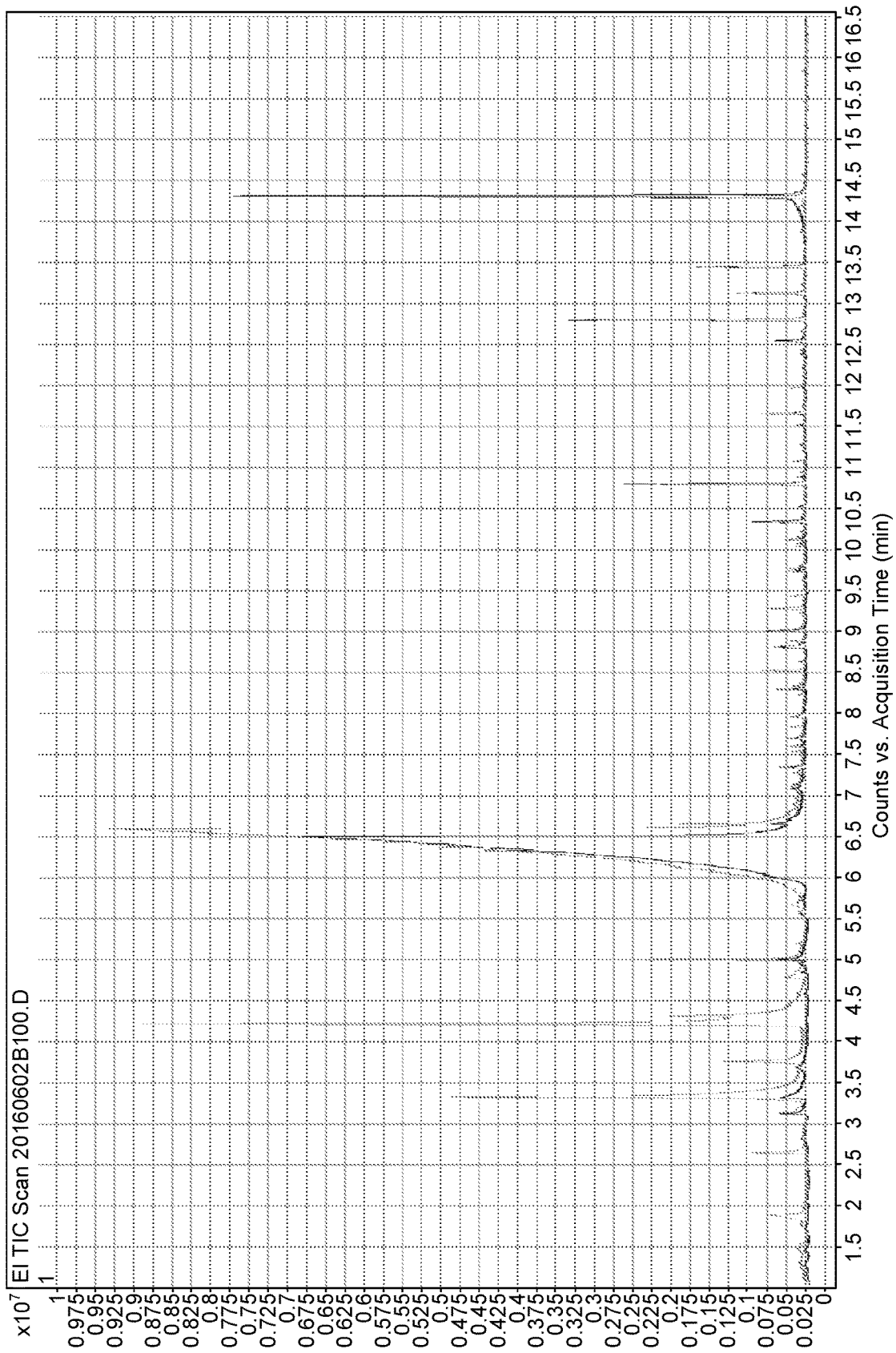

FIG. 3 is a gas chromatogram comparing the components of aqueous steviol solutions stored in an oak barrel and a glass container, respectively, for 21 days at room temperature. This chromatogram shows that the compounds migrating from the oak barrel into the *stevia* solution are volatile compounds with boiling points less than 300° C. and molecular weights less than 300 daltons.

Figure 4:
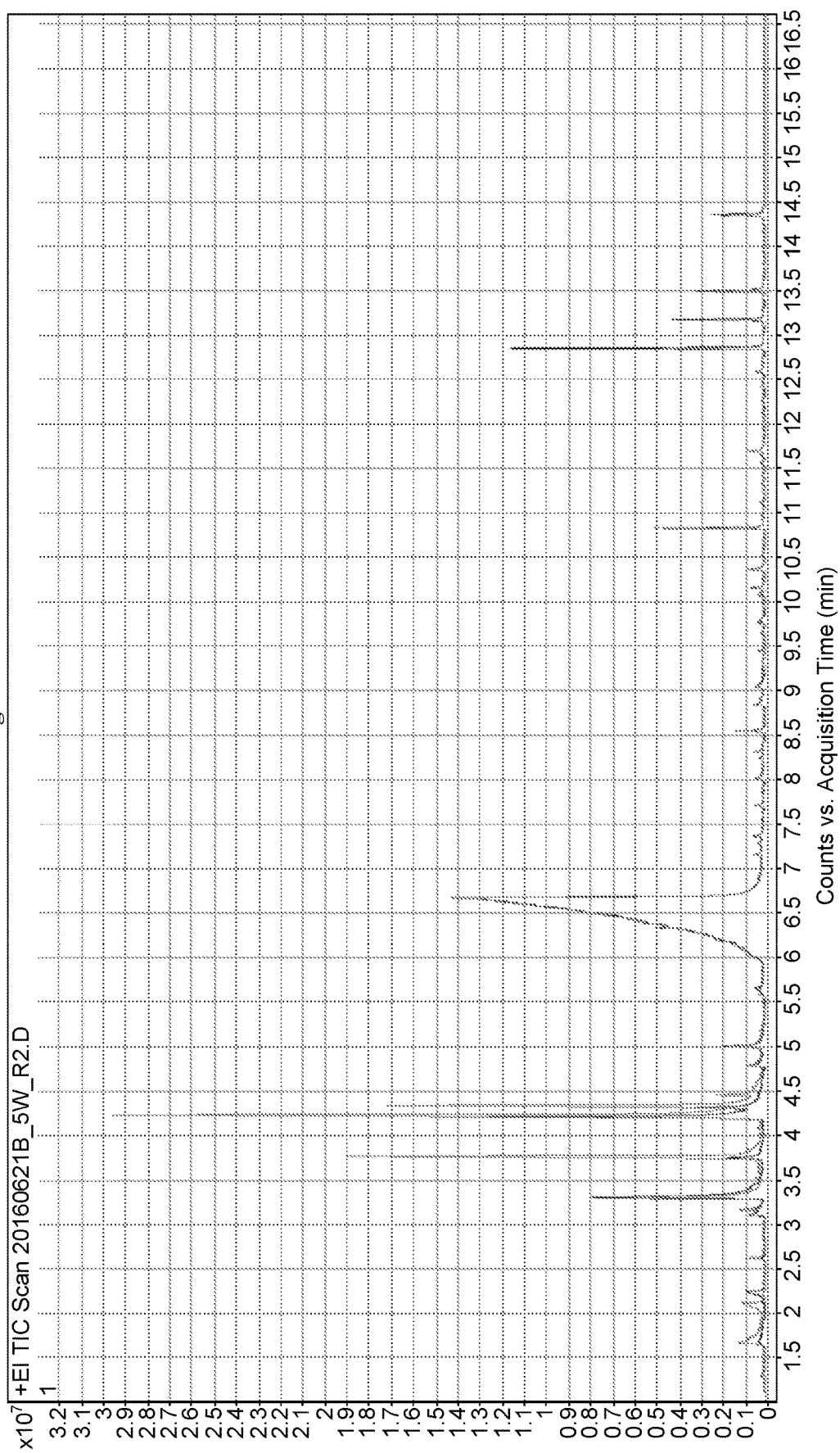

FIG. 4 is a gas chromatogram of an aqueous steviol solution stored in an oak barrel for 3 weeks and 5 weeks at room temperature, respectively.

Figure 5:
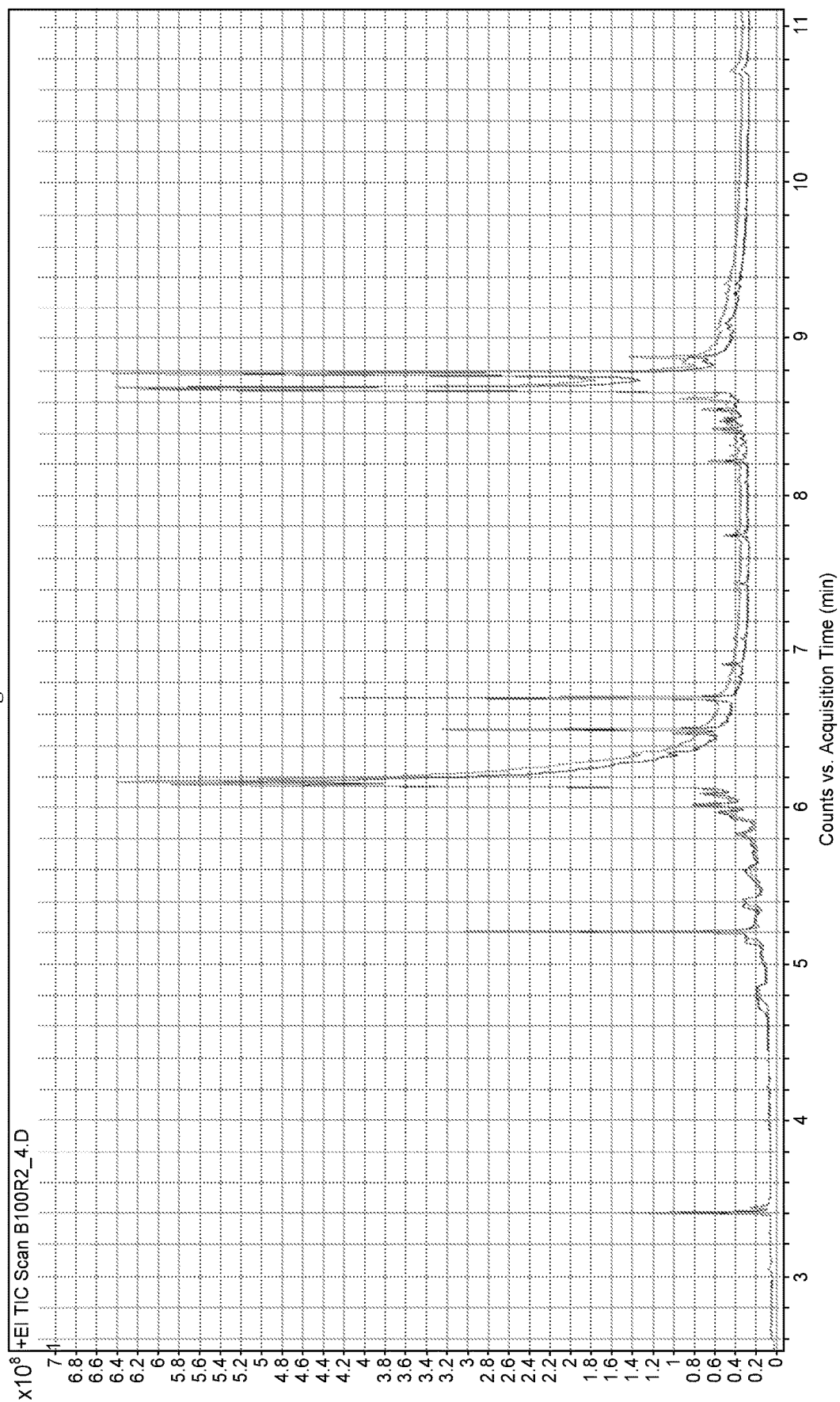

FIG. 5 (top panel) is a trimethylsilyl derivatized gas chromatogram of an aqueous steviol solution stored in an oak barrel and a glass container, respectively, for 21 days at room temperature. The trimethylsilyl derivatization technique is used to identify and quantify semi-volatile compounds, i.e., compounds with a boiling point greater than 300° C., by making these compounds more volatile via the addition of a non-polar group.

Figure 6:
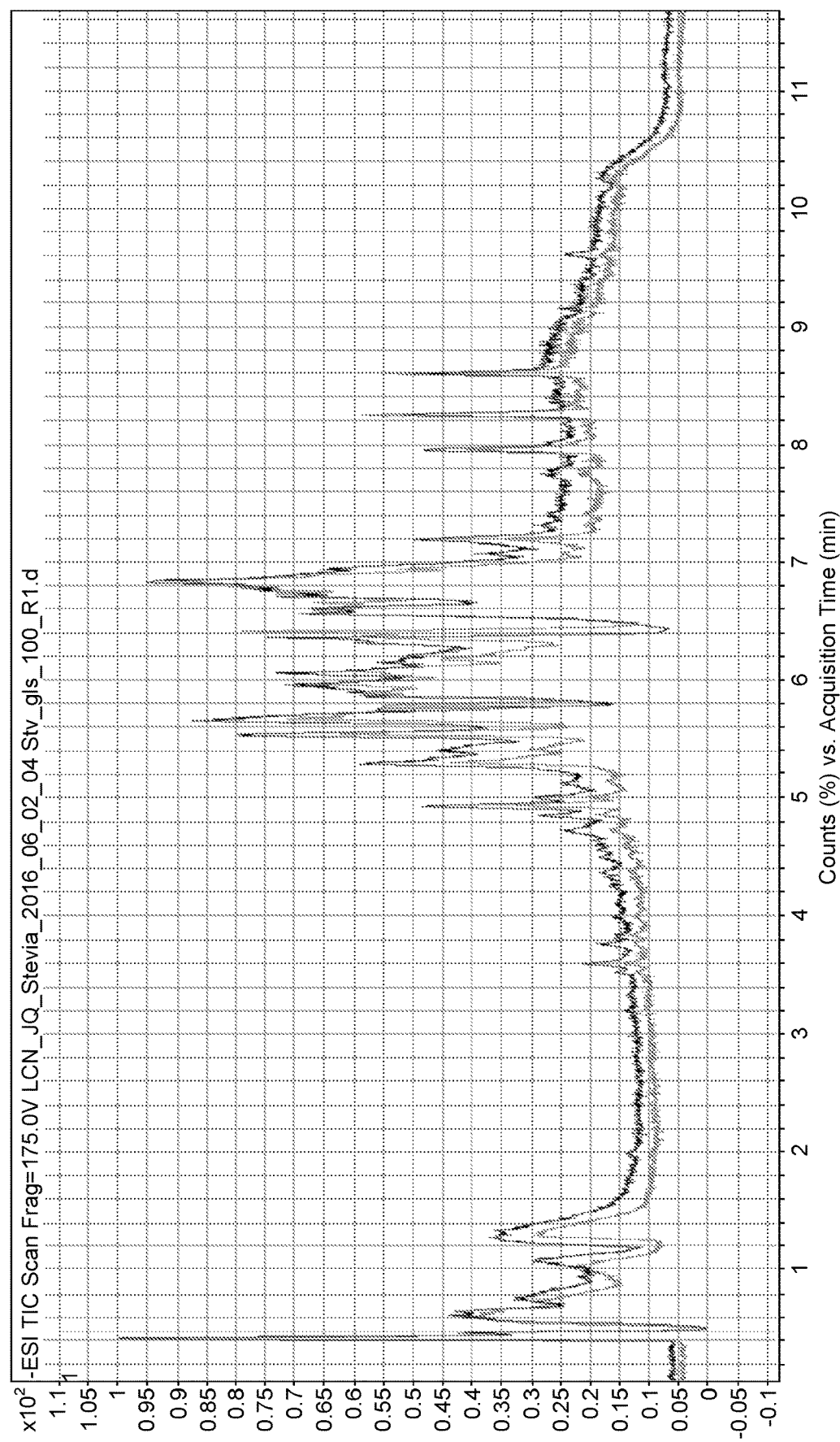

FIG. 6 (middle panel) is a negative LCMS spectrum (liquid chromatography-mass spectrometry) of an aqueous steviol solution stored in an oak barrel and a glass container, respectively, for 21 days at room temperature. "Negative" denotes negative ionization mode of the mass spectrometry.

Figure 7:
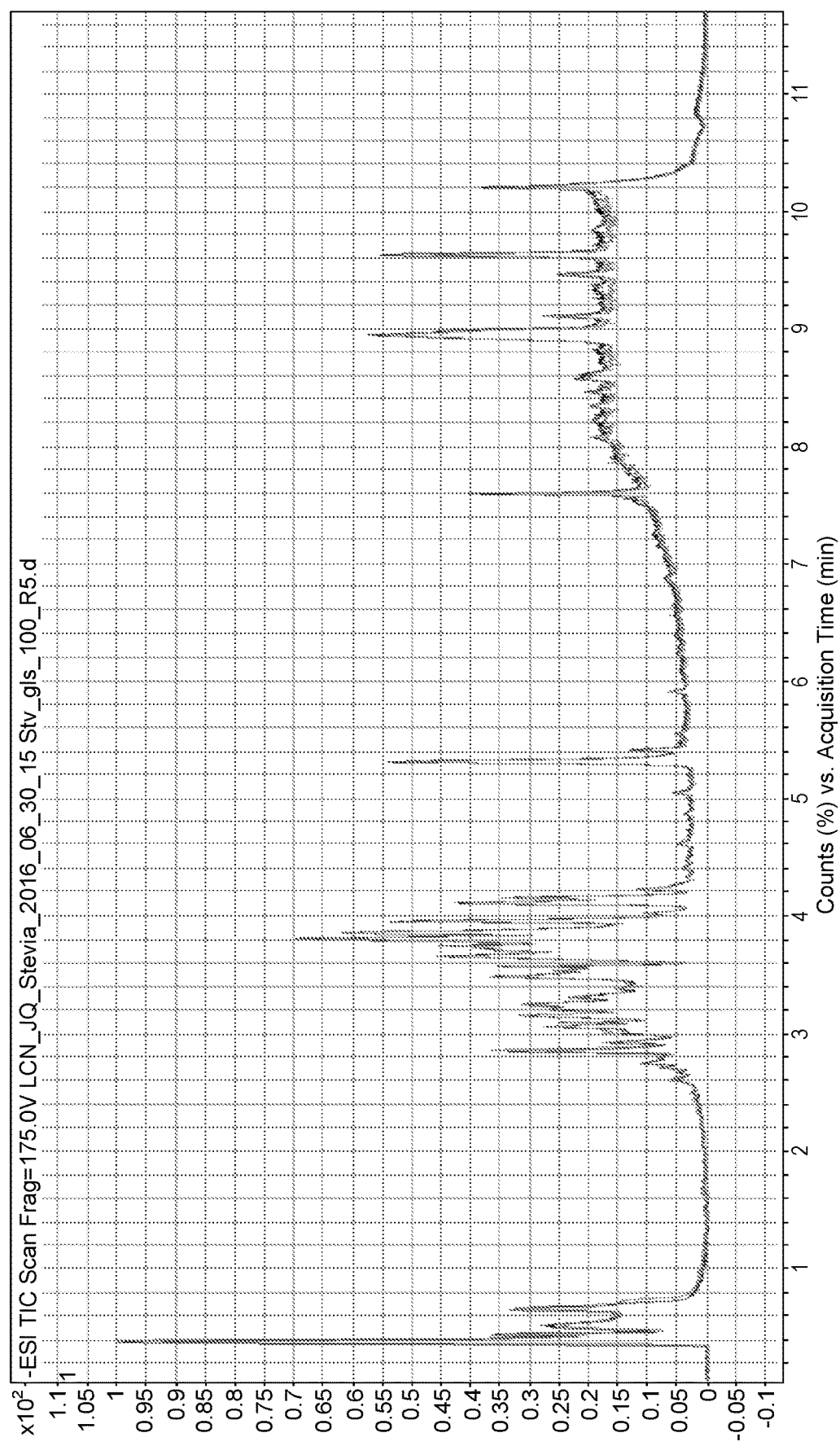

FIG. 7 (bottom panel) is a positive LCMS spectrum (liquid chromatography-mass spectrometry) of an aqueous steviol solution stored in an oak barrel and a glass container, respectively, for 21 days at room temperature. "Positive" denotes positive ionization mode of the mass spectrometry.

Figure 8:
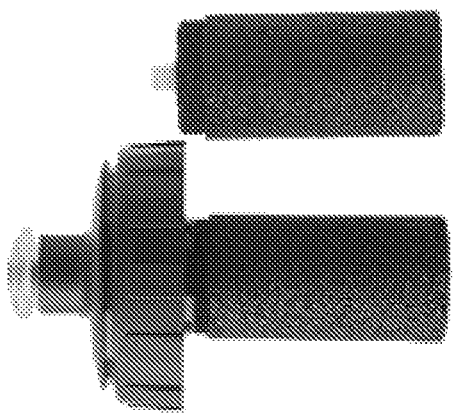

FIG. 8 depicts exemplary carbon filtration means.

Figure 9A:
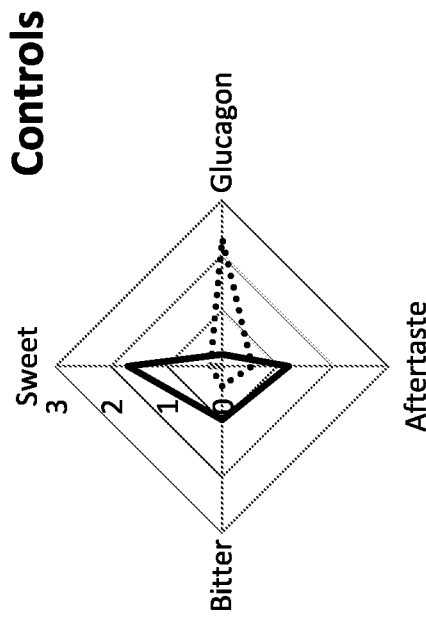
Figure 9B:
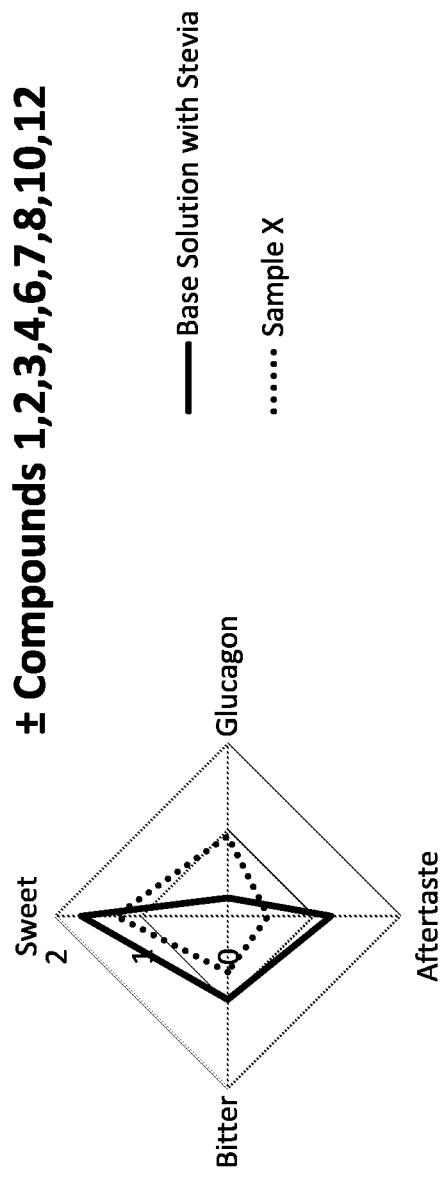

FIGS. 9A-9B are radar graphs depicting the level of activation of the sweet, aftertaste, bitter, and glucagon receptors for a sample containing a base solution without a *stevia* blend, a sample containing a base solution with a *stevia* blend, and a sample containing a *stevia* blend combined with one or more compounds disclosed herein.

Figure 10A:
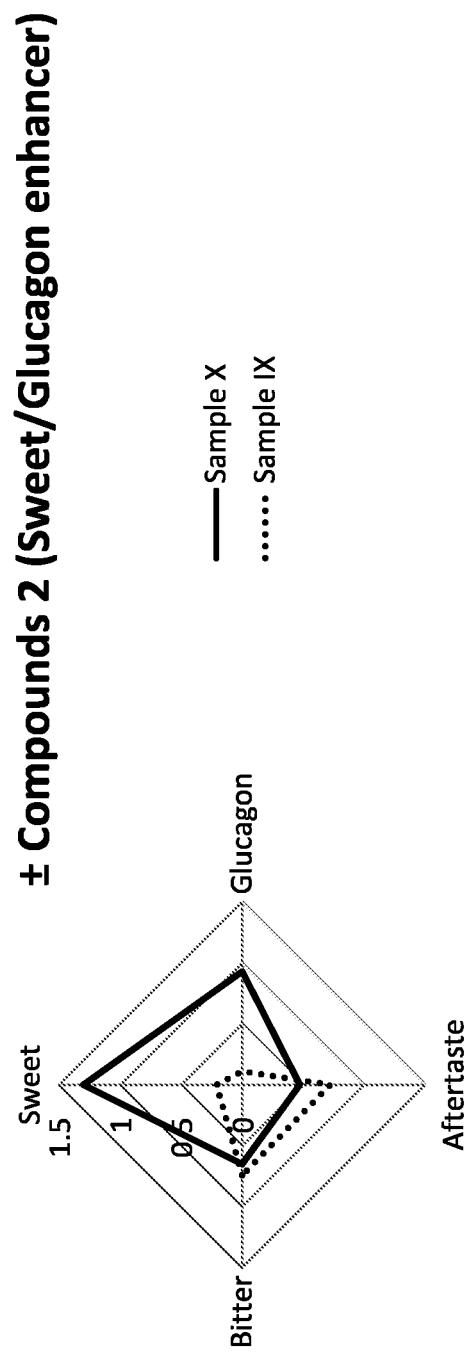
Figure 10B:
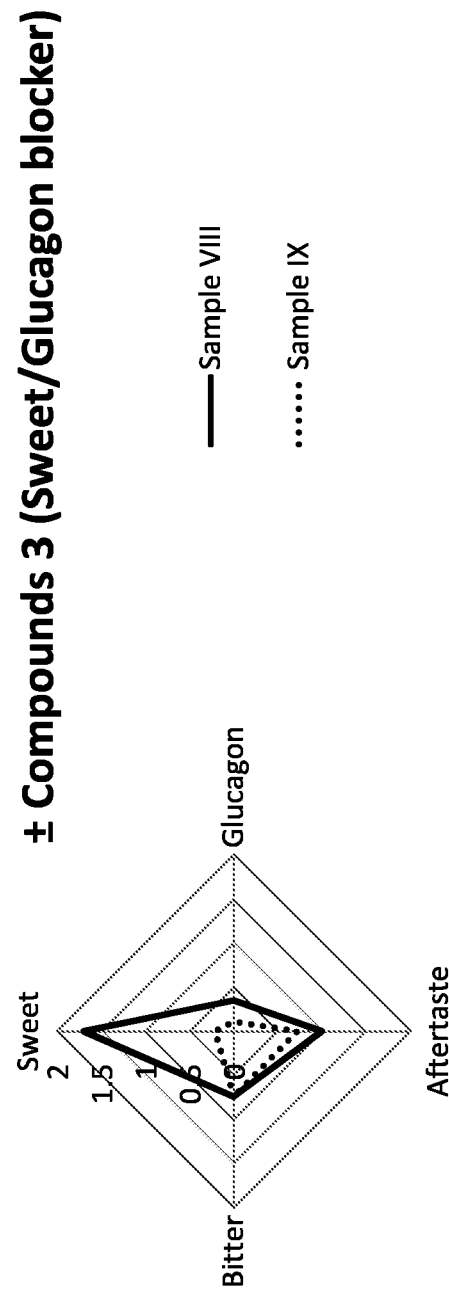

FIGS. 10A-10B are radar graphs depicting the level of activation of the sweet, aftertaste, bitter, and glucagon receptors for samples containing a *stevia* blend and one or more compounds disclosed herein.

Figure 11A:
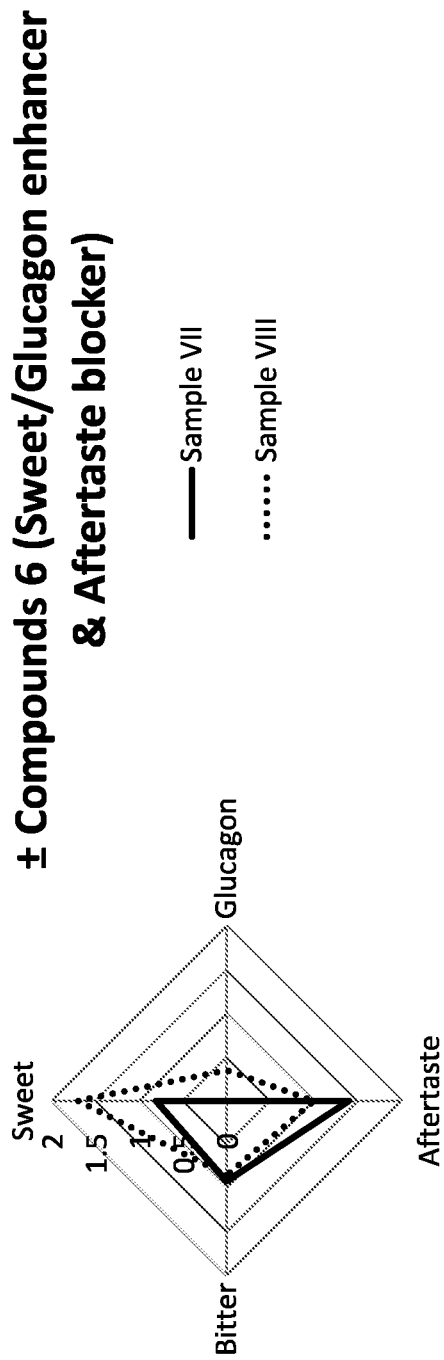
Figure 11B:
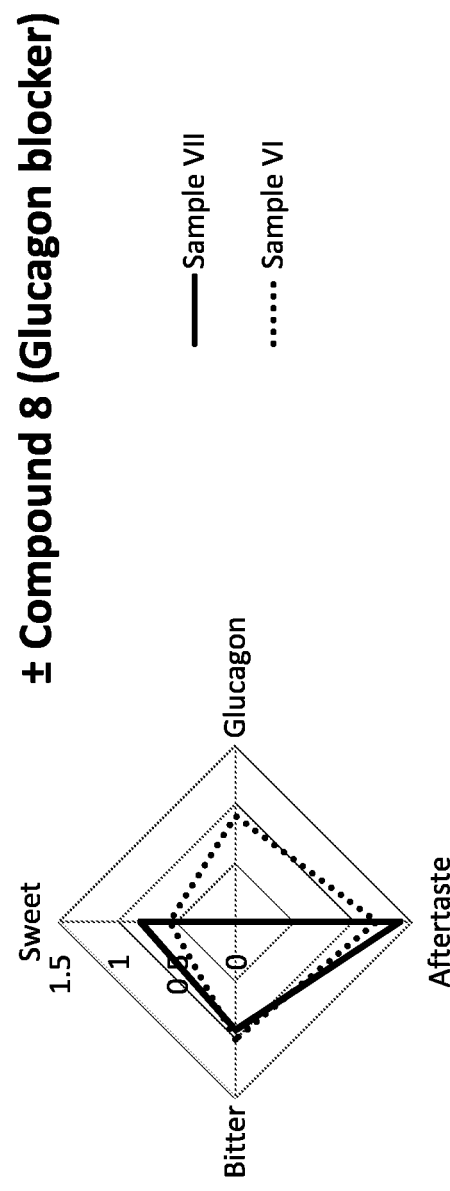

FIGS. 11A-11B are radar graphs depicting the level of activation of the sweet, aftertaste, bitter, and glucagon receptors for samples containing a *stevia* blend and one or more compounds disclosed herein.

Figure 12A:
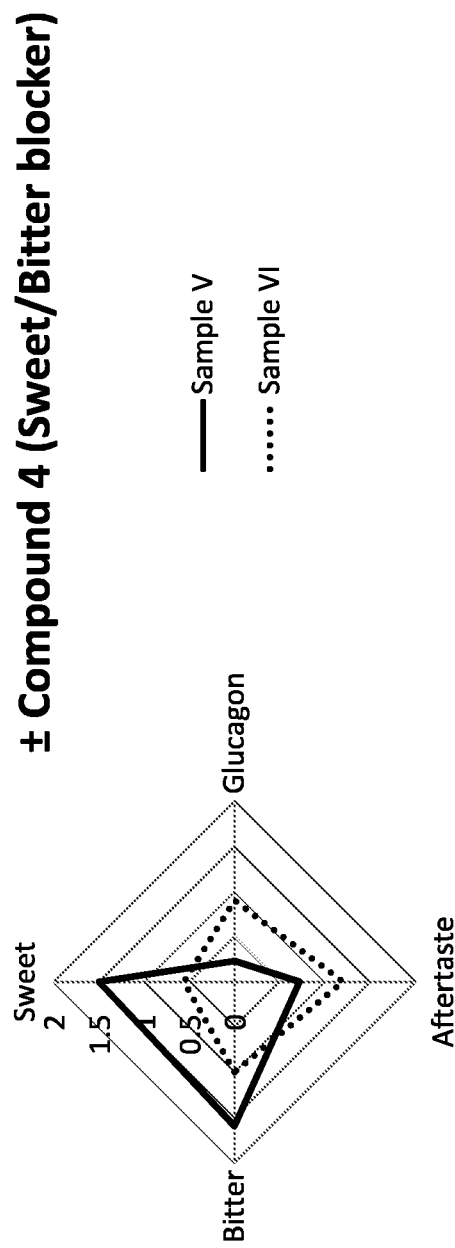
Figure 12B:
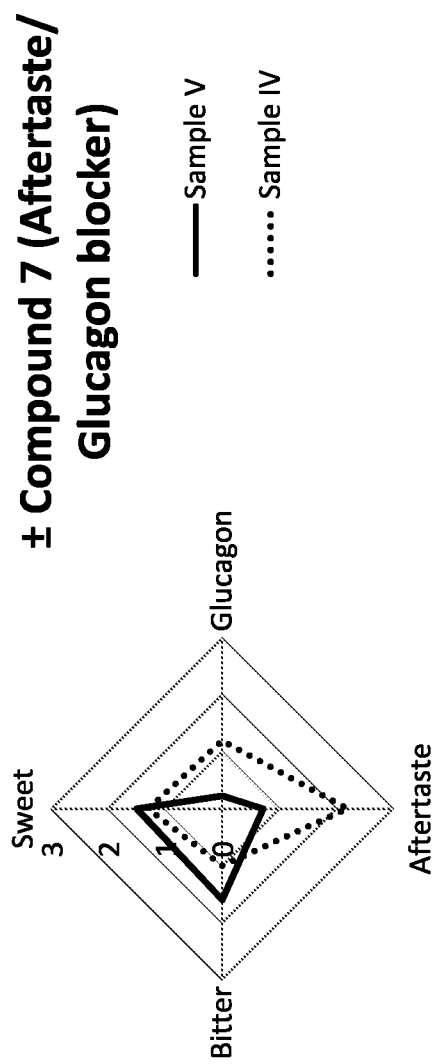

FIGS. 12A-12B are radar graphs depicting the level of activation of the sweet, aftertaste, bitter, and glucagon receptors for samples containing a *stevia* blend and one or more compounds disclosed herein.

Figure 13:
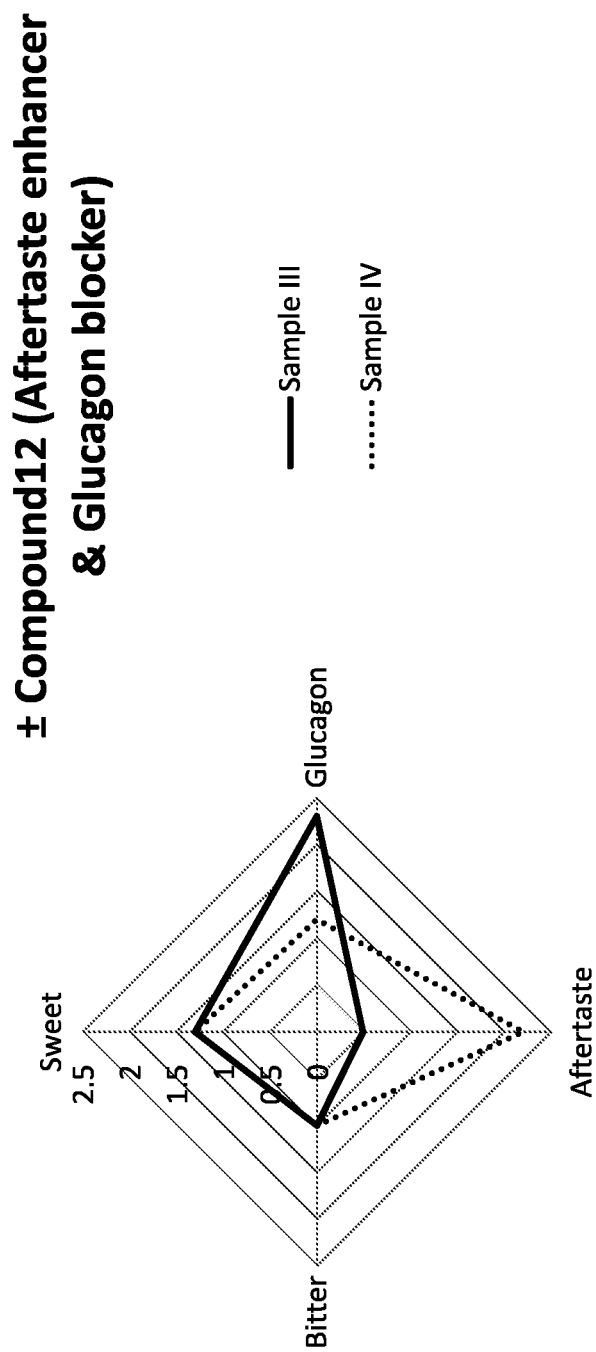

FIG. 13 is a radar graph depicting the level of activation of the sweet, aftertaste, bitter, and glucagon receptors for samples containing a *stevia* blend and one or more compounds disclosed herein.

FIGS. 14A-14B are radar graphs depicting the level of activation of the sweet, aftertaste, bitter, and glucagon receptors for individual compounds disclosed herein and for samples containing a *stevia* blend and one or more compounds disclosed herein.

FIGS. 15A-15B are radar graphs depicting the level of activation of the sweet, aftertaste, bitter, and glucagon receptors for individual compounds disclosed herein and for samples containing a *stevia* blend and one or more compounds disclosed herein.

Figure 16A:
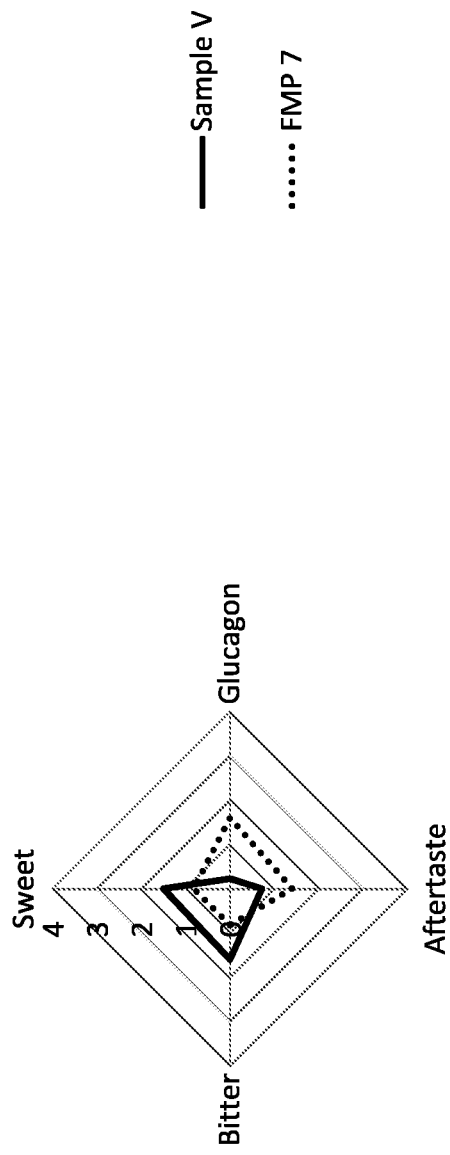
Figure 16B:
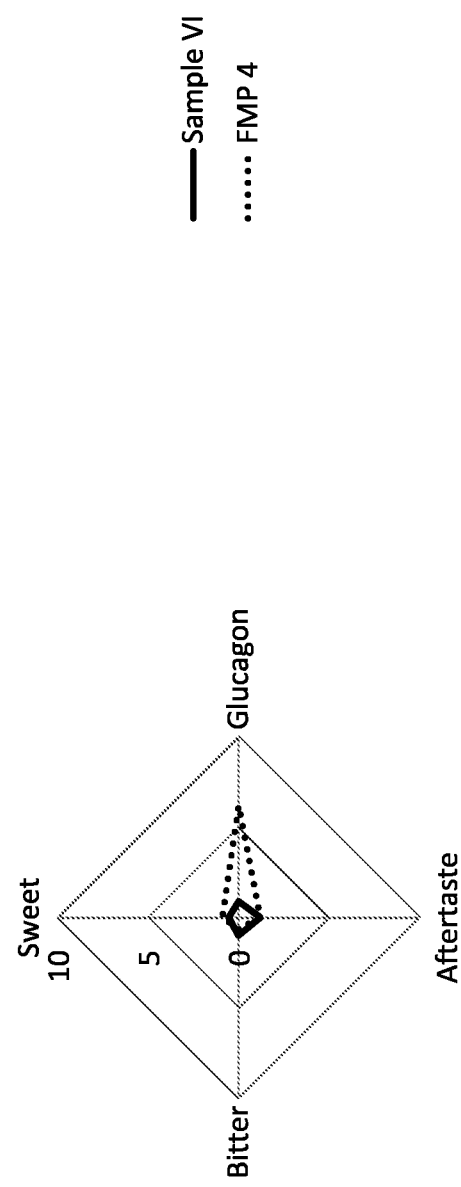

FIGS. 16A-16B are radar graphs depicting the level of activation of the sweet, aftertaste, bitter, and glucagon receptors for individual compounds disclosed herein and for samples containing a *stevia* blend and one or more compounds disclosed herein.

Figure 17A:
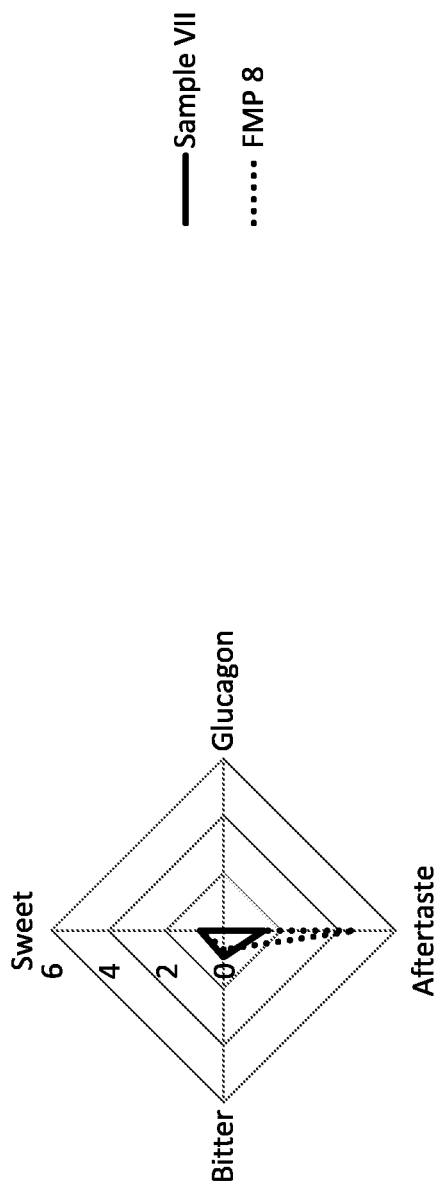
Figure 17B:
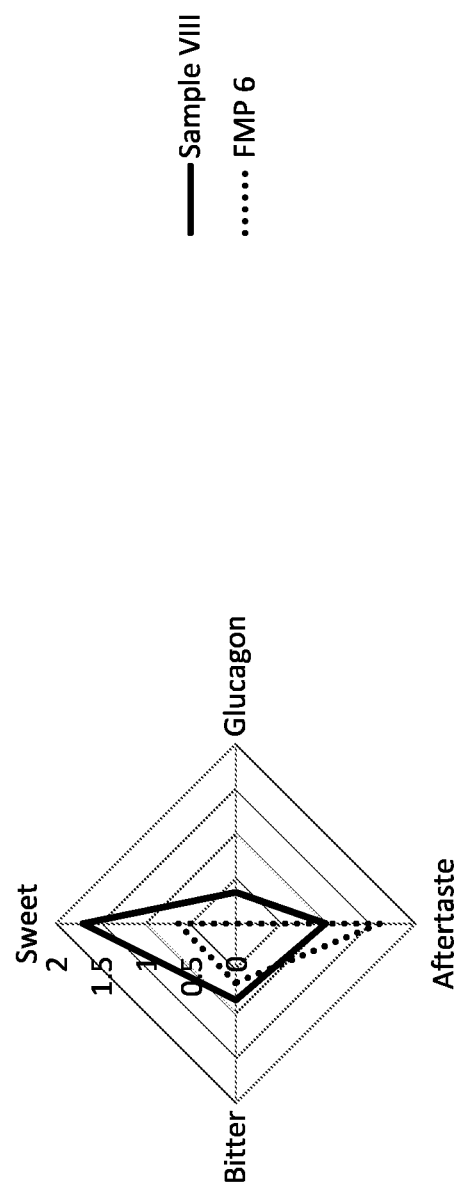

FIGS. 17A-17B are radar graphs depicting the level of activation of the sweet, aftertaste, bitter, and glucagon receptors for individual compounds disclosed herein and for samples containing a *stevia* blend and one or more compounds disclosed herein.

FIGS. 18A-18B are radar graphs depicting the level of activation of the sweet, aftertaste, bitter, and glucagon receptors for individual compounds disclosed herein and for samples containing a *stevia* blend and one or more compounds disclosed herein.

Figure 19:
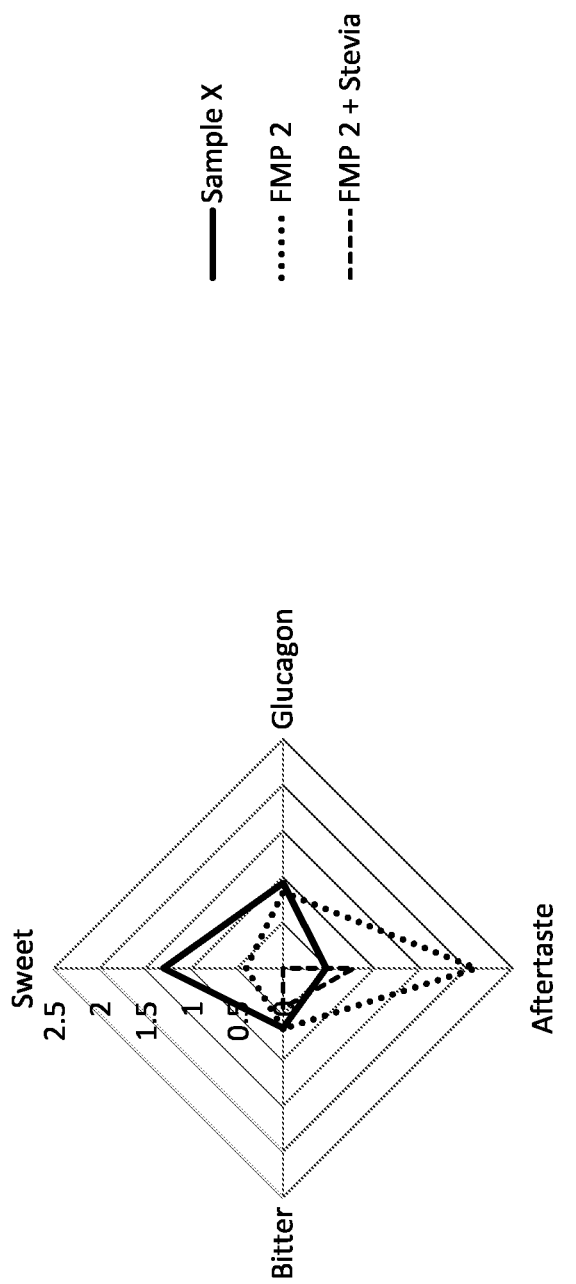

FIG. 19 is a radar graph depicting the level of activation of the sweet, aftertaste, bitter, and glucagon receptors for an individual compound disclosed herein and for samples containing a *stevia* blend and one or more compounds disclosed herein.

FIG. 20 is a group of radar graphs depicting the level of activation of the T1R2, T1R3, GLUT4, and glucagon receptors for samples containing sucrose, sucralose, high fructose corn syrup (HFCS), the *stevia* blend RA50, and a 97 wt % solution of rebaudioside A.

FIG. 21 is table listing the level of activation of the sweet, aftertaste, bitter, and glucagon receptors for samples containing a *stevia* blend and one or more compounds disclosed herein.

Figure 22A:
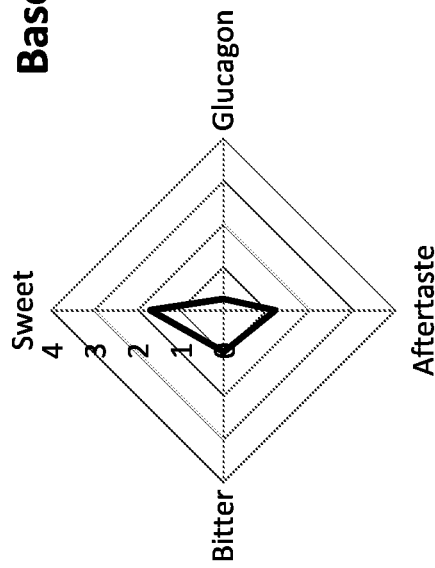
Figure 22B:
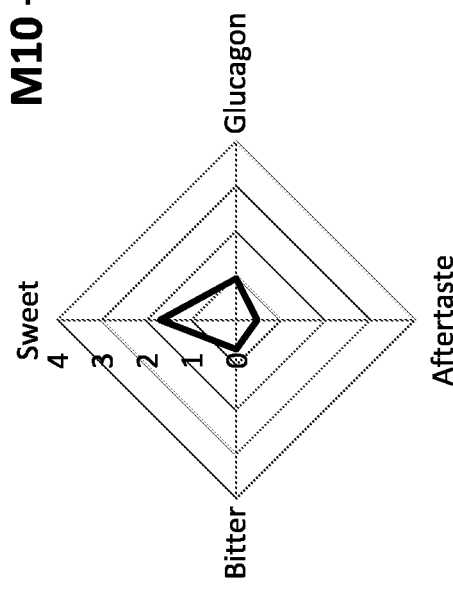

FIGS. 22A-22B are radar graphs depicting the level of activation of the sweet, aftertaste, bitter, and glucagon receptors for a sample containing a *stevia* blend and a sample containing a *stevia* blend and one or more compounds disclosed herein.

Figure 23A:
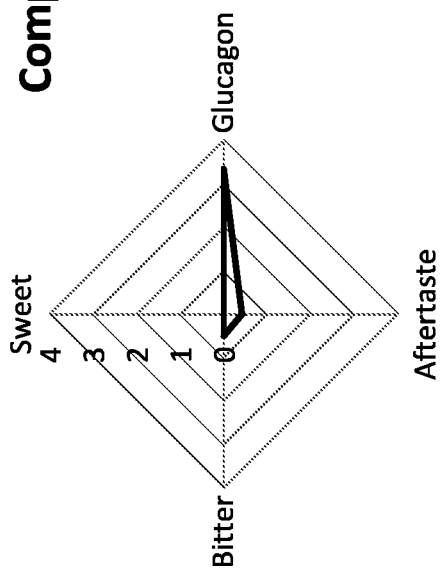
Figure 23B:
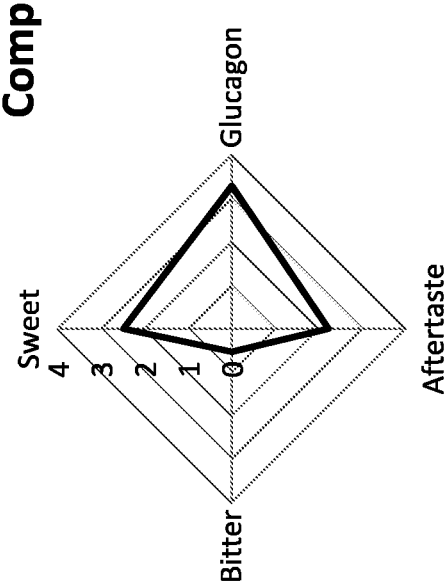

FIGS. 23A-23B are radar graphs depicting the level of activation of the sweet, aftertaste, bitter, and glucagon receptors for samples containing a *stevia* blend and one or more compounds disclosed herein.

Figure 24A:
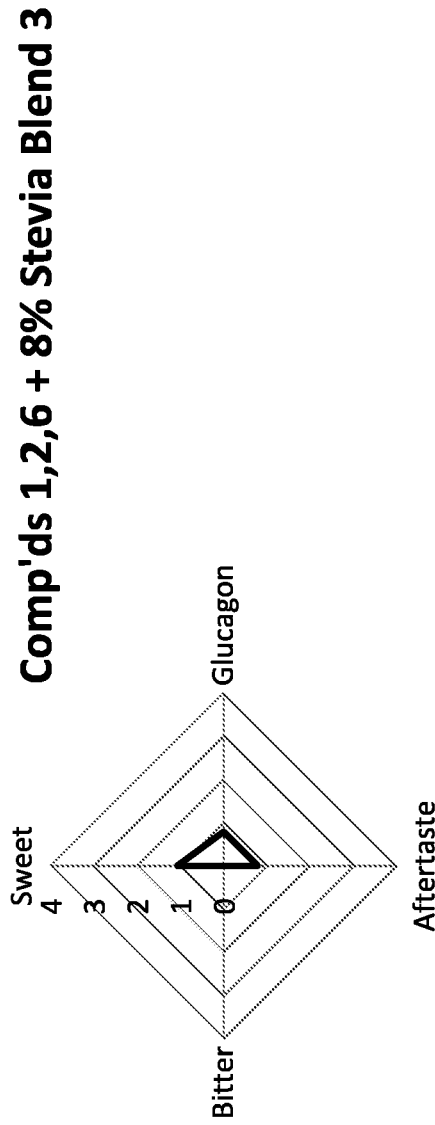
Figure 24B:
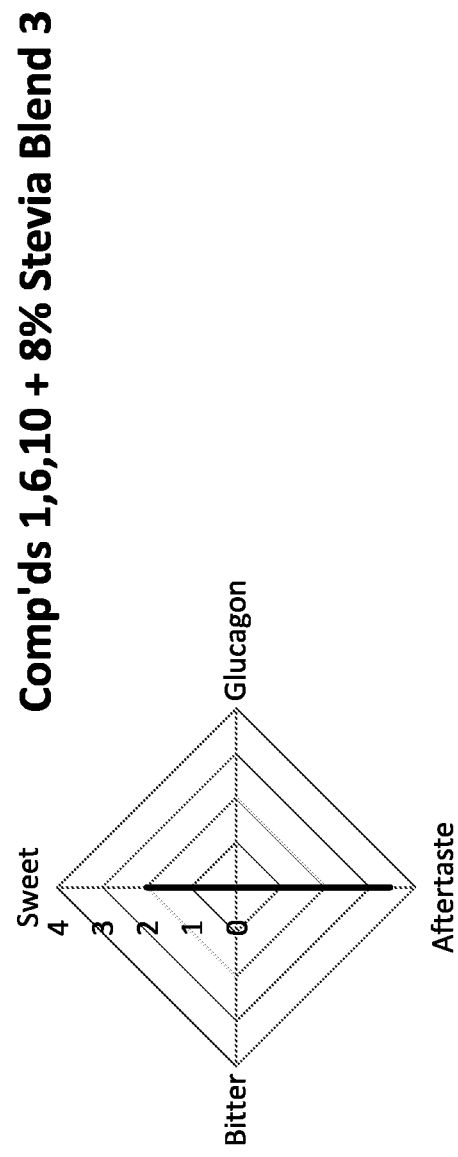

FIGS. 24A-24B are radar graphs depicting the level of activation of the sweet, aftertaste, bitter, and glucagon receptors for samples containing a *stevia* blend and one or more compounds disclosed herein.

Figure 25A:
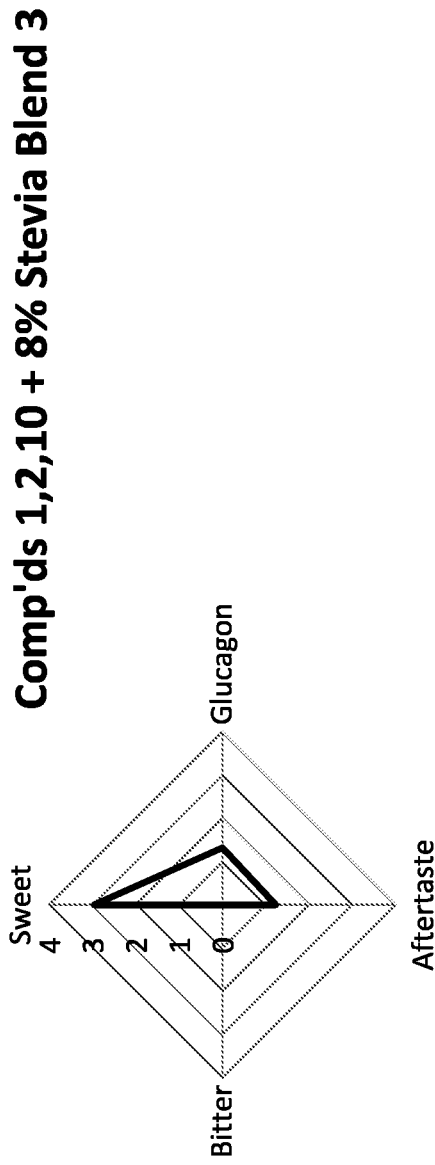
Figure 25B:
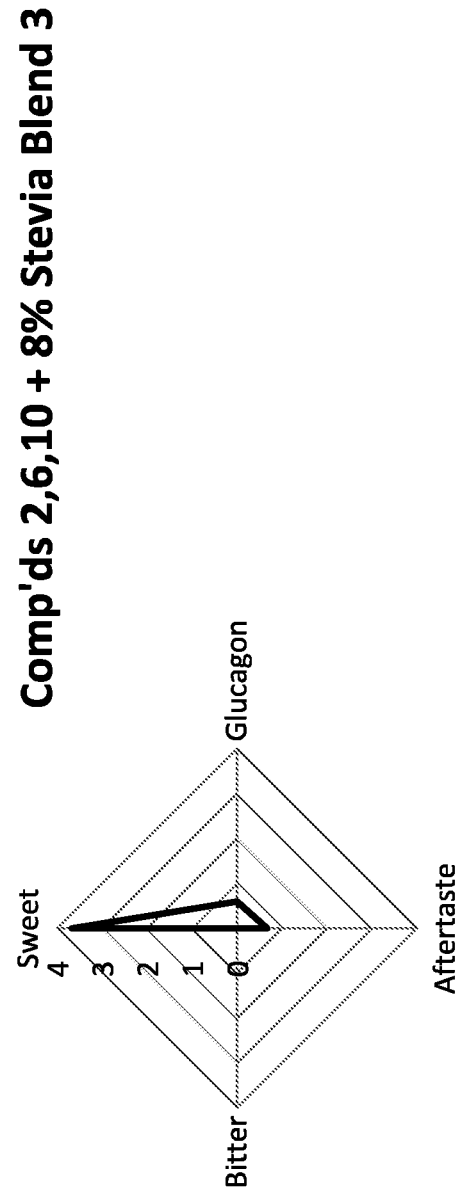

FIGS. 25A-25B are radar graphs depicting the level of activation of the sweet, aftertaste, bitter, and glucagon receptors for samples containing a *stevia* blend and one or more compounds disclosed herein.

Figure 26A:
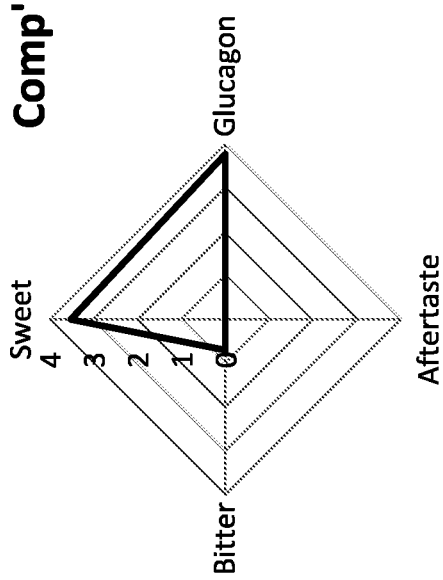
Figure 26B:
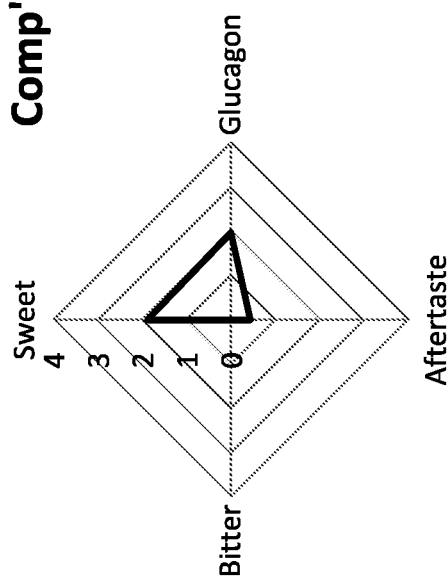

FIGS. 26A-26B are radar graphs depicting the level of activation of the sweet, aftertaste, bitter, and glucagon receptors for samples containing a *stevia* blend and one or more compounds disclosed herein.

Figure 27A:
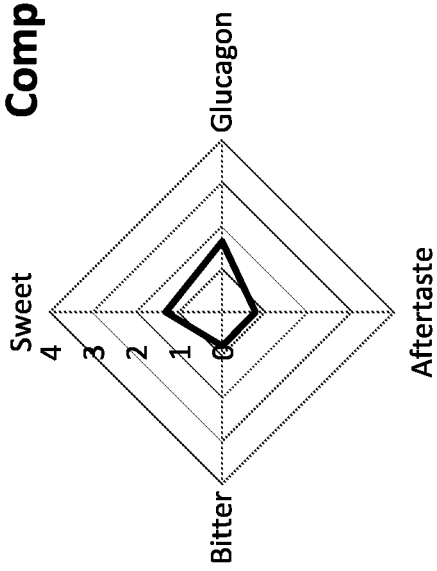
Figure 27B:
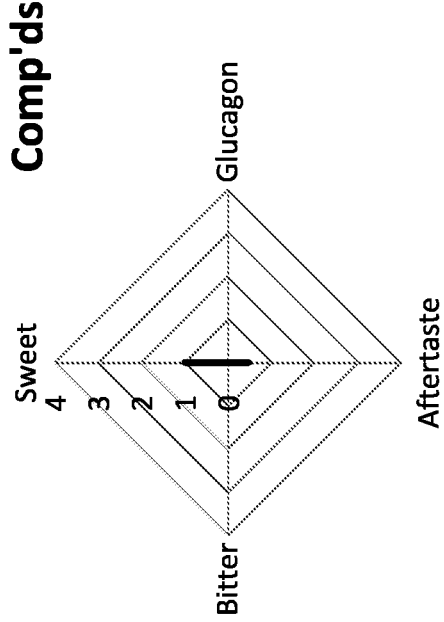

FIGS. 27A-27B are radar graphs depicting the level of activation of the sweet, aftertaste, bitter, and glucagon receptors for samples containing a *stevia* blend and one or more compounds disclosed herein.

Figure 28A:
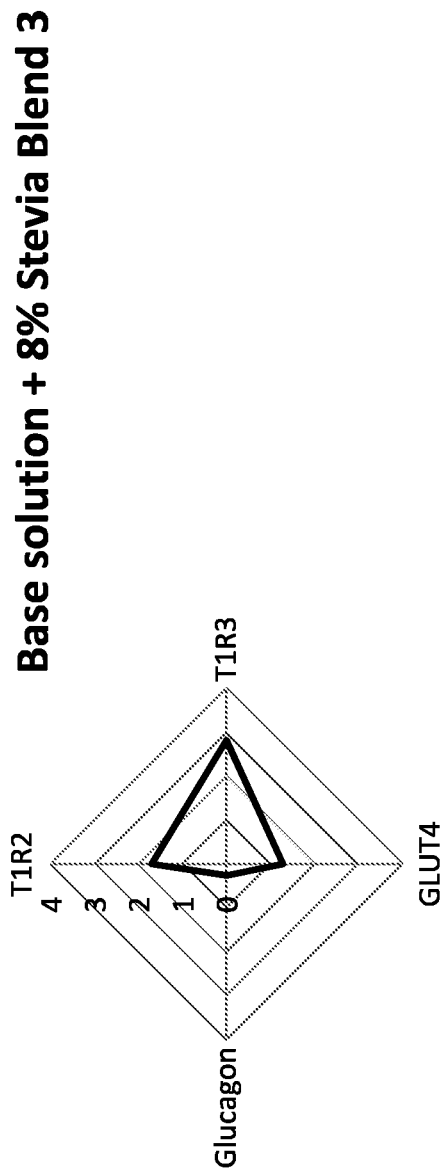
Figure 28B:
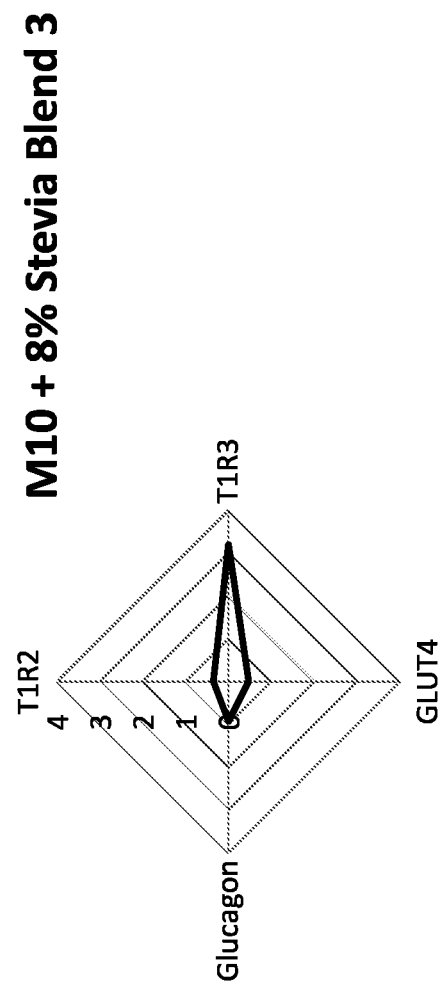

FIGS. 28A-28B are radar graphs depicting the level of activation of the T1R2, T1R3, GLUT4, and glucagon receptors for a sample containing a *stevia* blend and a sample containing a *stevia* blend and one or more compounds disclosed herein.

Figure 29A:
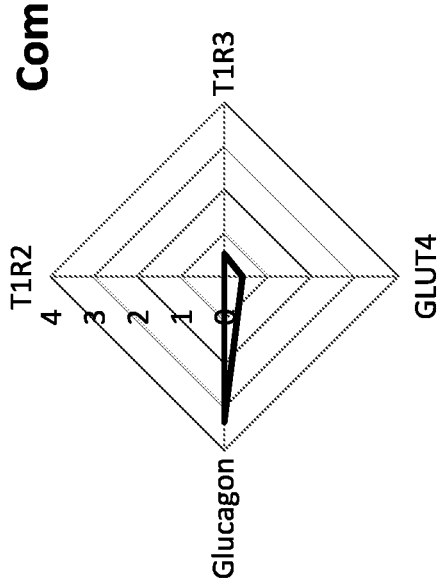
Figure 29B:
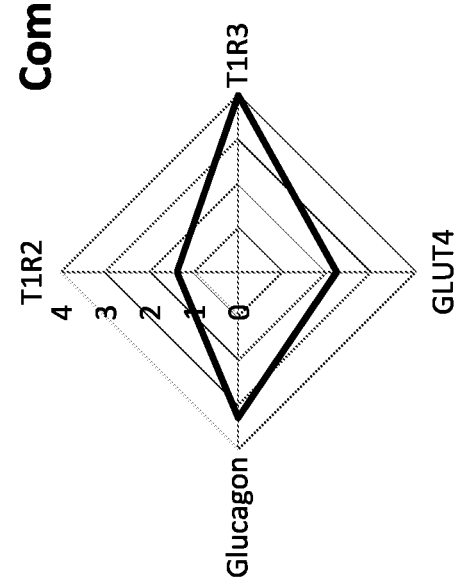

FIGS. 29A-29B are radar graphs depicting the level of activation of the T1R2, T1R3, GLUT4, and glucagon receptors for samples containing a *stevia* blend and one or more compounds disclosed herein.

Figure 30A:
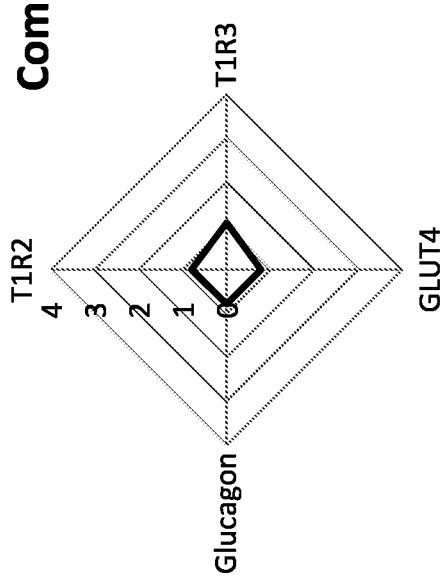
Figure 30B:
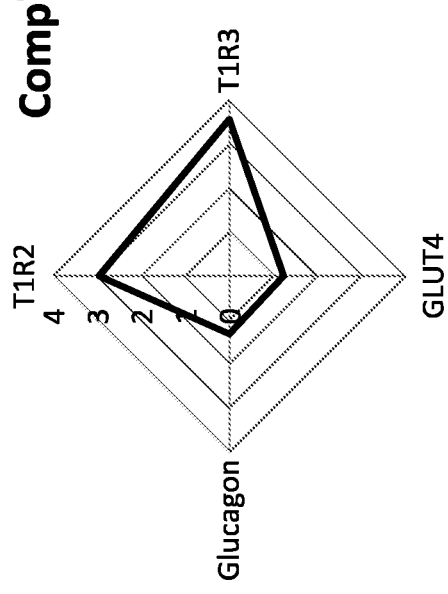

FIGS. 30A-30B are radar graphs depicting the level of activation of the T1R2, T1R3, GLUT4, and glucagon receptors for samples containing a *stevia* blend and one or more compounds disclosed herein.

Figure 31A:
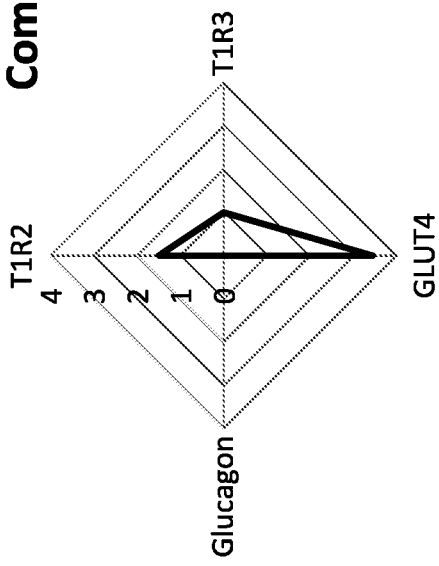
Figure 31B:
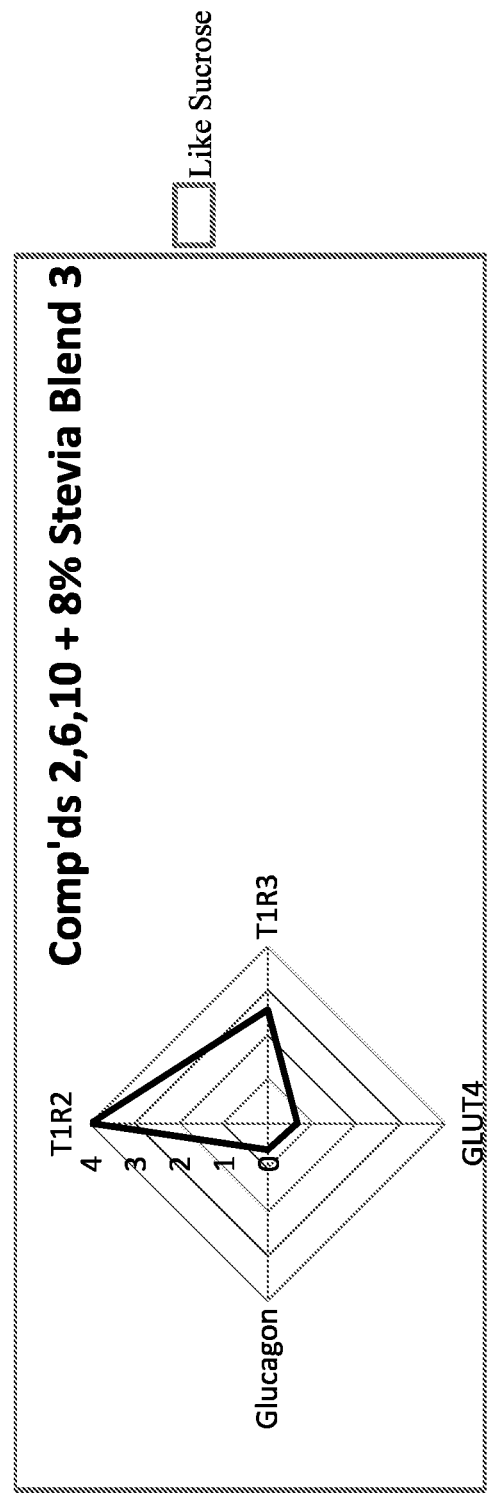

FIGS. 31A-31B are radar graphs depicting the level of activation of the T1R2, T1R3, GLUT4, and glucagon receptors for samples containing a *stevia* blend and one or more compounds disclosed herein.

Figure 32A:
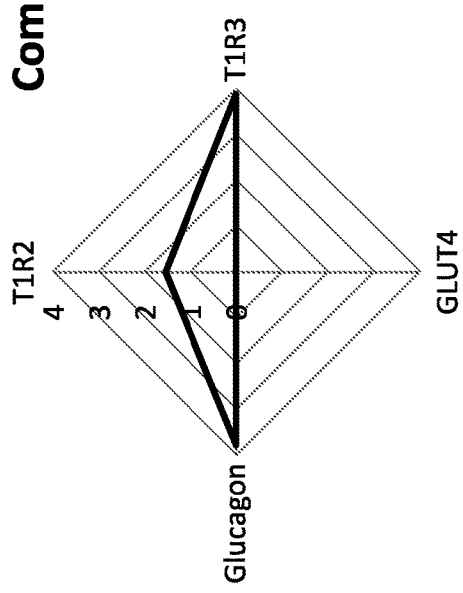
Figure 32B:
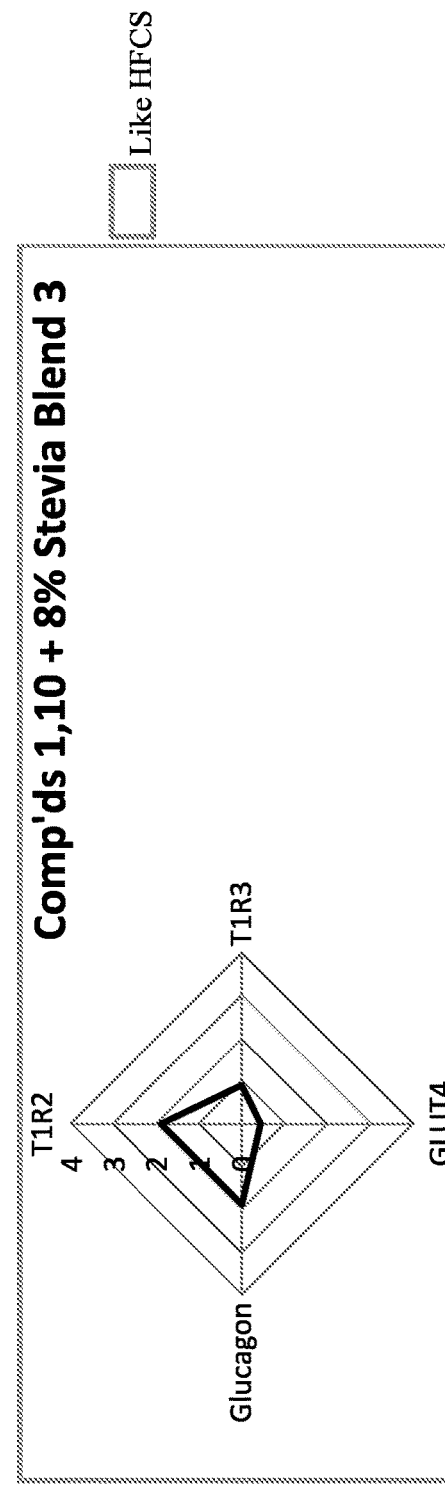

FIGS. 32A-32B are radar graphs depicting the level of activation of the T1R2, T1R3, GLUT4, and glucagon receptors for samples containing a *stevia* blend and one or more compounds disclosed herein.

Figure 33:
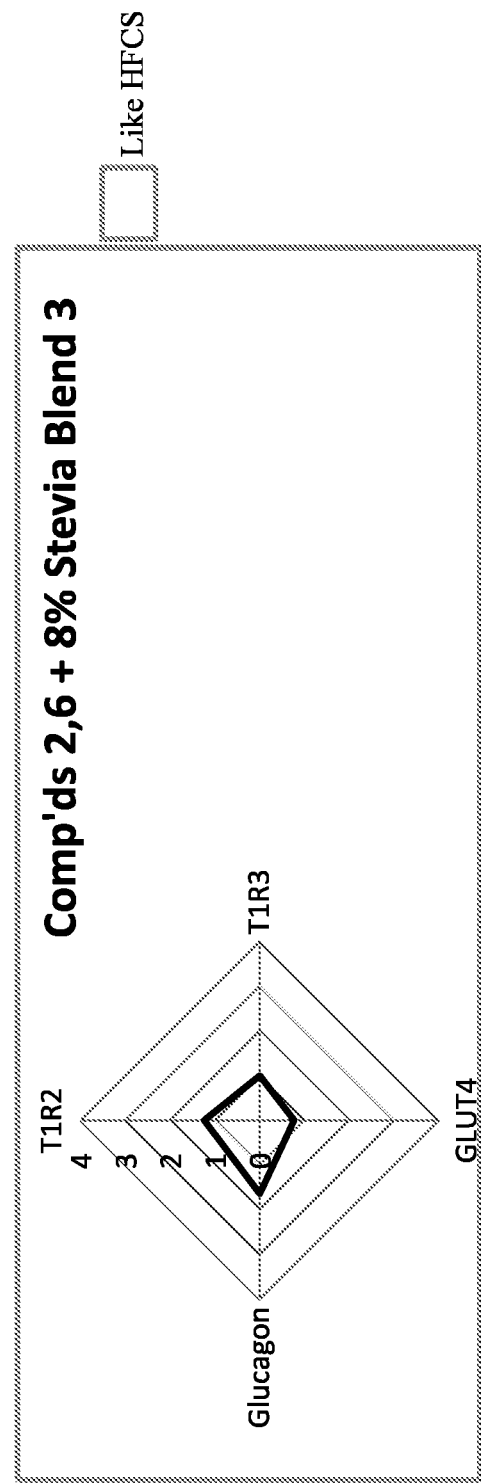

FIG. 33 is a radar graph depicting the level of activation of the T1R2, T1R3, GLUT4, and glucagon receptors for samples containing a *stevia* blend and one or more compounds disclosed herein.

Figure 34:
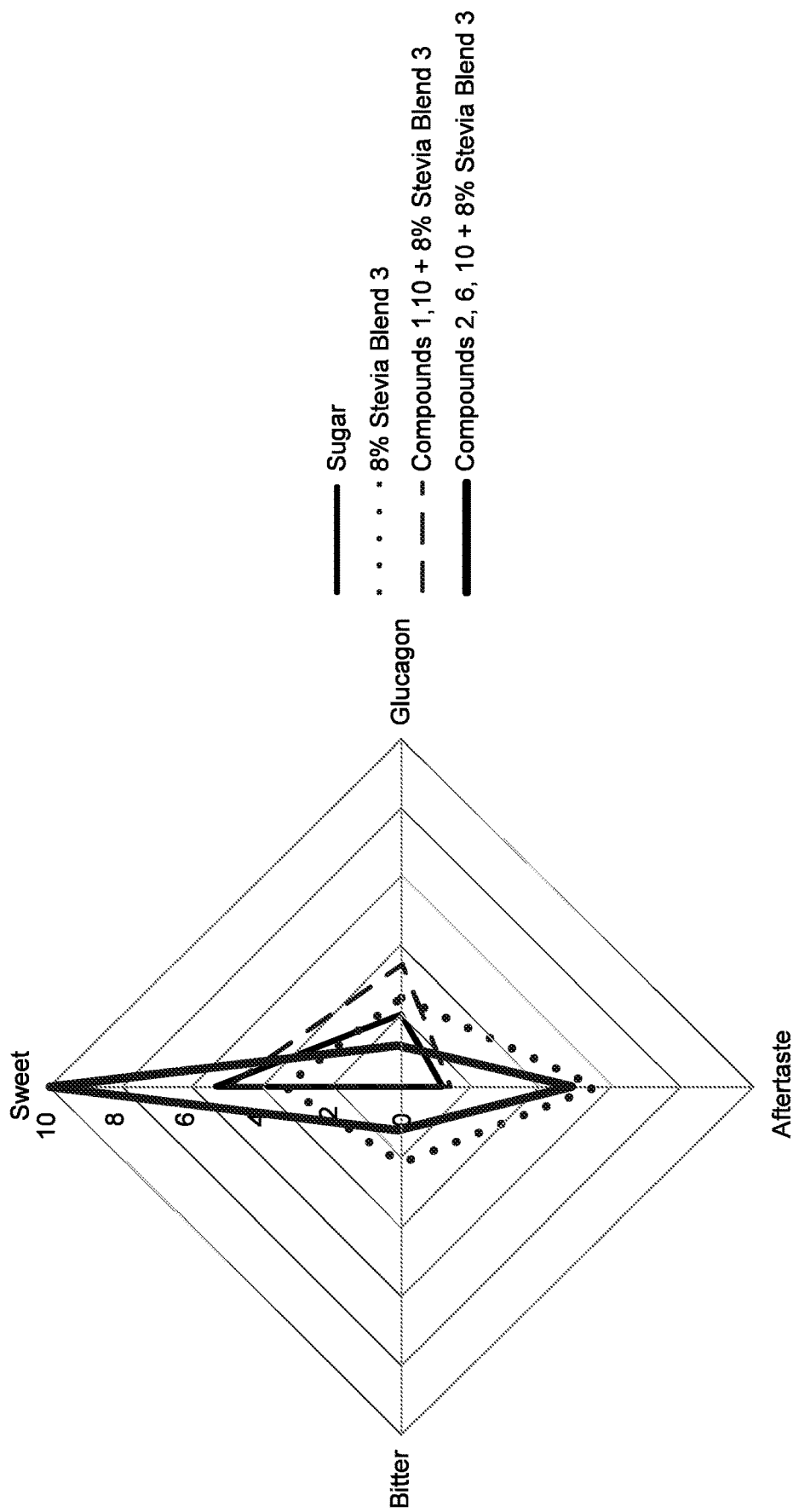

FIG. 34 is a radar graph depicting the level of activation of the sweet, aftertaste, bitter, and glucagon receptors for a sample containing sugar, a sample containing a *stevia* blend, and two samples containing a *stevia* blend with one or more compounds disclosed herein.

FIG. 35 is table listing the level of activation of the sweet, aftertaste, bitter, and glucagon receptors for samples containing a *stevia* blend and one or more compounds disclosed herein.

Figure 36:
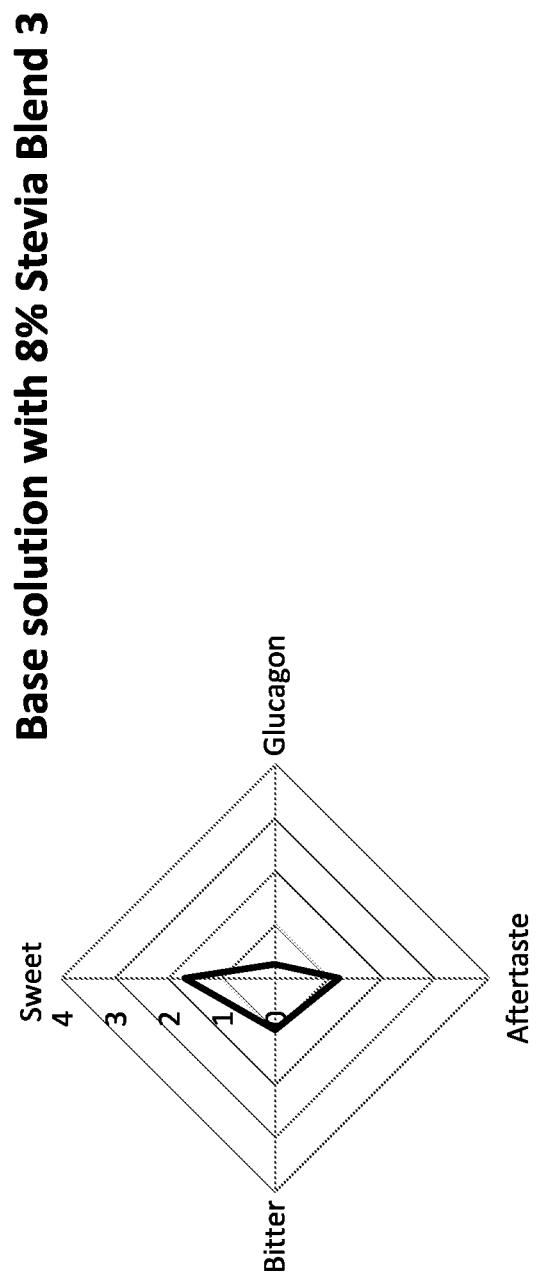

FIG. 36 is a radar graph depicting the level of activation of the sweet, aftertaste, bitter, and glucagon receptors for a sample containing a *stevia* blend.

Figure 37A:
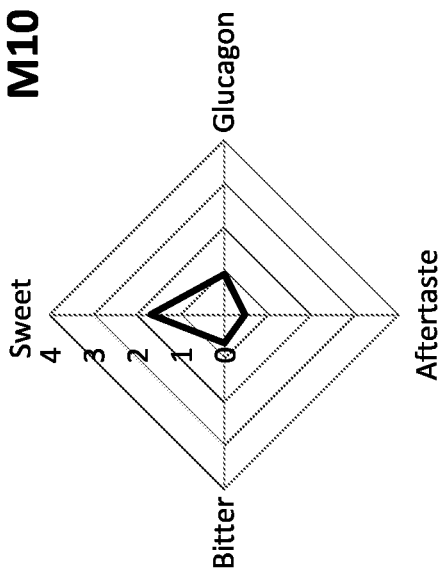
Figure 37B:
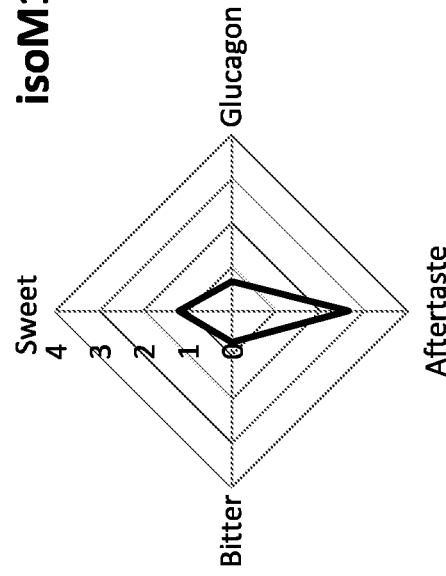

FIGS. 37A-37B are radar graphs depicting the level of activation of the sweet, aftertaste, bitter, and glucagon receptors for samples containing a *stevia* blend and one or more compounds disclosed herein.

Figure 38A:
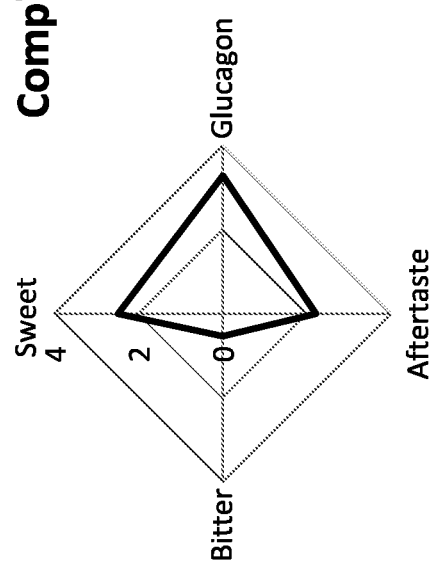
Figure 38B:
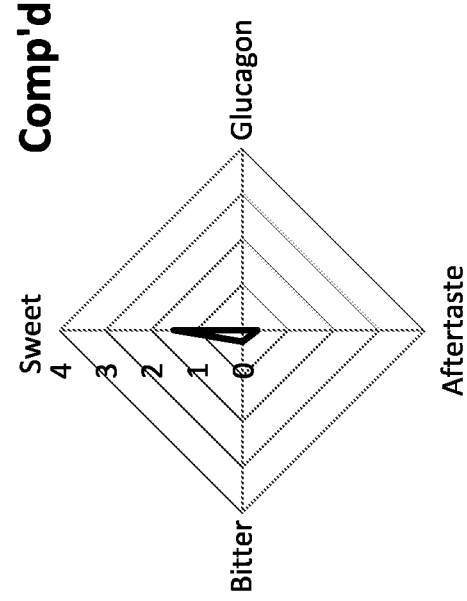

FIGS. 38A-38B are radar graphs depicting the level of activation of the sweet, aftertaste, bitter, and glucagon receptors for samples containing a *stevia* blend and one or more compounds disclosed herein.

Figure 39A:
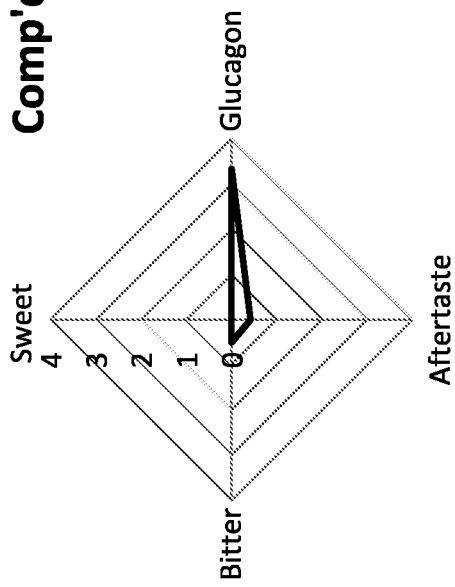
Figure 39B:
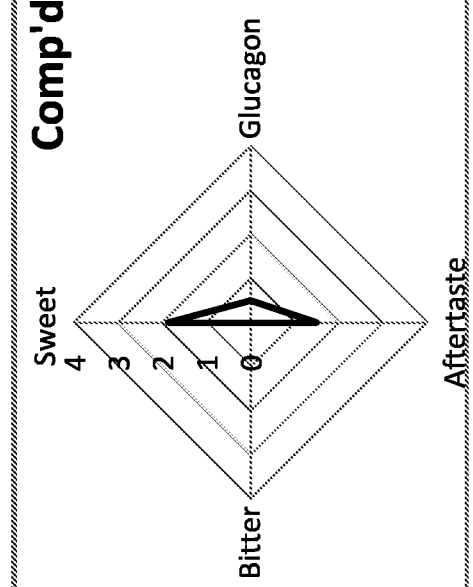

FIGS. 39A-39B are radar graphs depicting the level of activation of the sweet, aftertaste, bitter, and glucagon receptors for samples containing a *stevia* blend and one or more compounds disclosed herein.

Figure 40A:
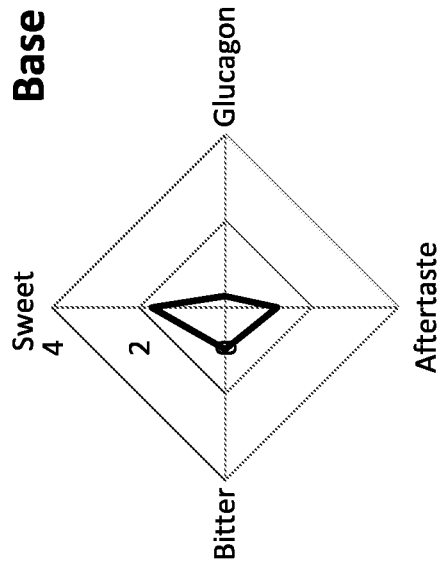
Figure 40B:
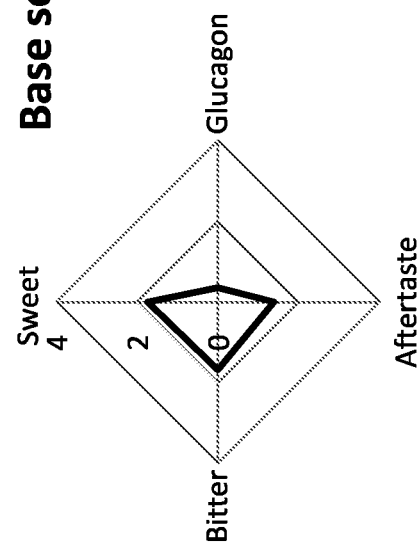

FIGS. 40A-40B are radar graphs depicting the level of activation of the sweet, aftertaste, bitter, and glucagon receptors for samples containing a *stevia* blend.

Figure 41A:
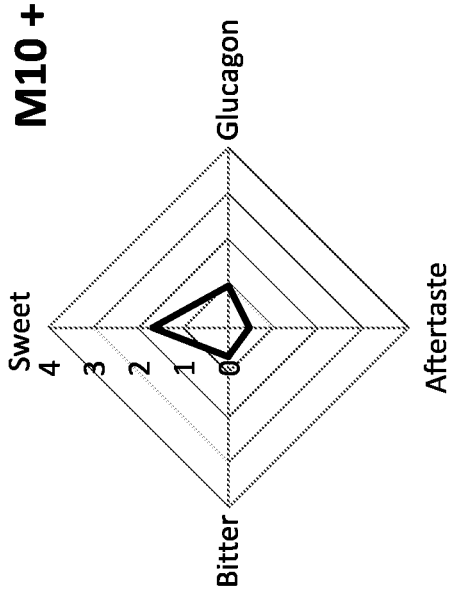
Figure 41B:
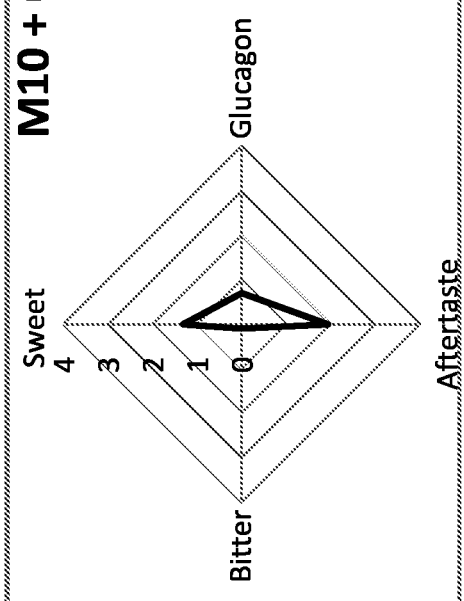

FIGS. 41A-41B are radar graphs depicting the level of activation of the sweet, aftertaste, bitter, and glucagon receptors for samples containing a *stevia* blend and one or more compounds disclosed herein.

Figure 42A:
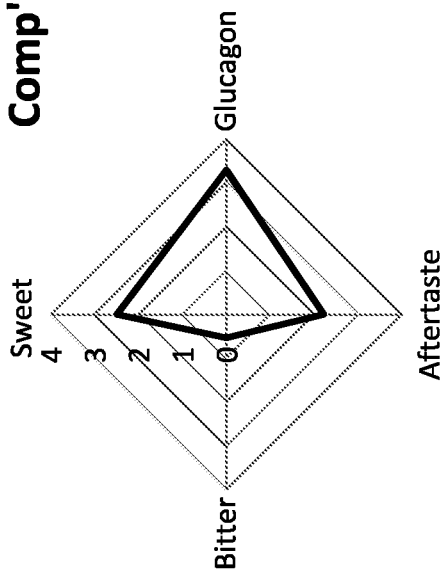
Figure 42B:
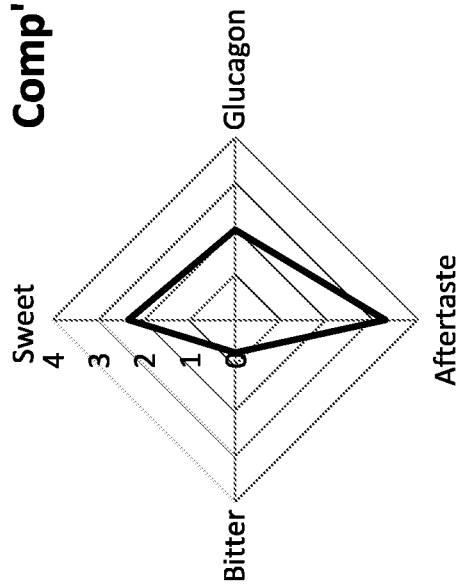

FIGS. 42A-42B are radar graphs depicting the level of activation of the sweet, aftertaste, bitter, and glucagon receptors for samples containing a *stevia* blend and one or more compounds disclosed herein.

Figure 43A:
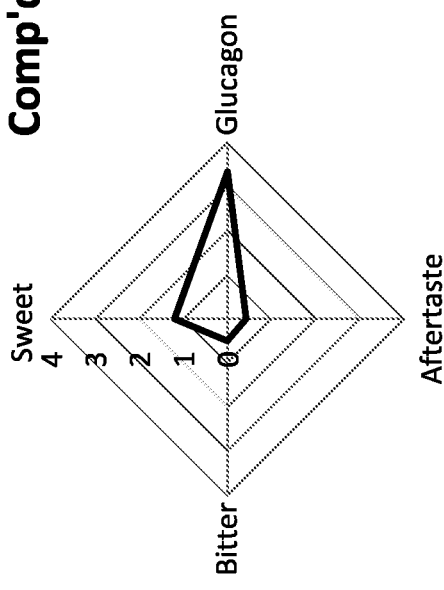
Figure 43B:
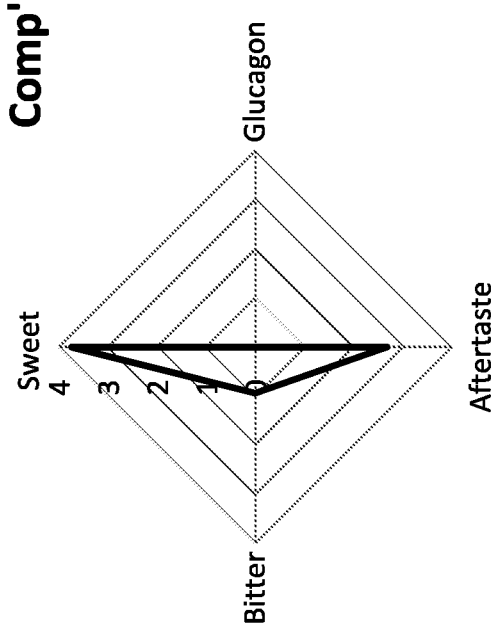

FIGS. 43A-43B are radar graphs depicting the level of activation of the sweet, aftertaste, bitter, and glucagon receptors for samples containing a *stevia* blend and one or more compounds disclosed herein.

Figure 44A:
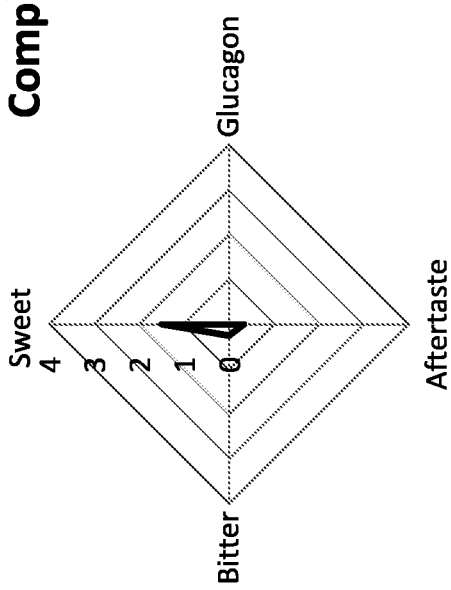
Figure 44B:
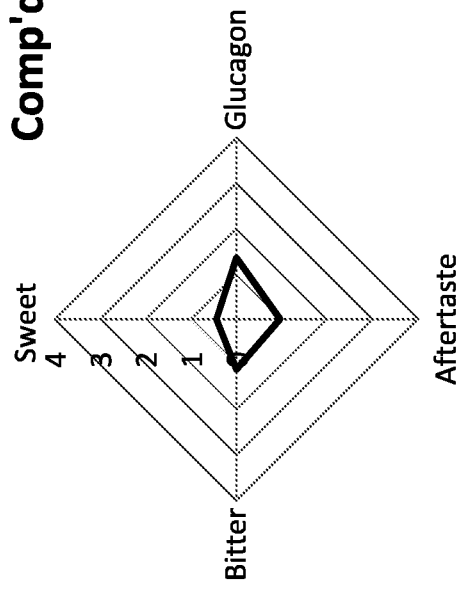

FIGS. 44A-44B are radar graphs depicting the level of activation of the sweet, aftertaste, bitter, and glucagon receptors for samples containing a *stevia* blend and one or more compounds disclosed herein.

Figure 45A:
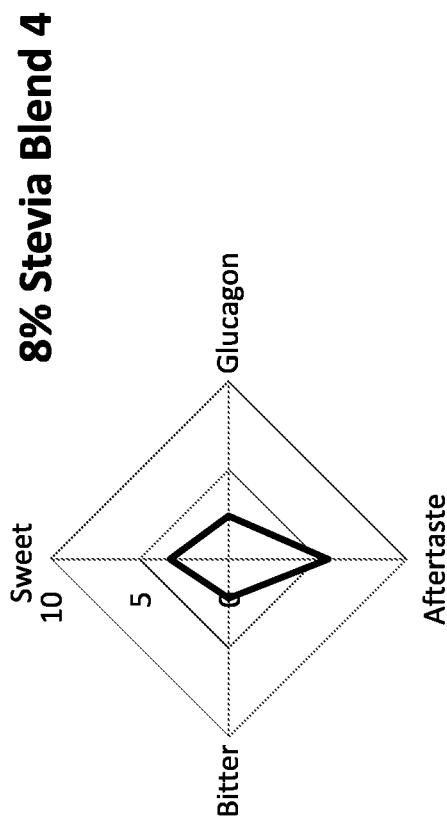
Figure 45B:
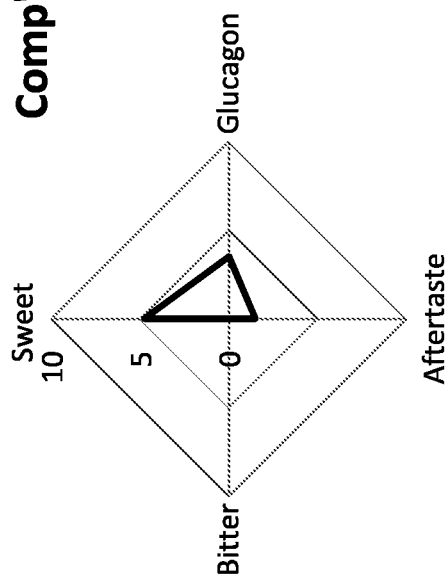

FIGS. 45A-45B are radar graphs depicting the level of activation of the sweet, aftertaste, bitter, and glucagon receptors for a sample containing a *stevia* blend and a sample containing a *stevia* blend and one or more compounds disclosed herein.

Figure 46:
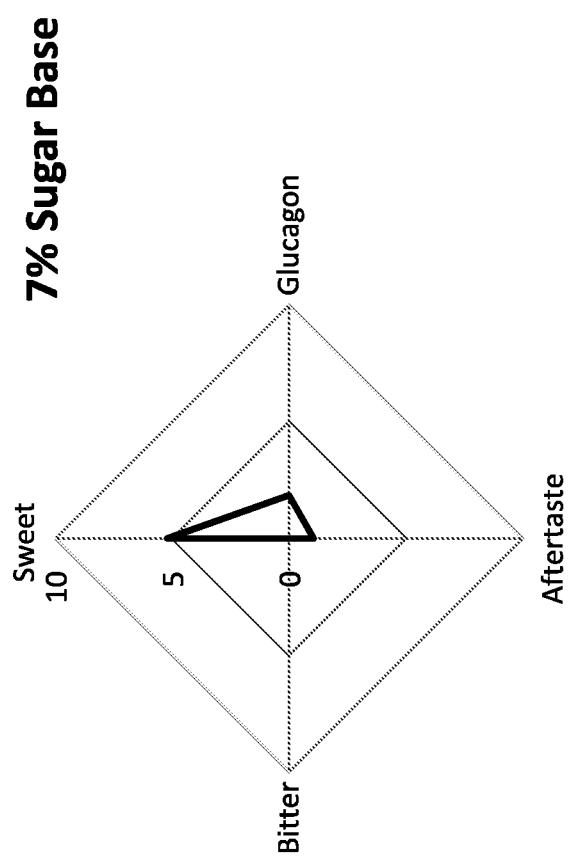

FIG. 46 is a radar graph depicting the level of activation of the sweet, aftertaste, bitter, and glucagon receptors for a sample containing sugar.

Figure 47:
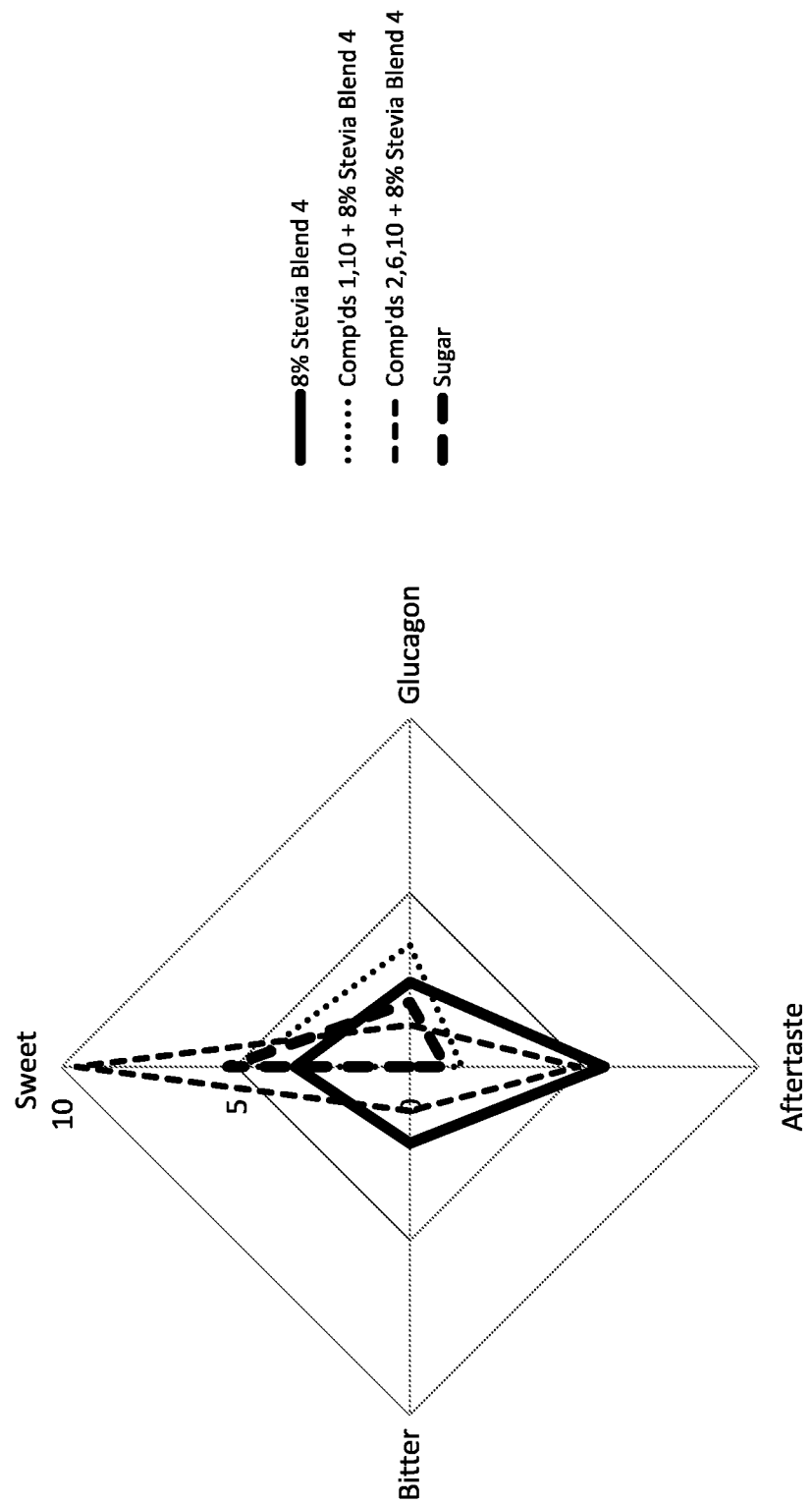

FIG. 47 is a radar graph depicting the level of activation of the sweet, aftertaste, bitter, and glucagon receptors for a sample containing a *stevia* blend, two samples containing a *stevia* blend and one or more compounds disclosed herein, and a sample containing sugar.

Figure 48:
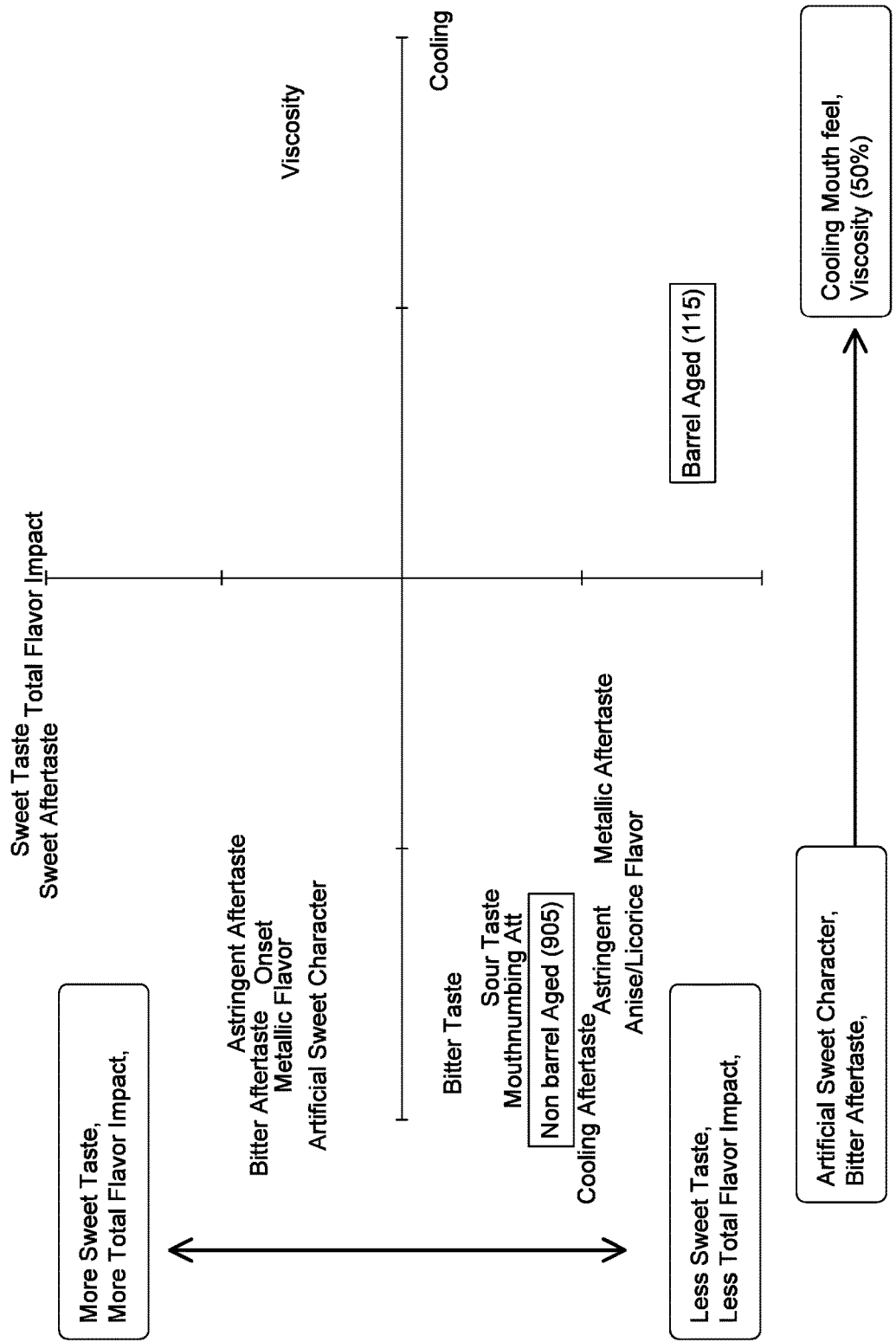

FIG. 48 is a sensory map comparing the taste profile of a barrel aged *stevia* blend and a non-barrel aged *stevia* blend.

Figure 49:
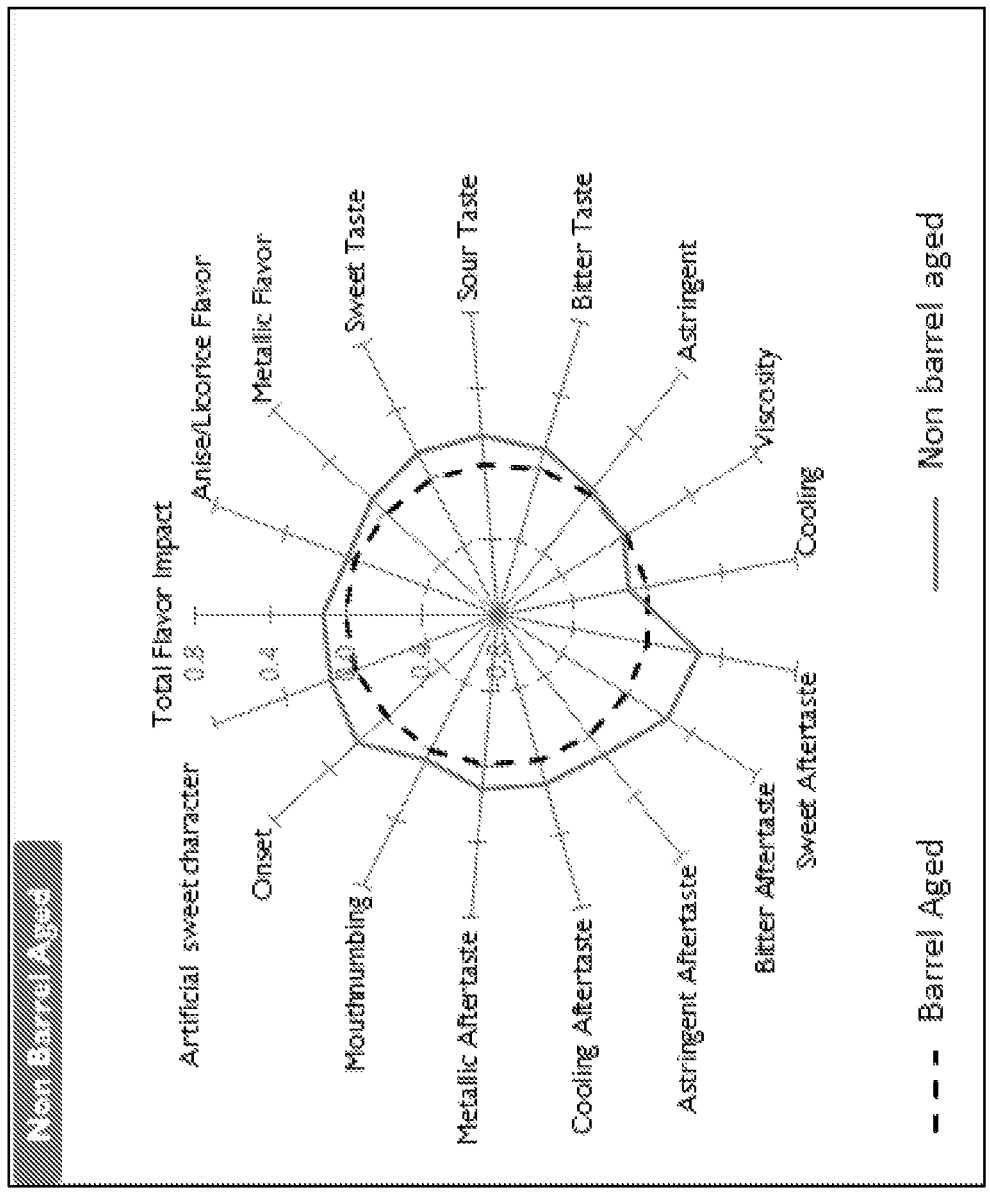

FIG. 49 is a sensory map comparing the taste profile of a barrel aged *stevia* blend and a non-barrel aged *stevia* blend.

Figure 50:
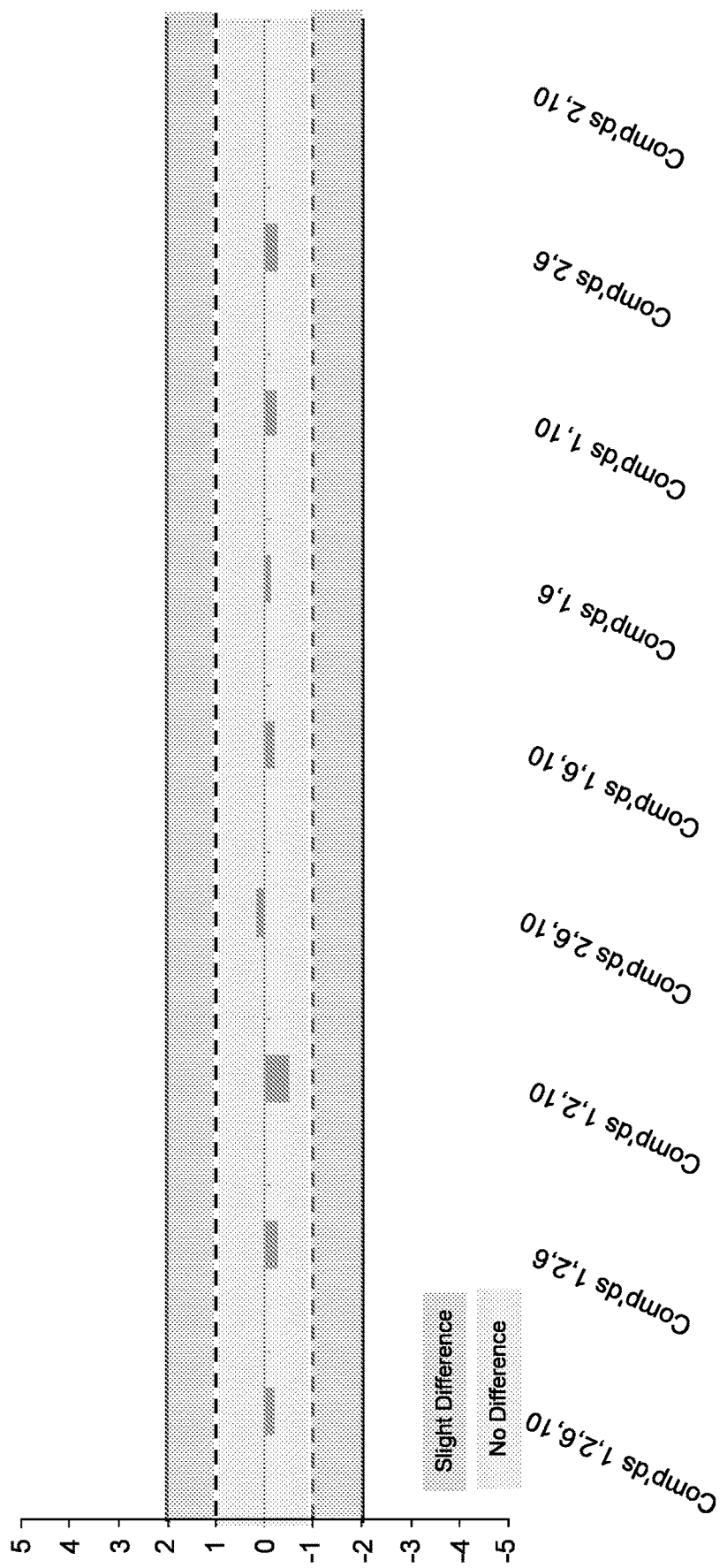

FIG. 50 is a bar graph comparing the overall liking of the taste of a barrel aged *stevia* blend and the taste of a *stevia* blend containing one or more compounds disclosed herein.

Figure 51:
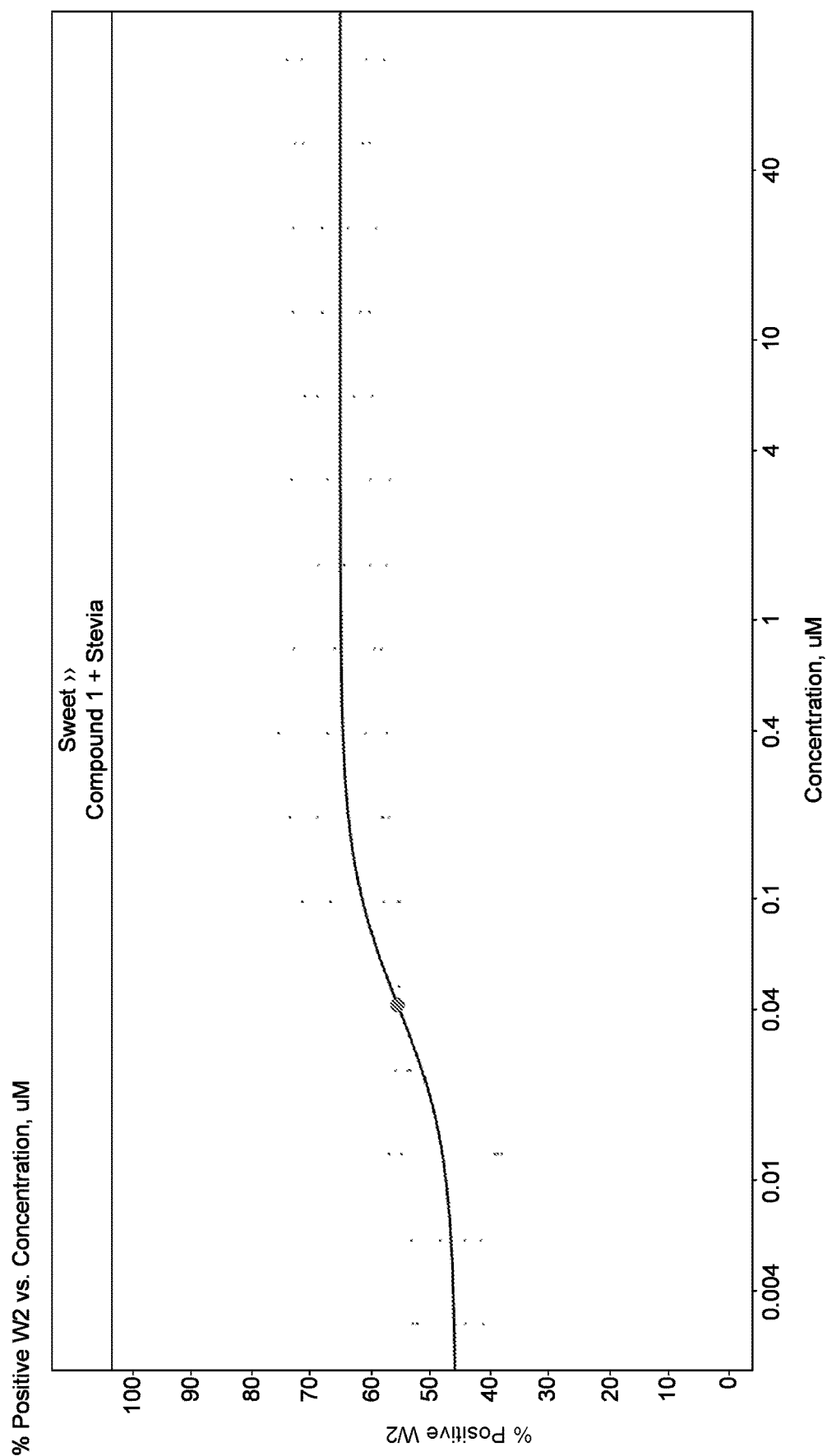

FIG. 51 is a dose response curve depicting the dose dependent level of activation of the sweet receptors by samples containing a *stevia* blend and one or more of the compounds disclosed herein.

Figure 52:
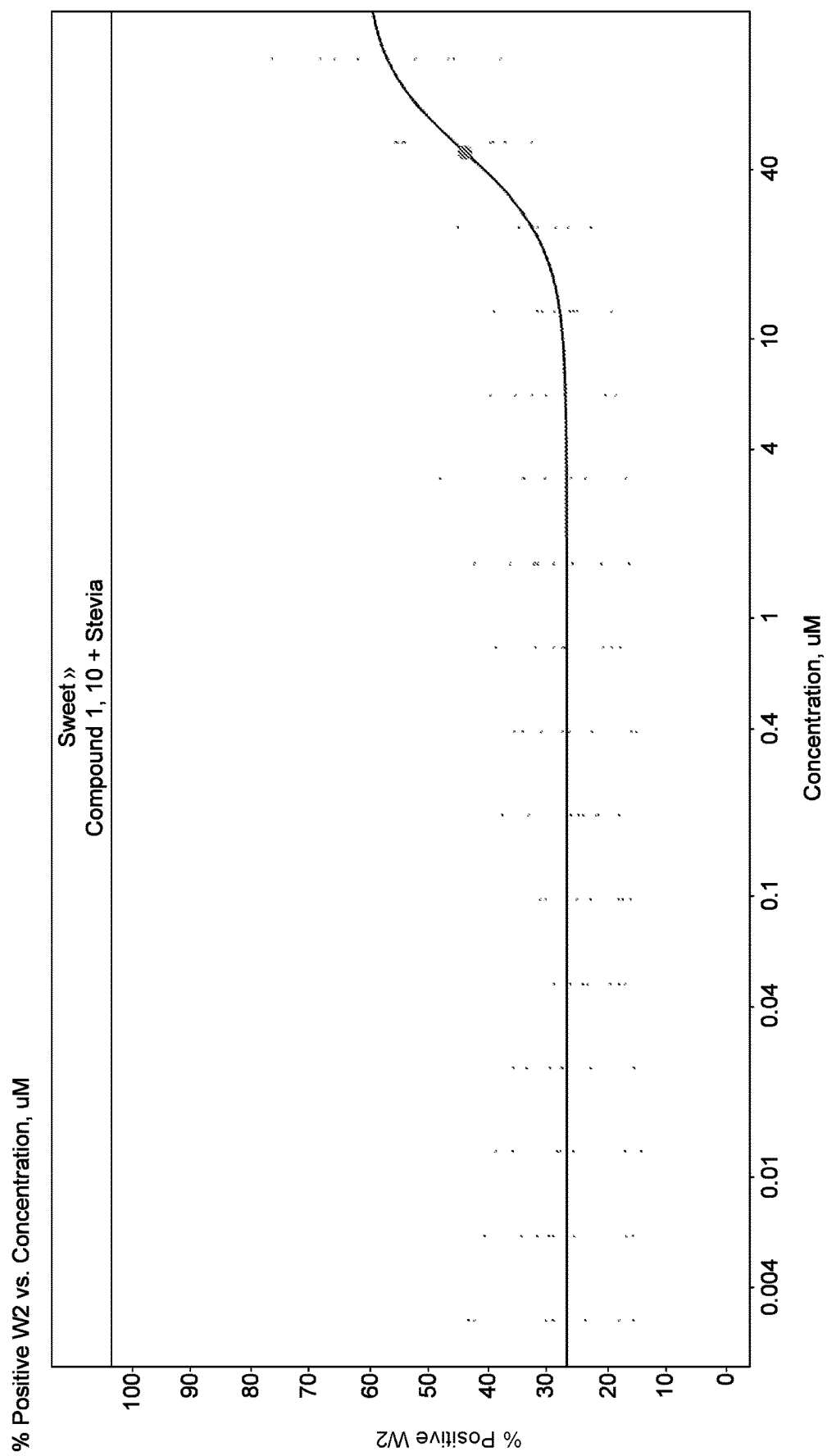

FIG. 52 is a dose response curve depicting the dose dependent level of activation of the sweet receptors by samples containing a *stevia* blend and one or more of the compounds disclosed herein.

Figure 53:
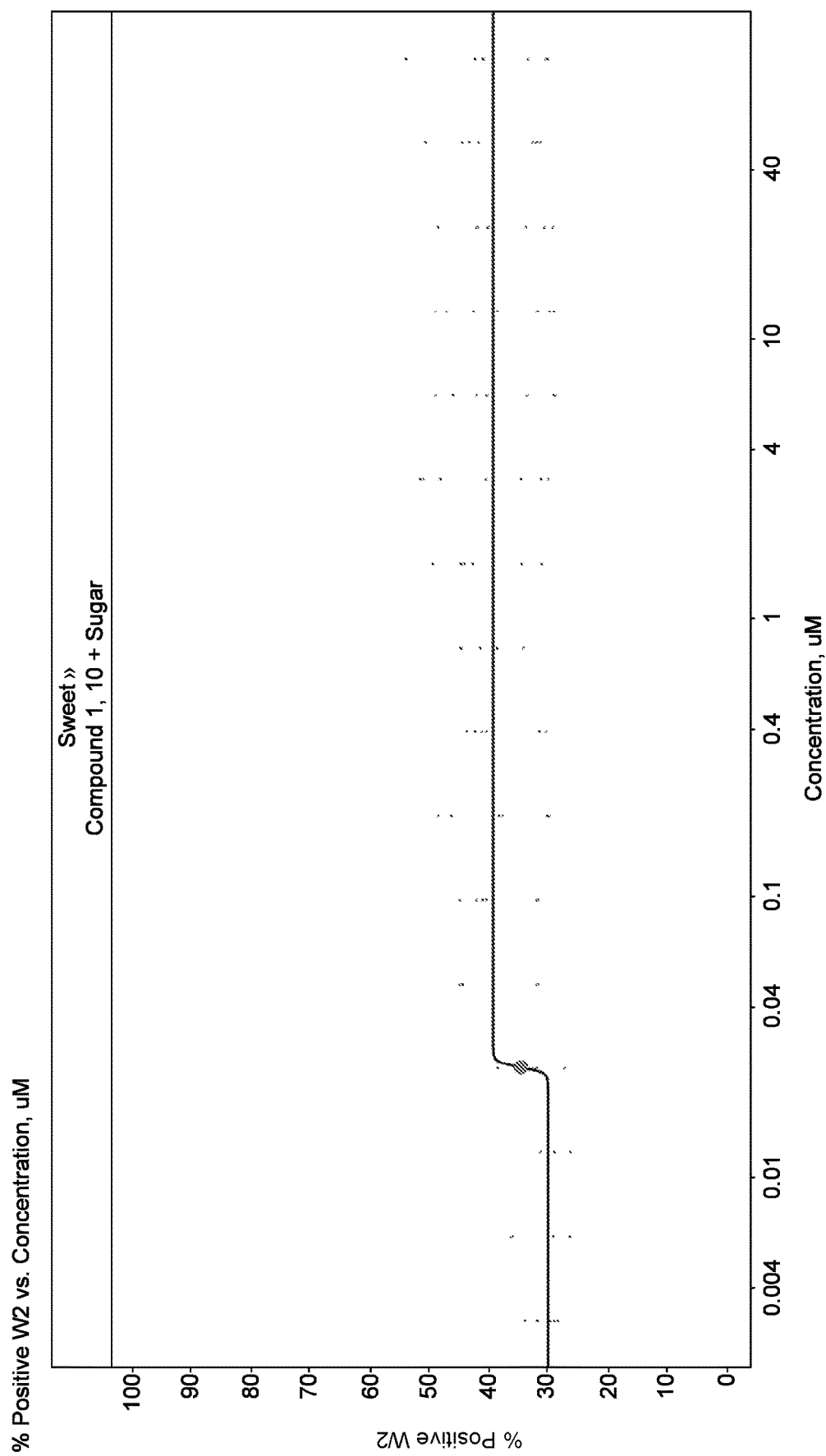

FIG. 53 is a dose response curve depicting the dose dependent level of activation of the sweet receptors by samples containing sugar and one or more of the compounds disclosed herein.

Figure 54:
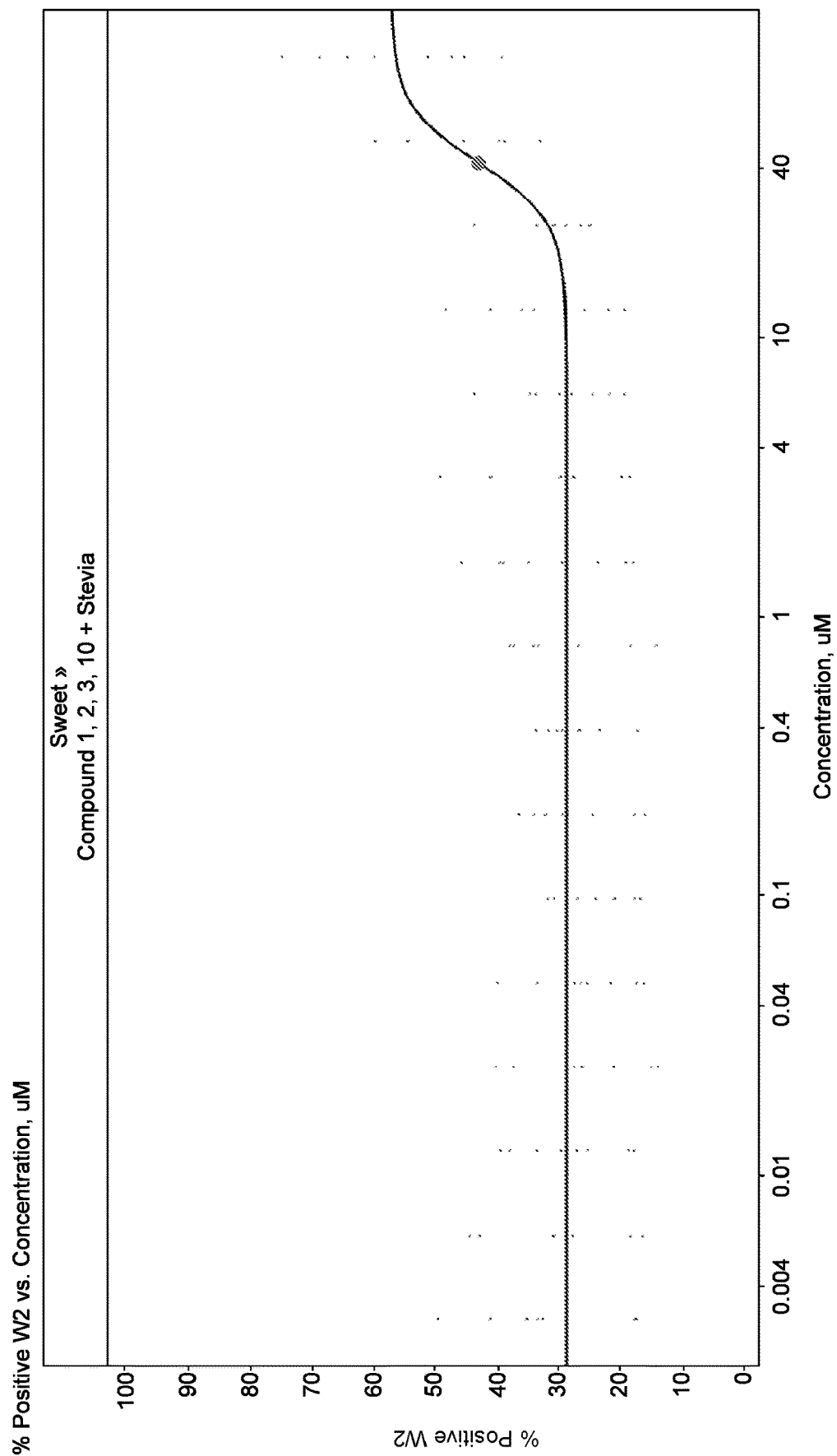

FIG. 54 is a dose response curve depicting the dose dependent level of activation of the sweet receptors by samples containing a *stevia* blend and one or more of the compounds disclosed herein.

Figure 55:
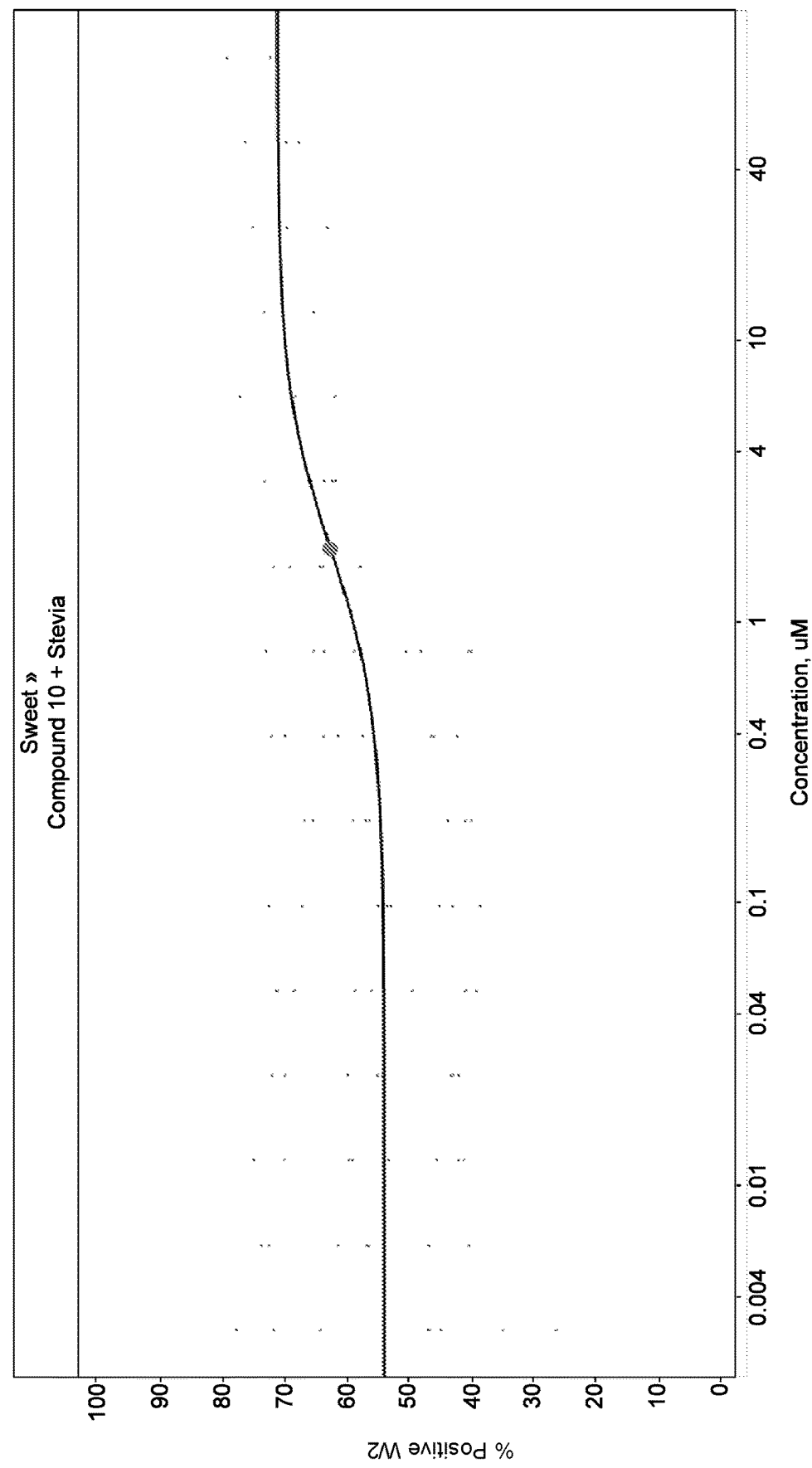

FIG. 55 is a dose response curve depicting the dose dependent level of activation of the sweet receptors by samples containing a *stevia* blend and one or more of the compounds disclosed herein.

Figure 56:
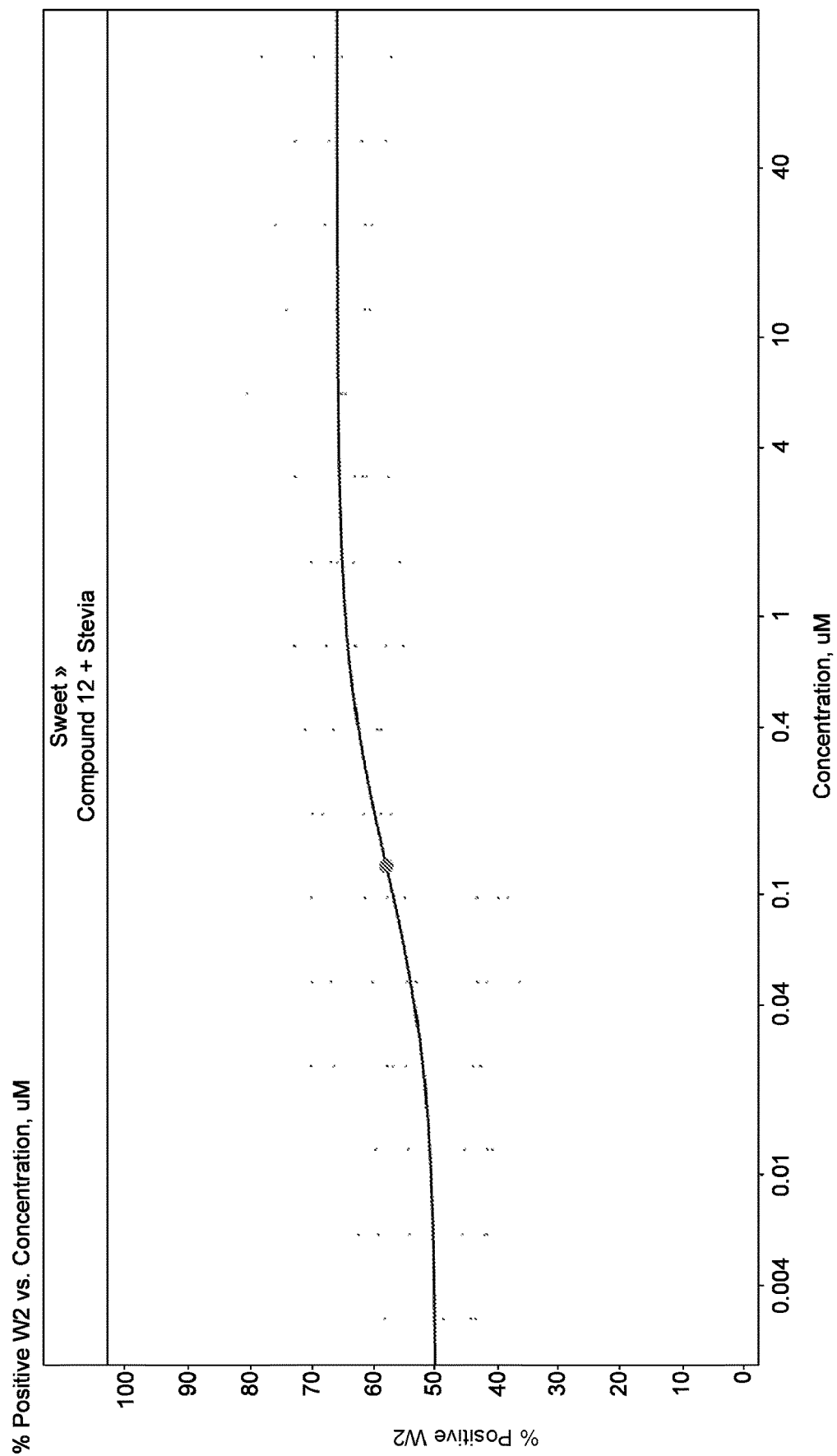

FIG. 56 is a dose response curve depicting the dose dependent level of activation of the sweet receptors by samples containing a *stevia* blend and one or more of the compounds disclosed herein.

Figure 57:
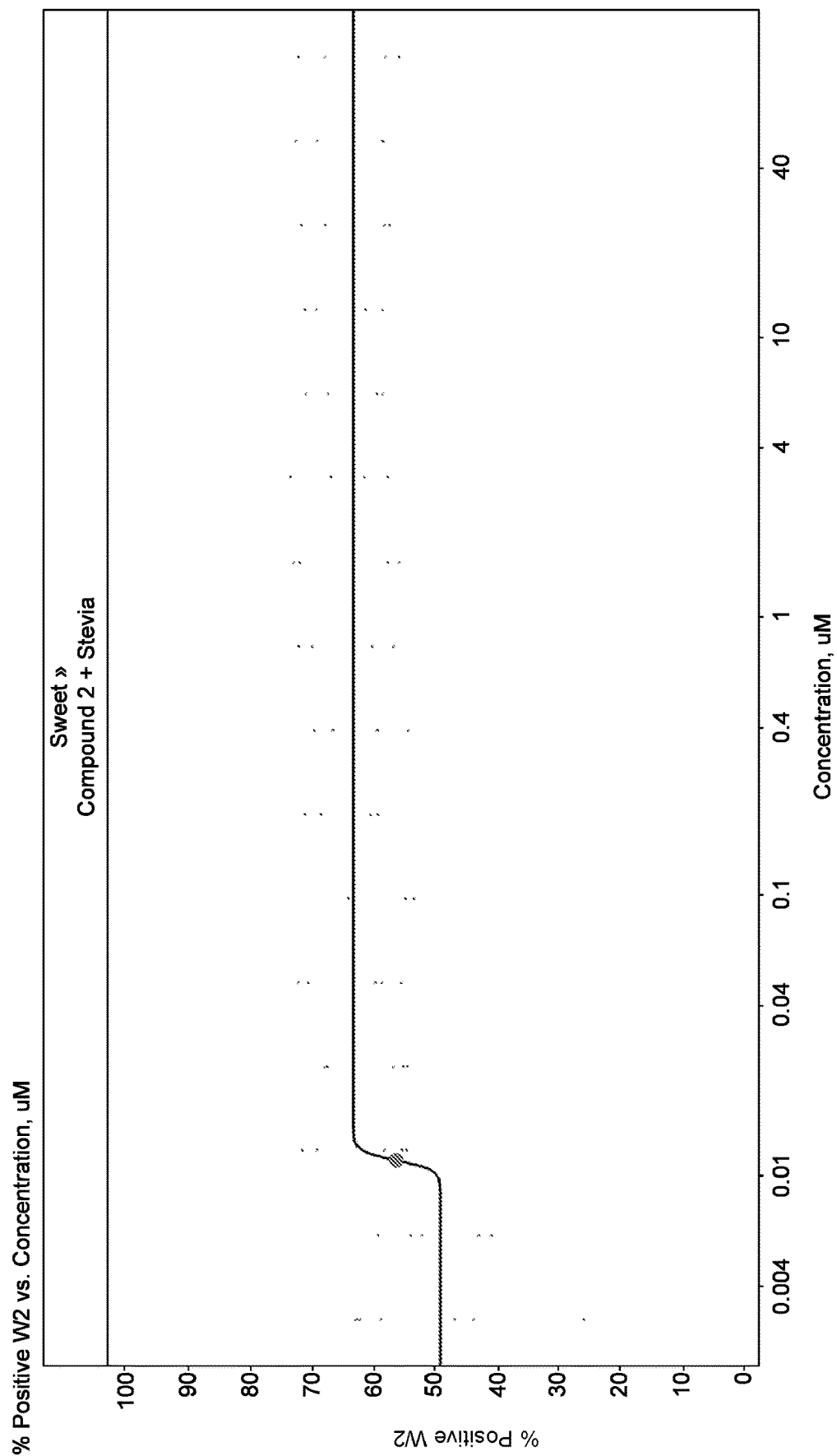

FIG. 57 is a dose response curve depicting the dose dependent level of activation of the sweet receptors by samples containing a *stevia* blend and one or more of the compounds disclosed herein.

Figure 58:
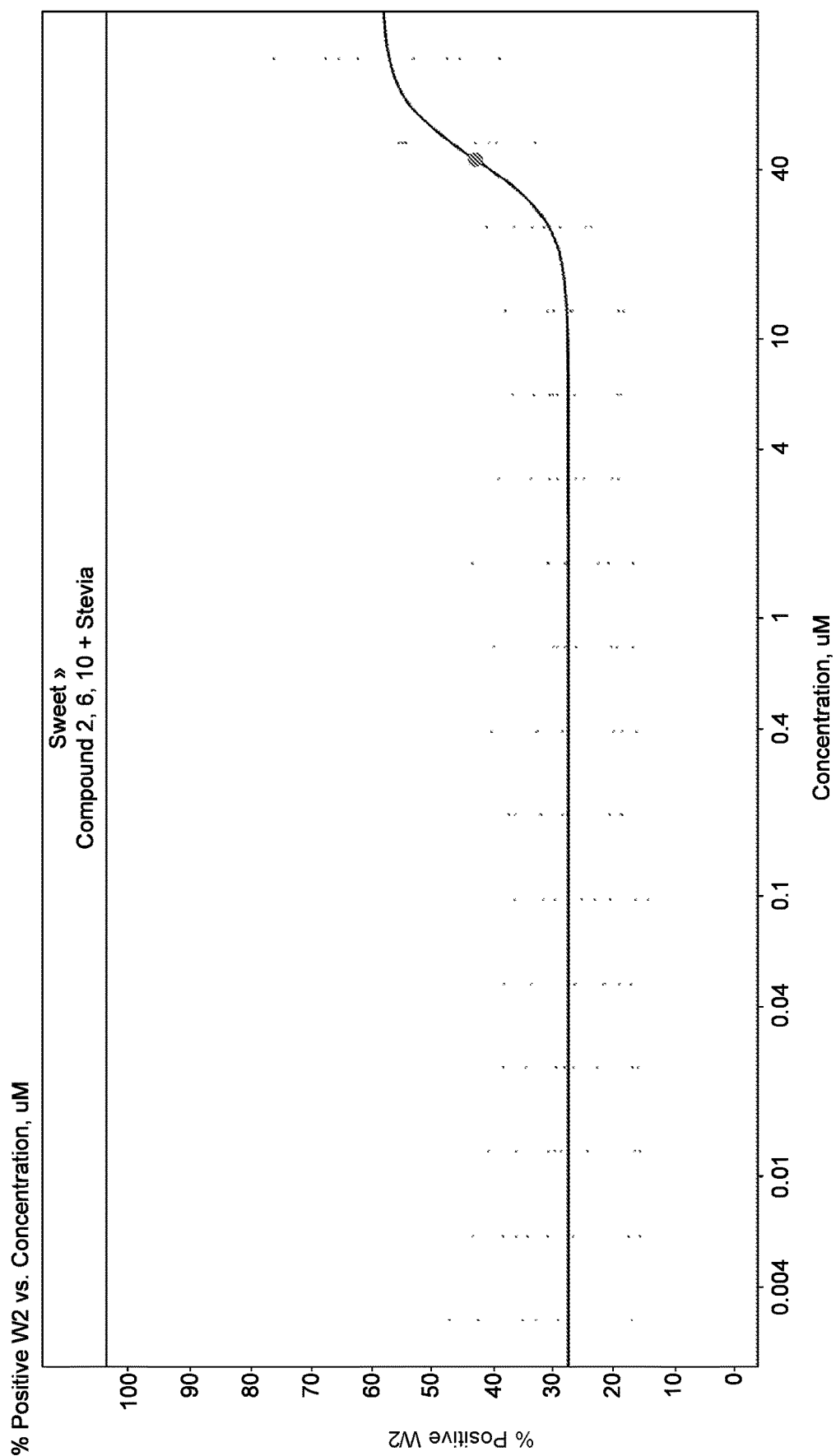

FIG. 58 is a dose response curve depicting the dose dependent level of activation of the sweet receptors by samples containing a *stevia* blend and one or more of the compounds disclosed herein.

Figure 59:
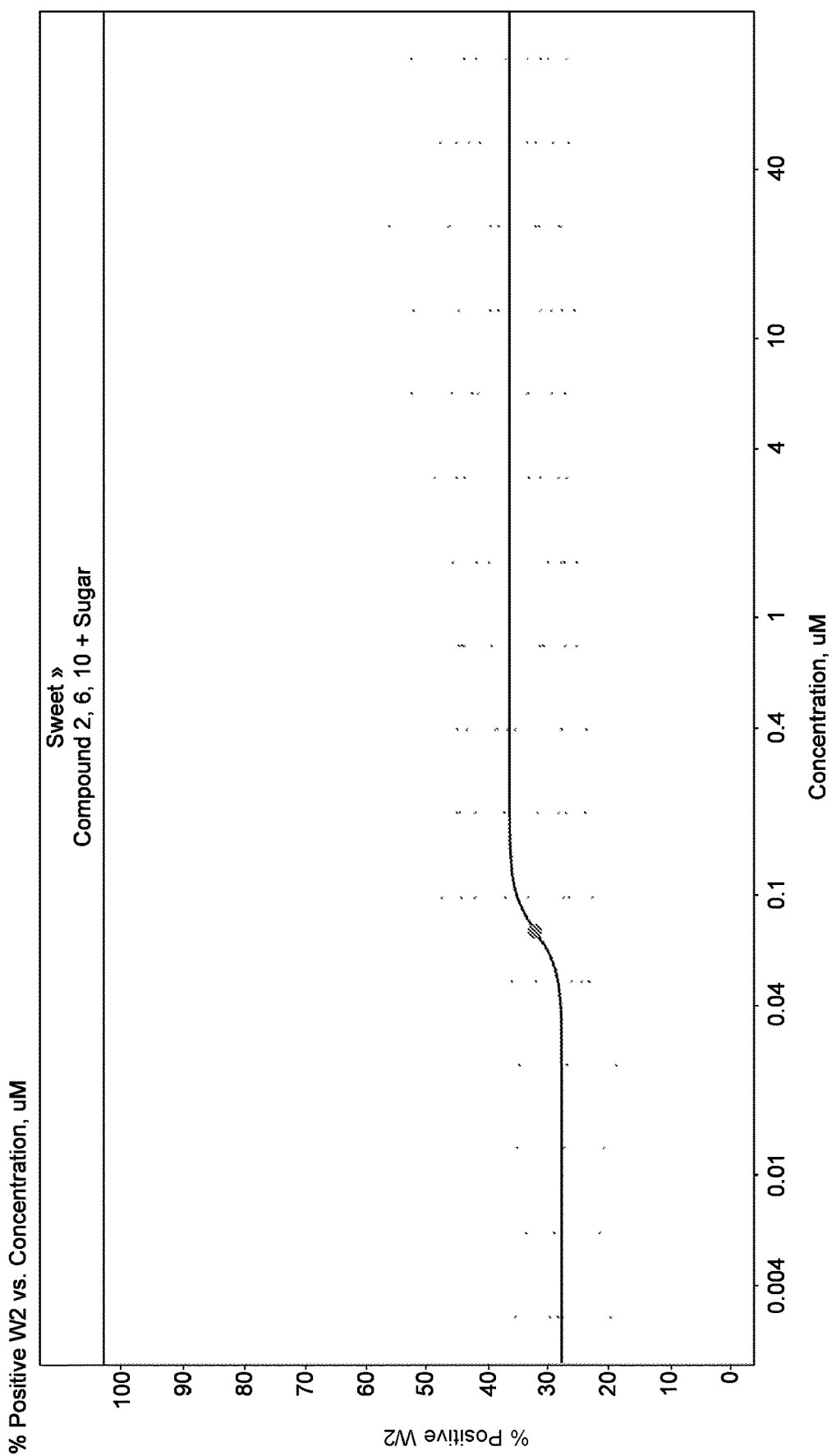

FIG. 59 is a dose response curve depicting the dose dependent level of activation of the sweet receptors by samples containing sugar and one or more of the compounds disclosed herein.

Figure 60:
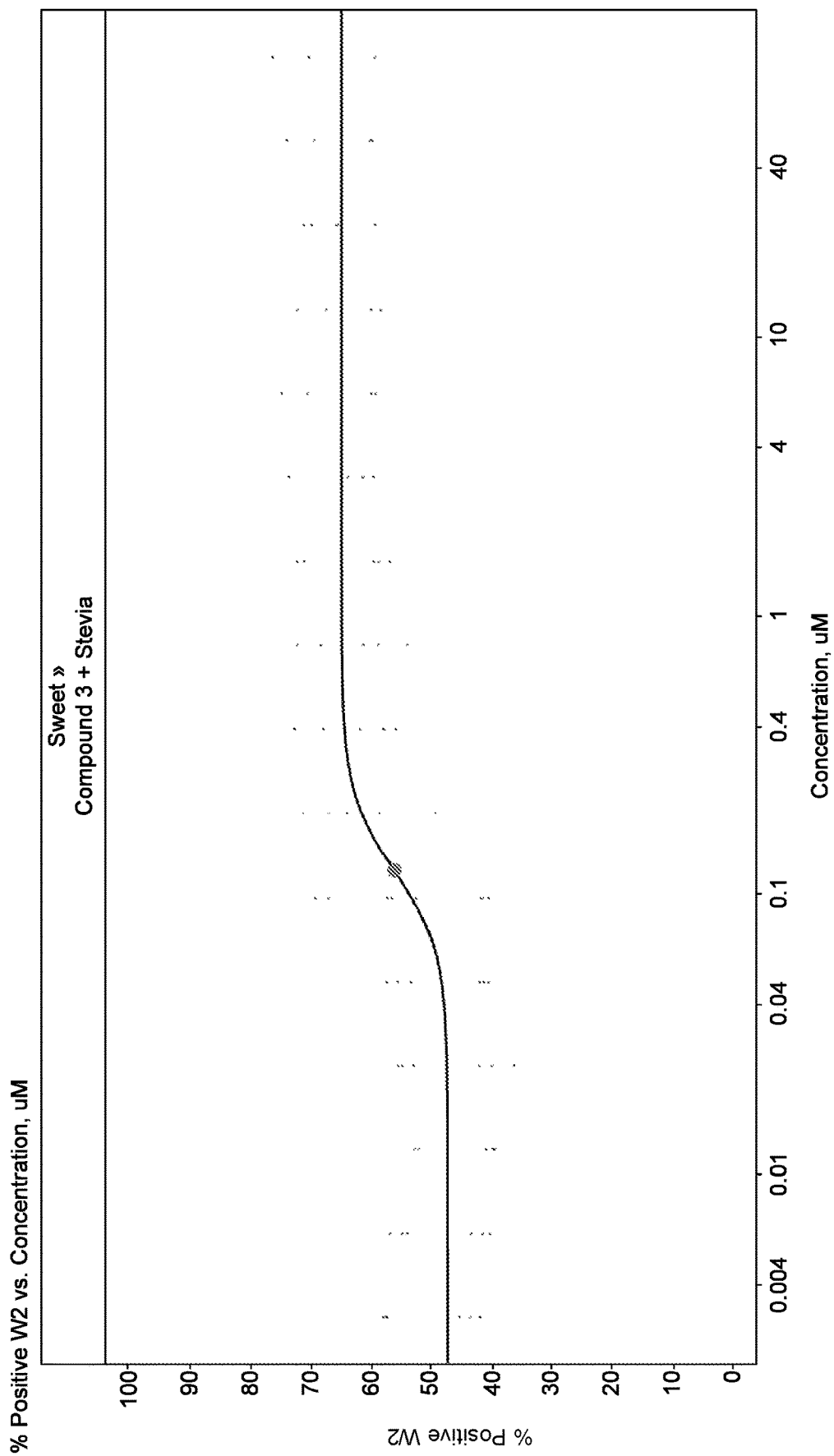

FIG. 60 is a dose response curve depicting the dose dependent level of activation of the sweet receptors by samples containing a *stevia* blend and one or more of the compounds disclosed herein.

Figure 61:
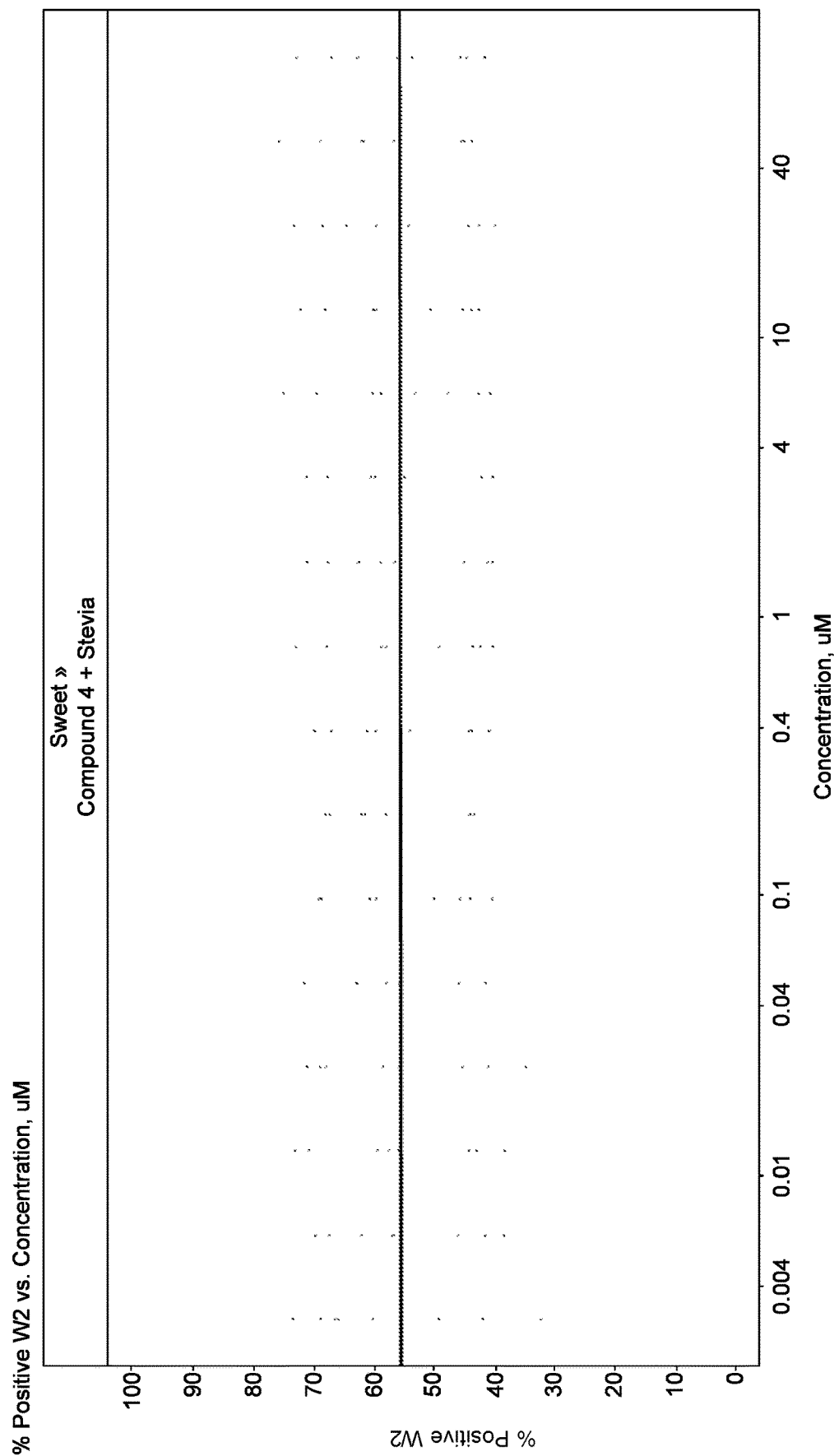

FIG. 61 is a dose response curve depicting the dose dependent level of activation of the sweet receptors by samples containing a *stevia* blend and one or more of the compounds disclosed herein.

Figure 62:
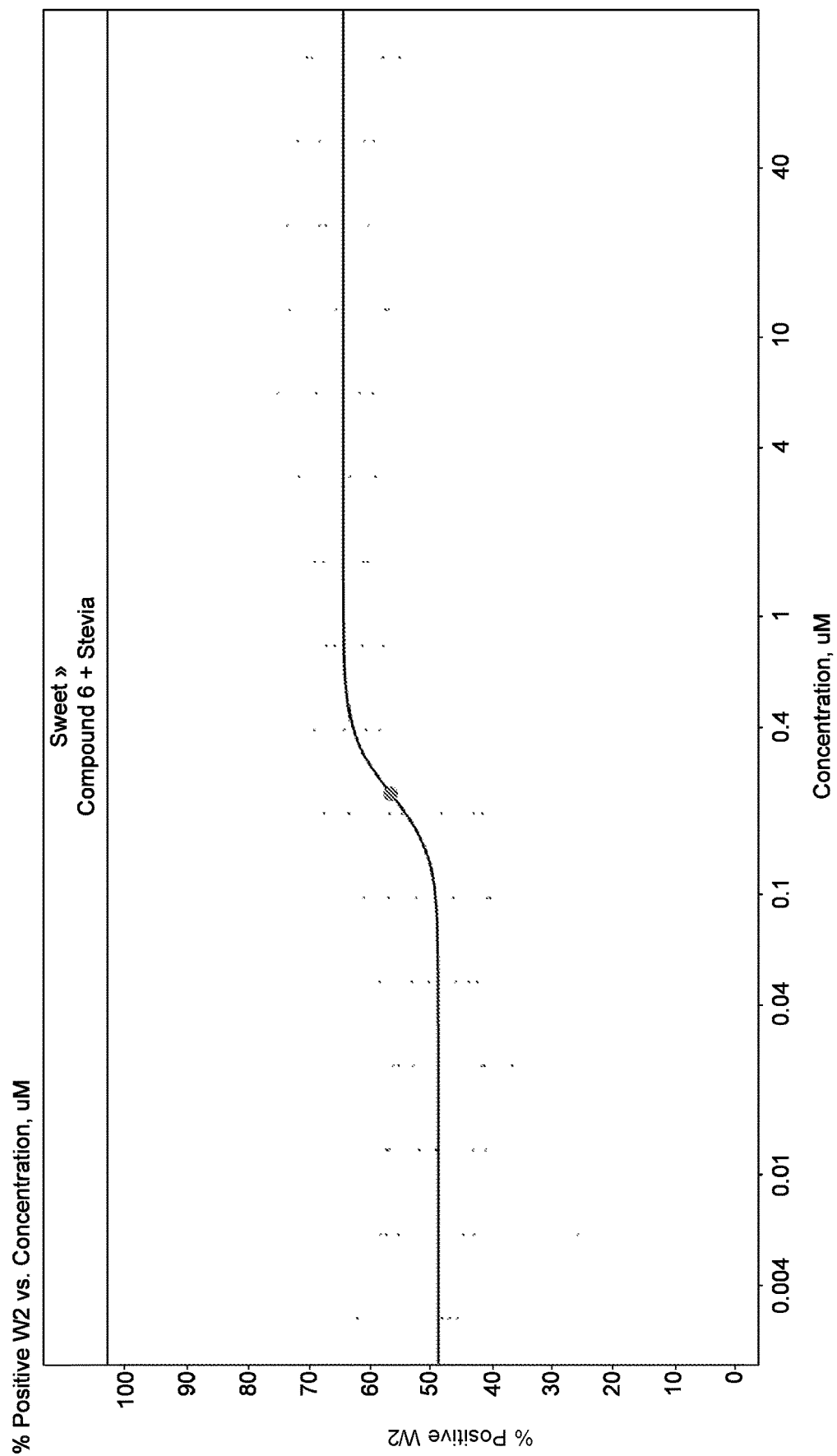

FIG. 62 is a dose response curve depicting the dose dependent level of activation of the sweet receptors by samples containing a *stevia* blend and one or more of the compounds disclosed herein.

Figure 63:
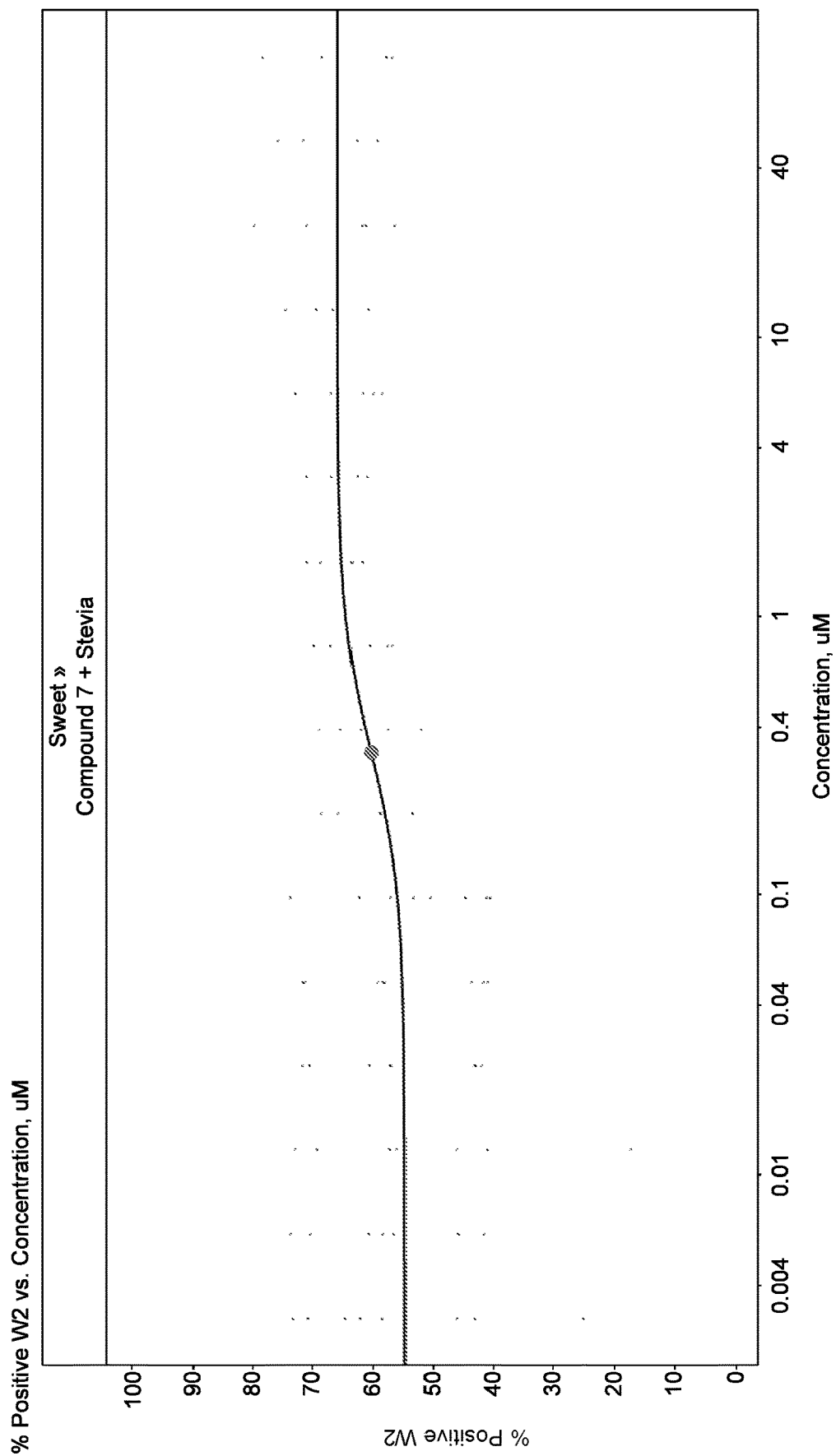

FIG. 63 is a dose response curve depicting the dose dependent level of activation of the sweet receptors by samples containing a *stevia* blend and one or more of the compounds disclosed herein.

Figure 64:
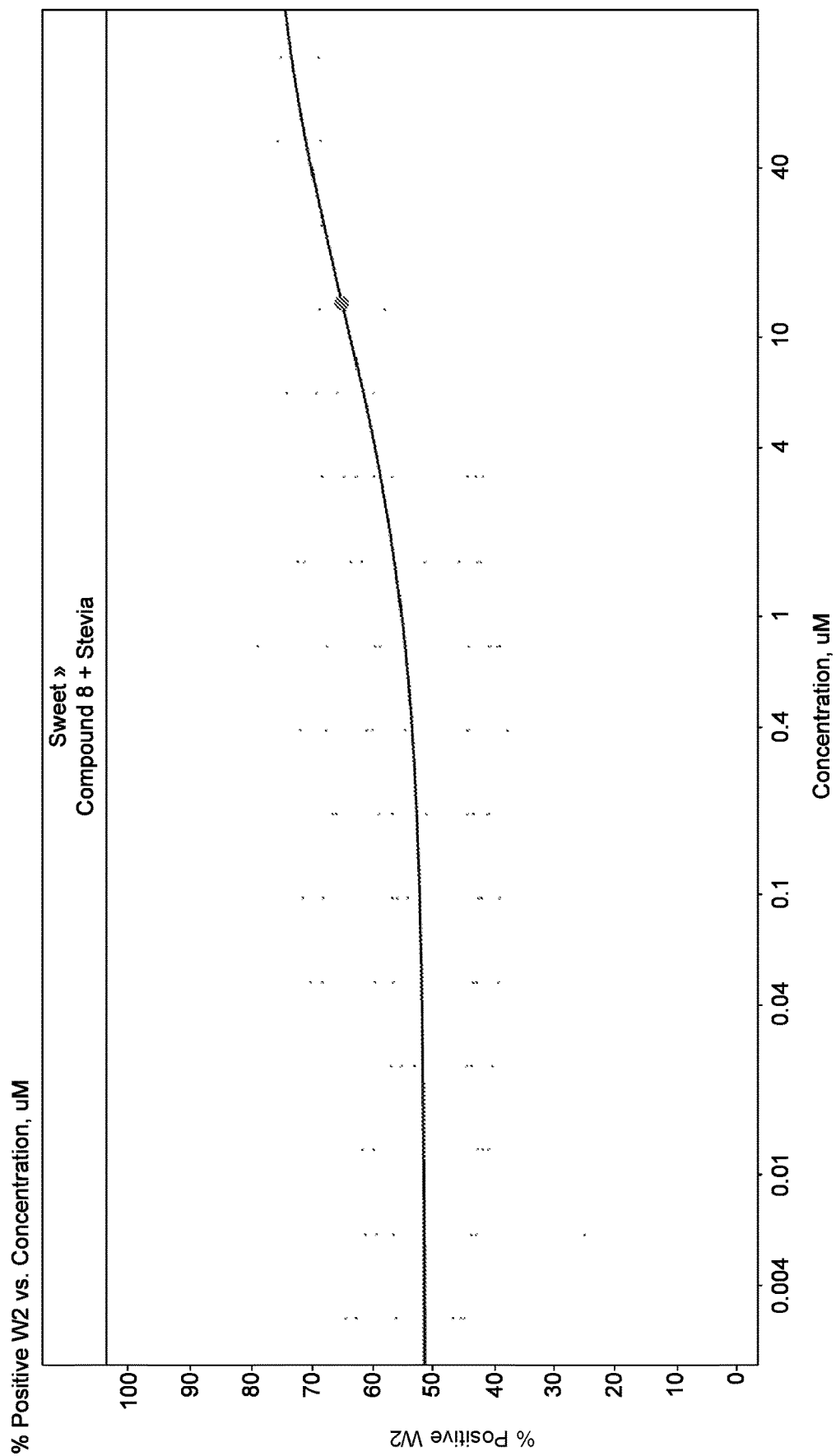

FIG. 64 is a dose response curve depicting the dose dependent level of activation of the sweet receptors by samples containing a *stevia* blend and one or more of the compounds disclosed herein.

Figure 65:
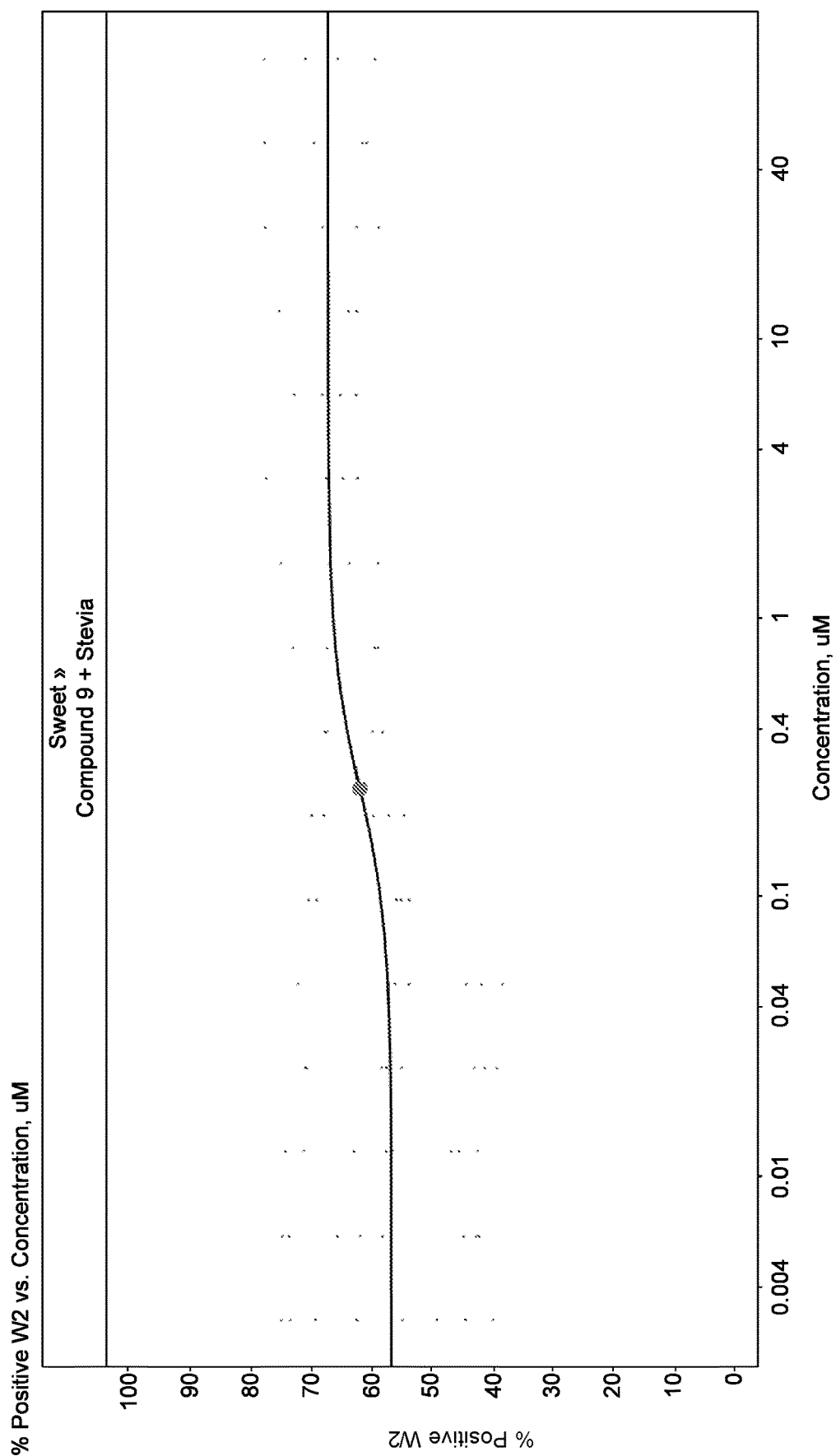

FIG. 65 is a dose response curve depicting the dose dependent level of activation of the sweet receptors by samples containing a *stevia* blend and one or more of the compounds disclosed herein.

Figure 66:
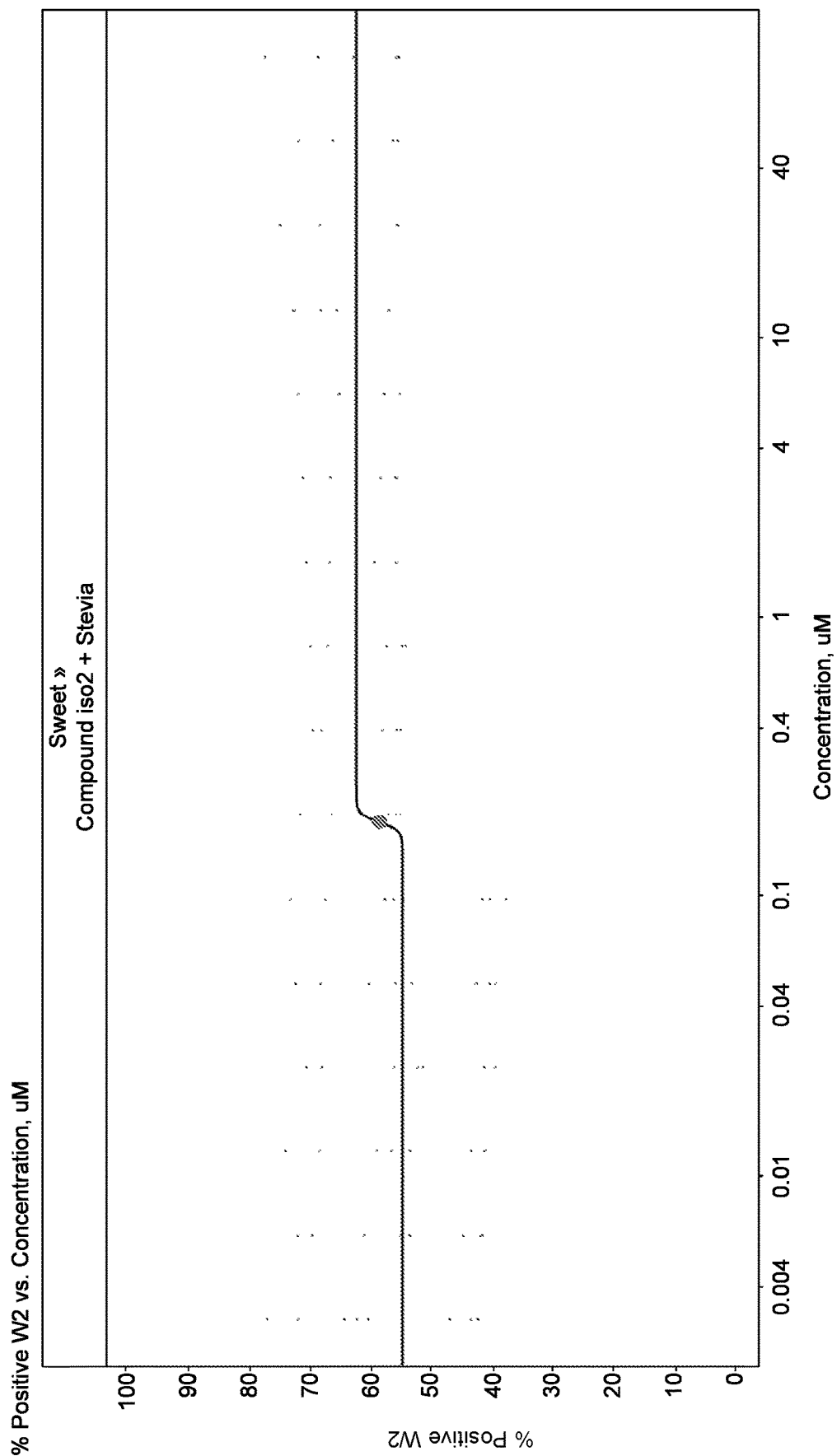

FIG. 66 is a dose response curve depicting the dose dependent level of activation of the sweet receptors by samples containing a *stevia* blend and one or more of the compounds disclosed herein.

Figure 67:
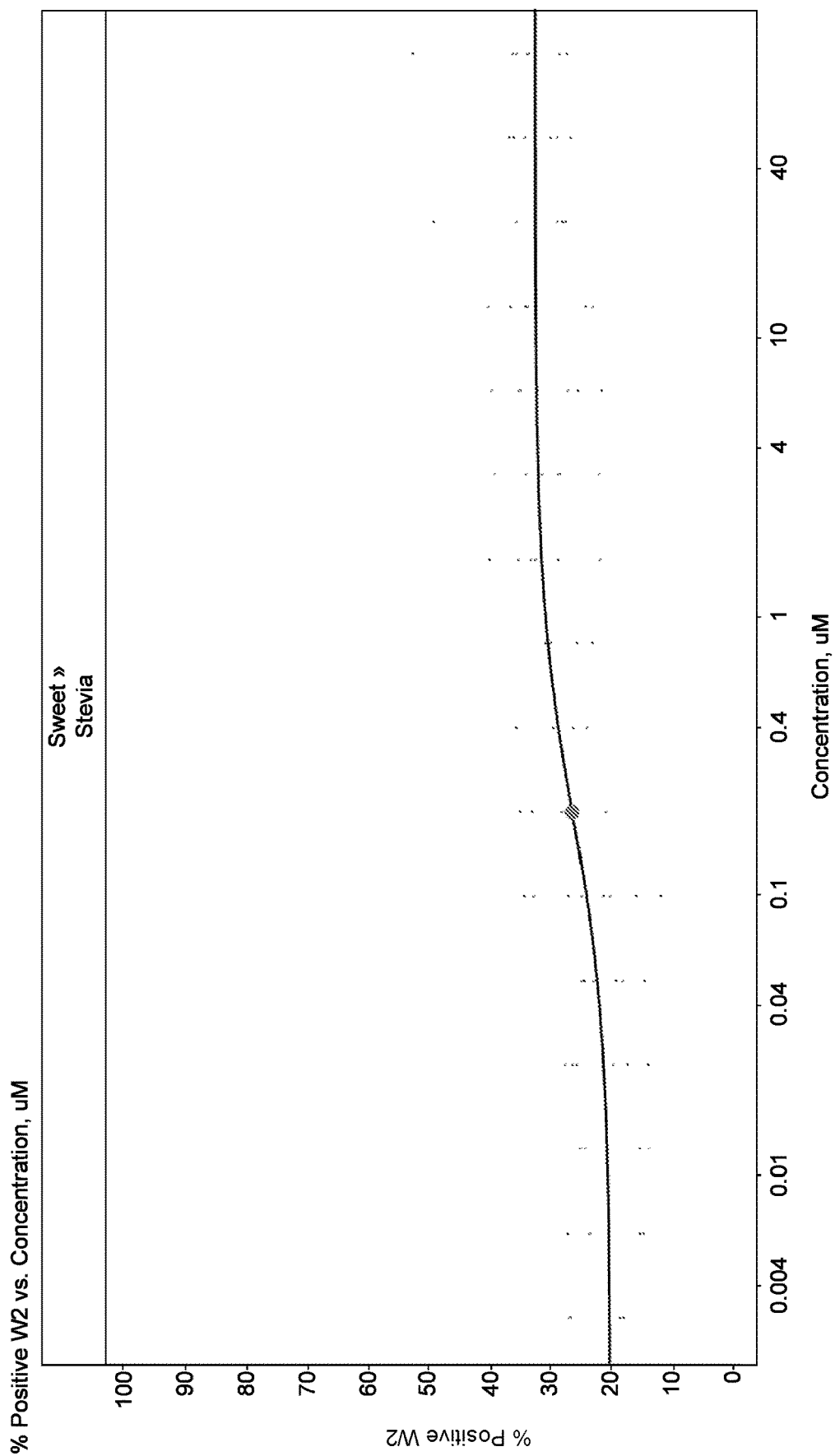

FIG. 67 is a dose response curve depicting the dose dependent level of activation of the sweet receptors by samples containing a *stevia* blend.

Figure 68:
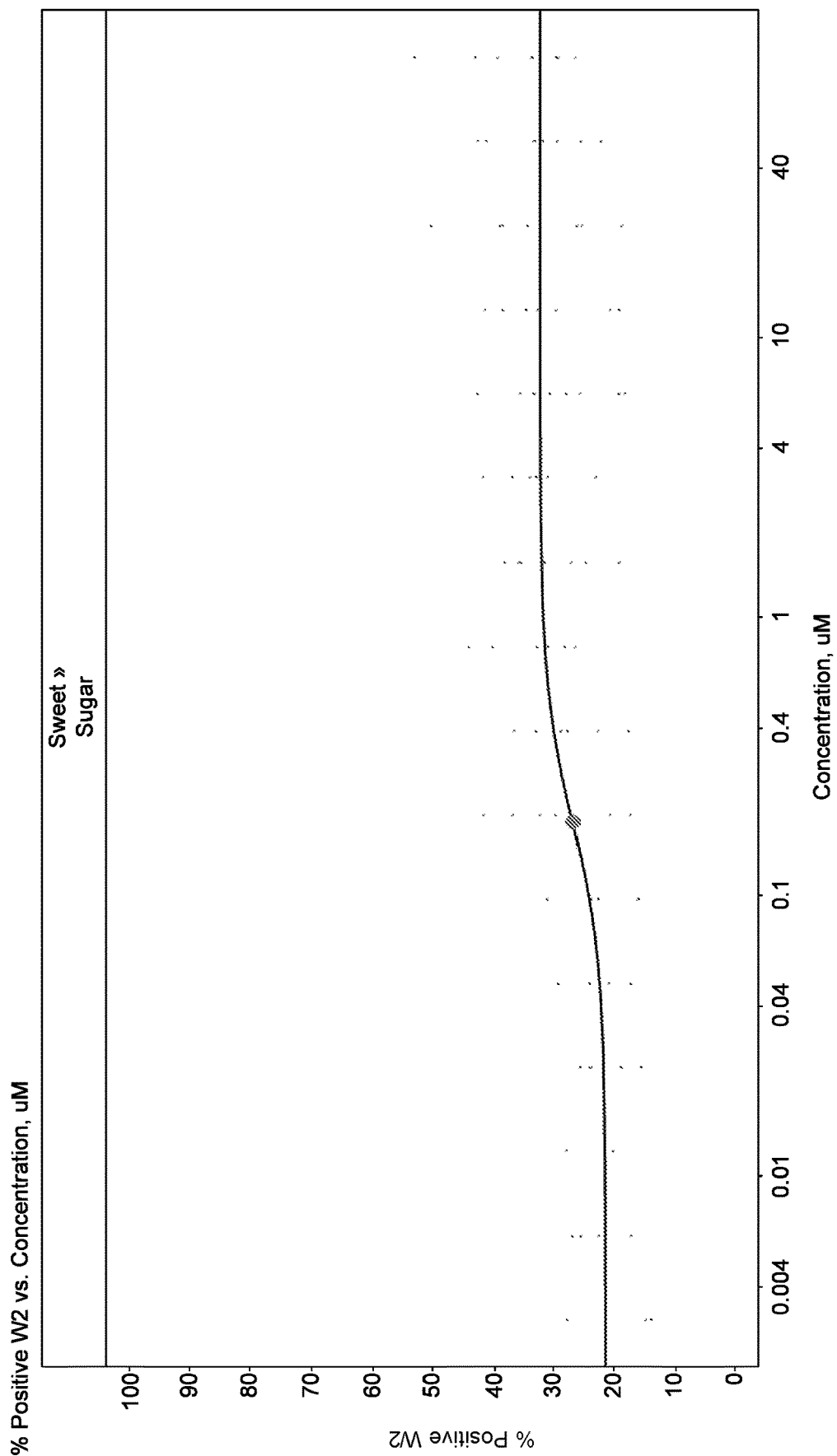

FIG. 68 is a dose response curve depicting the dose dependent level of activation of the sweet receptors by samples containing sugar.

DETAILED DESCRIPTION

Potent non-nutritive sweeteners, including the steviolglycosides, often have off-tastes (e.g., bitterness, astringency, licorice flavor, metallic taste, and/or lingering aftertastes). It has now been unexpectedly discovered that the off-tastes of steviol glycosides and blends thereof, can be improved by a flavor-modifying composition containing one or more, or two or more, or three or more, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

Definitions

Various examples and embodiments of the inventive subject matter disclosed here are possible and will be apparent to the person of ordinary skill in the art, given the benefit of this disclosure. In this disclosure reference to "some embodiments," "certain embodiments," "particular embodiments" and similar phrases each means that those embodiments are non-limiting examples of the inventive subject matter, and there are alternative embodiments which are not excluded.

The articles "a," "an," and "the" are used herein to refer to one or to more than one (i.e., at least one) of the grammatical object of the article. By way of example, "a compound" means one compound or more than one compound.

The words "comprise", "comprising", "contains", "containing", "include" or "including" are open-ended, and should mean that a given composition or process can optionally also have additional components, features or elements beyond those expressly described.

The term "about" is used throughout this disclosure and the appended claims to account for ordinary inaccuracy and variability, such as in measurement, testing and the like, in the composition or method, etc. As used herein, the term "about" can mean ±20% of the noted value. By way of example only, a composition comprising "about 30 ppm" of a compound could include from 24 ppm of the compound up to and including 36 ppm of the compound.

As used herein, "taste" refers to a combination of sweetness perception, temporal effects of sweetness perception, i.e., on-set and duration, off-tastes, e.g., bitterness and metallic taste, residual perception (aftertaste), and tactile perception, e.g., body and thickness.

The term "substantially free of any compounds" having certain molecular weights refers to a sweetener composition or a flavor-modifying composition of the present disclosure that contains little or no detectable amount of such compounds under appropriate HPLC conditions. In certain embodiments, the sweetener composition and/or flavor-modifying composition can be substantially free of phenolic oligomers and/or polymeric polyphenols, such as polyproanthcyanidins, polymers of flavanol glycosides, polymers of hydroxycinnamic acid derivatives (esters, glycosides and amides), and/or polymers of gallic acid derivatives (esters, glycosides and amides), or combinations of any of the foregoing. A sweetener composition of the present disclosure substantially free of such compounds may contain, for example, less than about 5 wt %, less than about 4 wt %, less than about 3 wt %, less than about 2 wt %, less than about 1 wt %, or less than about 0.1 wt %, less than about 0.01 wt %, or less than about 0.001 wt %, less than 0.0001 wt %, or less than 0.00001 wt % of such compounds, based on the total weight of the flavor-modifying compounds.

The term "nutritive sweetener" refers generally to sweeteners which provide significant caloric content in typical usage amounts, e.g., more than about 5 calories per 8 oz. serving of a beverage.

As used herein, the term "non-nutritive sweetener" refers to all sweeteners other than nutritive sweeteners.

As used herein, the terms "a reference composition" and "a reference sweetener" refer to a corresponding and otherwise identical composition except without specified ingredients, or sweetener that has not been subjected to a taste modification method disclosed herein.

As used herein, the term "reduced bitterness and/or astringency" means reduced by at least about 10%, at least about 15%, at least about 20%, at least about 25%, at least about 30%, at least about 40%, at least about 50%, at least about 60%, at least about 75%, or at least about 100% as determined by standard sensory testing methodology.

The terms "syrup" and "concentrate" are used interchangeably throughout the specification and refer to aqueous sweetener compositions suitable for use in beverage or food products.

Sweetener Compositions

In various embodiments, the present disclosure provides a sweetener composition comprising a non-nutritive sweetener and one or more, or two or more compounds, or three or more compounds, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. In certain embodiments, at least one of the compounds is furfural, 4-hexen-1-ol, trans-2,4-hexadienal, 2,4-hexadien-1-ol, 5-methyl-furfural, butyl acetate, 3-methylbutanol, 2-methylbutanol, ethyl octanoate, ethyl decanoate, or ethyl hexadecanoate. These compounds are present in amounts suitable to modify the flavor of the non-nutritive sweetener.

In some embodiments, the compound furfural is present in an amount from about 6 ppb (parts per billion) to about 10 ppm (parts per million), from about 13 ppb to about 5 ppm, or from about 80 ppb to about 5 ppm.

In some embodiments, the compound 4-hexen-1-ol is present in an amount from about 0.6 ppb to about 1 ppm, from about 1.3 ppb to about 0.5 ppm, or from about 8 ppb to about 0.5 ppm.

In some embodiments, the compound trans-2,4-hexadienal is present in an amount from about 2.5 ppb to about 4 ppm, from about 5 ppb to about 2 ppm, or from about 30 ppb to about 2 ppm.

In some embodiments, the compound 2,4-hexadien-1-ol is present in an amount from about 0.4 ppb to about 4 ppm, from about 2 ppb to about 3 ppm, from about 4 ppb to about 1.5 ppm, or from about 24 ppb to about 1.5 ppm.

In some embodiments, the compound 5-methyl-furfural is present in an amount from about 0.3 ppb to about 1 ppm, from about 0.5 ppb to about 0.5 ppm, from about 0.7 ppb to about 0.25 ppm, or from about 4 ppb to about 0.25 ppm.

In some embodiments, the compound delta-tetradecalactone is present in an amount from about 0.1 ppb to about 0.04 ppm, from about 0.1 ppb to about 0.02 ppm, or from about 0.3 ppb to about 0.02 ppm.

In some embodiments, the compound cis-4-methyl-5-butyldihydro-2(3H)-furanone and/or trans-4-methyl-butyldihydro-2(3H)-furanone are present in an amount from about 0.1 ppb to about 0.5 ppm, from about 0.2 ppb to about 0.3 ppm, from about 0.3 ppb to about 0.1 ppm, or from about 1.6 ppb to about 0.1 ppm. The cis and trans isomers of 4-methyl-5-butyldihydro-2(3H)-furanone, and in certain instances, mixtures of these compounds, can be alternatively referred to as (4R,5R)-5-butyl-4-methyldihydrofuran-2 (3H)-one, (4S,5S)-5-butyl-4-methyldihydrofuran-2(3H)-one, cis-3-methyl-4-octanolide, trans-3-methyl-4-octanolide, (3S,4S)-(−)-4-butyl-3-methylbutan-4-olide, (3R,4R)-(−)-4-butyl-3-methylbutan-4-olide, quercus lactone, cis-whiskey lactone, trans-whiskey lactone, cis-3-methyl-γ-octalactone, and trans-β-methyl-γ-octalactone. In certain embodiments, both cis- and trans-4-methyl-5-butyldihydro-2(3H)-furanone can be either the R- or the S-enantiomer or a mixture of enantiomers, including, for example, a racemic mixture. In certain embodiments, the 4-methyl-5-butyldihydro-2(3H)-furanone compounds included in the sweetener composition described herein can have the CAS registry numbers 39212-23-2 or 147254-32-8.

In some embodiments, the compound butyl acetate can be present in the ready-to-drink beverage in a concentration ranging from about 0.1 ppb to about 10 ppb, and in particular embodiments, at about 0.8 ppb. In other embodiments, butyl acetate can be present in an amount ranging from about 1 ppb to about 500 ppb, or from about 200 ppb to about 400 ppb.

In some embodiments, the compound 3-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm.

In some embodiments, the compound ethyl octanoate is present in an amount from about 0.1 ppb to about 0.4 ppm, from about 0.5 ppb to about 0.2 ppm, or from about 3.2 ppb to about 0.2 ppm.

In some embodiments, the compound ethyl decanoate is present in an amount from about 0.1 ppb to about 2.4 ppm, from about 0.3 ppb to about 1.2 ppm, or from about 1.6 ppb to about 1.2 ppm.

In some embodiments, the compound ethyl hexadecanoate is present in an amount from about 0.6 ppb to about 1 ppm, from about 1.3 ppb to about 0.5 ppm, or from about 7.9 ppb to about 0.5 ppm.

In some embodiments, the compound 2-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm.

In some embodiments, the sweetener composition contains furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, and ethyl hexadecanoate. These compounds can be present in any of the ranges discussed above.

In some embodiments, the sweetener composition contains furfural, 4-hexen-1-ol, trans-2,4-hexadienal, 2,4-hexadien-1-ol, 5-methyl-furfural, trans-4-methyl-5-butyldihydro-2(3H)-furanone, butyl acetate, 3-methylbutanol, 2-methylbutanol, ethyl decanoate, and ethyl hexadecanoate. These compounds can be present in any of the ranges discussed above.

In some embodiments, the sweetener composition contains 3-methylbutanol. This compound can be present in any of the ranges discussed above.

In some embodiments, the sweetener composition contains 2-methylbutanol. This compound can be present in any of the ranges discussed above.

In some embodiments, the sweetener composition contains butyl acetate and 3-methylbutanol. These compounds can be present in any of the ranges discussed above.

In some embodiments, the sweetener composition contains 3-methylbutanol and furfural. These compounds can be present in any of the ranges discussed above.

In some embodiments, the sweetener composition contains butyl acetate and furfural. These compounds can be present in any of the ranges discussed above.

In some embodiments, the sweetener composition contains 3-methylbutanol and trans-4-methyl-5-butyldihydro-2 (3H)-furanone. These compounds can be present in any of the ranges discussed above.

In some embodiments, the sweetener composition contains furfural and trans-4-methyl-5-butyldihydro-2(3H)-furanone. These compounds can be present in any of the ranges discussed above.

In some embodiments, the sweetener composition contains butyl acetate and trans-4-methyl-5-butyldihydro-2 (3H)-furanone. These compounds can be present in any of the ranges discussed above.

In some embodiments, the sweetener composition contains butyl acetate, 3-methylbutanol, and furfural. These compounds can be present in any of the ranges discussed above.

In some embodiments, the sweetener composition contains butyl acetate, 3-methylbutanol, and trans-4-methyl-5- butyldihydro-2(3H)-furanone. These compounds can be present in any of the ranges discussed above.

In some embodiments, the sweetener composition contains 3-methylbutanol, furfural, and trans-4-methyl-5-butyldihydro-2(3H)-furanone. These compounds can be present in any of the ranges discussed above.

In some embodiments, the sweetener composition contains butyl acetate, furfural, and trans-4-methyl-5-butyldihydro-2(3H)-furanone. These compounds can be present in any of the ranges discussed above.

In some embodiments, the sweetener composition contains butyl acetate, 3-methylbutanol, furfural, and trans-4-methyl-5-butyldihydro-2(3H)-furanone. These compounds can be present in any of the ranges discussed above.

In some embodiments, the sweetener composition contains furfural, 4-hexen-1-ol, trans-2,4-hexadienal, 2,4-hexadien-1-ol, 5-methyl-furfural, trans-4-methyl-5-butyldihydro-2(3H)-furanone, butyl acetate, 2-methylbutanol, ethyl decanoate, and ethyl hexadecanoate. These compounds can be present in any of the ranges discussed above.

In some embodiments, the sweetener composition contains butyl acetate, 2-methylbutanol, furfural, and trans-4-methyl-5-butyldihydro-2(3H)-furanone. These compounds can be present in any of the ranges discussed above.

In some embodiments, the sweetener composition is substantially free of any high molecular weight compounds, i.e., compounds having a molecular weight of greater than about 500, greater than about 600, greater than about 700, greater than about 800, greater than about 900, greater than about 1000, greater than about 1100, greater than about 1200, greater than greater than about 1300, greater than about 1400, greater than about 1500, greater than about 1600, greater than about 1700, greater than about 1800, greater than about 1900, greater than about 2000, greater than about 2100, greater than about 2200, greater than about 2300, greater than about 2400, greater than about 2500, greater than about 2600, greater than about 2700, greater than about 2800, greater than about 2900, or greater than about 3000 daltons. Exemplary high molecular weight compounds that can be substantially absent from the compositions described herein include phenolic oligomers or polymeric polyphenols, such as polyproanthcyanidins, polymers of flavanol glycosides, polymers of hydroxycinnamic acid derivatives (esters, glycosides and amides), or polymers of gallic acid derivatives (esters, glycosides and amides).

In various embodiments, the present disclosure provides a method of making a sweetener composition comprising adding to a non-nutritive sweetener one or more, or two or more, or three or more, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

The adding can be effected by incorporating these compounds into a non-nutritive sweetener by any appropriate means that are known in the art. For example, a pre-mix of two or more of these compounds can be prepared by dissolving them in an appropriate medium (e.g., water or water/co-solvent), and adding the pre-mix to a non-nutritive sweetener.

Alternatively, an aqueous solution of a non-nutritive sweetener can be prepared and two of more of these compounds can be added to the solution by any appropriate techniques.

In various embodiments, the present disclosure also provides a sweetener composition comprising a non-nutritive sweetener, and a flavor-modifying composition comprising one or more, or two or more compounds, or three or more compounds, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. These compounds are present in an amount sufficient to modify the flavor of the non-nutritive sweetener.

In some embodiments, the compound furfural is present in an amount from about 6 ppb to about 10 ppm, from about 13 ppb to about 5 ppm, or from about 80 ppb to about 5 ppm.

In some embodiments, the compound 4-hexen-1-ol is present in an amount from about 0.6 ppb to about 1 ppm, from about 1.3 ppb to about 0.5 ppm, or from about 8 ppb to about 0.5 ppm.

In some embodiments, the compound trans-2,4-hexadienal is present in an amount from about 2.5 ppb to about 4 ppm, from about 5 ppb to about 2 ppm, or from about 30 ppb to about 2 ppm.

In some embodiments, the compound 2,4-hexadien-1-ol is present in an amount from about 0.4 ppb to about 4 ppm, from about 2 ppb to about 3 ppm, from about 4 ppb to about 1.5 ppm, or from about 24 ppb to about 1.5 ppm.

In some embodiments, the compound 5-methyl-furfural is present in an amount from about 0.3 ppb to about 1 ppm, from about 0.5 ppb to about 0.5 ppm, from about 0.7 ppb to about 0.25 ppm, or from about 4 ppb to about 0.25 ppm.

In some embodiments, the compound delta-tetradecalactone is present in an amount from about 0.1 ppb to about 0.04 ppm, from about 0.1 ppb to about 0.02 ppm, or from about 0.3 ppb to about 0.02 ppm.

In some embodiments, the compound 4-methyl-5-butyldihydro-2(3H)-furanone (as cis-4-methyl-5-butyldihydro-2(3H)-furanone, trans-4-methyl-5-butyldihydro-2(3H)-furanone, or a mixture of cis- and trans-4-methyl-5-butyldihydro-2(3H)-furanone, all as discussed previously) is present in an amount from about 0.1 ppb to about 0.5 ppm, from about 0.2 ppb to about 0.3 ppm, from about 0.3 ppb to about 0.1 ppm, or from about 1.6 ppb to about 0.1 ppm.

In some embodiments, the compound butyl acetate can be present in the ready-to-drink beverage in a concentration ranging from about 0.1 ppb to about 10 ppb, and in particular embodiments, at about 0.8 ppb. In other embodiments, butyl acetate can be present in an amount ranging from about 1 ppb to about 500 ppb, or from about 200 ppb to about 400 ppb.

In some embodiments, the compound 3-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm.

In some embodiments, the compound ethyl octanoate is present in an amount from about 0.1 ppb to about 0.4 ppm, from about 0.5 ppb to about 0.2 ppm, or from about 3.2 ppb to about 0.2 ppm.

In some embodiments, the compound ethyl decanoate is present in an amount from about 0.1 ppb to about 2.4 ppm, from about 0.3 ppb to about 1.2 ppm, or from about 1.6 ppb to about 1.2 ppm.

In some embodiments, the compound ethyl hexadecanoate is present in an amount from about 0.6 ppb to about 1 ppm, from about 1.3 ppb to about 0.5 ppm, or from about 7.9 ppb to about 0.5 ppm.

In some embodiments, the compound 2-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm.

In some embodiments, the flavor-modifying composition contains furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, and ethyl hexadecanoate. These compounds can be present in any of the ranges discussed above.

In some embodiments, the flavor-modifying composition contains furfural, 4-hexen-1-ol, trans-2,4-hexadienal, 2,4-hexadien-1-ol, 5-methyl-furfural, trans-4-methyl-5-butyldihydro-2(3H)-furanone, butyl acetate, 3-methylbutanol, ethyl decanoate, and ethyl hexadecanoate. These compounds can be present in any of the ranges discussed above.

In some embodiments, the flavor-modifying composition contains 3-methylbutanol. This compound can be present in any of the ranges discussed above.

In some embodiments, the flavor-modifying composition contains 2-methylbutanol. This compound can be present in any of the ranges discussed above.

In some embodiments, the flavor-modifying composition contains butyl acetate and 3-methylbutanol. These compounds can be present in any of the ranges discussed above.

In some embodiments, the flavor-modifying composition contains 3-methylbutanol and furfural. These compounds can be present in any of the ranges discussed above.

In some embodiments, the flavor-modifying composition contains butyl acetate and furfural. These compounds can be present in any of the ranges discussed above.

In some embodiments, the flavor-modifying composition contains 3-methylbutanol and trans-4-methyl-5-butyldihydro-2(3H)-furanone. These compounds can be present in any of the ranges discussed above.

In some embodiments, the flavor-modifying composition contains furfural and trans-4-methyl-5-butyldihydro-2(3H)-furanone. These compounds can be present in any of the ranges discussed above.

In some embodiments, the flavor-modifying composition contains butyl acetate and trans-4-methyl-5-butyldihydro-2(3H)-furanone. These compounds can be present in any of the ranges discussed above.

In some embodiments, the flavor-modifying composition contains butyl acetate, 3-methylbutanol, and furfural. These compounds can be present in any of the ranges discussed above.

In some embodiments, the flavor-modifying composition contains butyl acetate, 3-methylbutanol, and trans-4-methyl-5-butyldihydro-2(3H)-furanone. These compounds can be present in any of the ranges discussed above.

In some embodiments, the flavor-modifying composition contains 3-methylbutanol, furfural, and trans-4-methyl-5-butyldihydro-2(3H)-furanone. These compounds can be present in any of the ranges discussed above.

In some embodiments, the flavor-modifying composition contains butyl acetate, furfural, and trans-4-methyl-5-butyldihydro-2(3H)-furanone. These compounds can be present in any of the ranges discussed above.

In some embodiments, the flavor-modifying composition contains butyl acetate, 3-methylbutanol, furfural, and trans-4-methyl-5-butyldihydro-2(3H)-furanone. These compounds can be present in any of the ranges discussed above.

In some embodiments, the flavor-modifying composition contains furfural, 4-hexen-1-ol, trans-2,4-hexadienal, 2,4-hexadien-1-ol, 5-methyl-furfural, trans-4-methyl-5-butyldihydro-2(3H)-furanone, butyl acetate, 2-methylbutanol, ethyl decanoate, and ethyl hexadecanoate. These compounds can be present in any of the ranges discussed above.

In some embodiments, the flavor-modifying composition contains butyl acetate, 2-methylbutanol, furfural, and trans-4-methyl-5-butyldihydro-2(3H)-furanone. These compounds can be present in any of the ranges discussed above.

In some embodiments, the flavor-modifying composition is substantially free of any high molecular weight compounds, i.e., compounds having a molecular weight of greater than about 500, greater than about 600, greater than about 700, greater than about 800, greater than about 900, greater than about 1000, greater than about 1100, greater than about 1200, greater than greater than about 1300, greater than about 1400, greater than about 1500, greater than about 1600, greater than about 1700, greater than about 1800, greater than about 1900, greater than about 2000, greater than about 2100, greater than about 2200, greater than about 2300, greater than about 2400, greater than about 2500, greater than about 2600, greater than about 2700, greater than about 2800, greater than about 2900, or greater than about 3000 daltons. Exemplary high molecular weight compounds that can be substantially absent from the compositions described herein include phenolic oligomers or polymeric polyphenols, such as polyproanthcyanidins, polymers of flavanol glycosides, polymers of hydroxycinnamic acid derivatives (esters, glycosides and amides), or polymers of gallic acid derivatives (esters, glycosides and amides).

In some embodiments, the flavor-modifying composition is an aqueous composition that is free of any organic co-solvents, including, for example, alcohols (e.g., methanol or ethanol), glycols (e.g., propylene glycol), ketones (e.g., acetone), or mixtures thereof. In some embodiments, the aqueous flavor-modifying composition may contain a minor amount of ethanol, propylene glycol or mixtures thereof. For example, the aqueous flavor-modifying composition can contain up to about 10 wt %, up to about 5 wt %, up to about 1 wt %, up to about 0.1 wt %, or up to about 0.01 wt % of ethanol, based on the total weight the water and ethanol. Also, for example, the aqueous flavor-modifying composition can contain up to about 10 wt %, up to about 5 wt %, up to about 1 wt %, up to about 0.1 wt %, or up to about 0.01 wt % of propylene glycol, based on the total weight the water and glycol.

It has been discovered that by contacting a steviol glycoside aqueous solution with a wood, such as oak, e.g., in an oak barrel, or in a glass container that contains oak chips, over a period of hours (e.g., at least about 8 hours), or days (e.g., at least 3 days), or weeks (e.g., at least 2 weeks) at an appropriate temperature (i.e., above the freezing point of the solution and below the boiling point of the solution), the flavor of steviol glycosides can be modified (e.g., reduced bitterness and/or astringency, and/or improved overall sweet quality (e.g., sugar like taste and roundness)).

For example, the contacting temperature can range from about 10° C. to about 65° C., from about 10° C. to about 50° C., from about 15° C. to about 45° C., or from about 20° C. to about 50° C., or from about 20° C. to about 40° C. In particular, the contacting temperature is room temperature (about 21° C. to about 23° C.). For example, the contacting time can be at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, or at least about 6 weeks.

It has also been discovered that during the oak extraction in an aqueous medium, a mixture of volatile low molecular weight compounds are extracted from oak wood. The typical components of the mixture extracted from oak wood are shown in Table 1.

TABLE 1

Structure and molecular weight of compounds found in aqueous oak extraction

| Name | Structure | Molecular weight |
|---|---|---|
| Furfural | 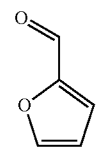 | 96 |
| 4-hexen-1-ol | 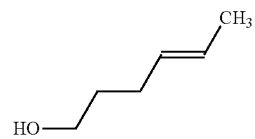 | 100 |
| trans-2,4-hexadienal | 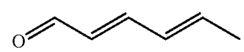 | 96 |
| 2,4-hexadien-1-ol | 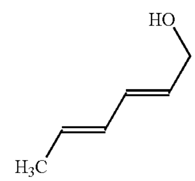 | 98 |
| 5-methyl-furfural | 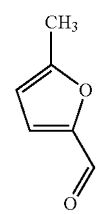 | 110.1 |
| delta-tetradecalactone | 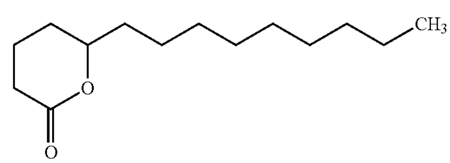 [SMILES: CCCCCCCCCC1CCCC(=O)O1] | 226 |
| 4-methyl-5-butyldihydro-2(3H)-furanone | 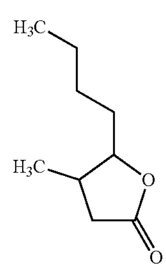 | 156 |
| butyl acetate | 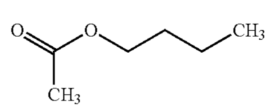 | 116 |

TABLE 1-continued

Structure and molecular weight of compounds found in aqueous oak extraction

| Name | Structure | Molecular weight |
| --- | --- | --- |
| 3-methylbutanol | (structure) | 88 |
| ethyl octanoate | (structure) | 172 |
| ethyl decanoate | (structure) | 200 |
| ethyl hexadecanoate | (structure) | 284 |

It has further been discovered that during the oak extraction in an aqueous medium, no detectable amount of hydrophobic high molecular weight compounds (e.g., greater than 500 daltons) phenolic oligomers or polymeric polyphenols, such as polyproanthcyanidins, polymers of flavanol glycosides, polymers of hydroxycinnamic acid derivatives (esters, glycosides and amides), and/or polymers of gallic acid derivatives (esters, glycosides and amides) are extracted from oak. Surprisingly, it has been discovered that at least two, and in some embodiments, at least three, at least four, or all of the compounds identified in Table 1, can improve and modify the taste profile of non-nutritive sweeteners, such as one or more steviol glycosides.

It has also been discovered that the compounds described in Table 1 can be added directly into a non-nutritive sweetener solution, such as an aqueous steviol glycoside solution, within the concentrations specified herein, to reduce bitterness and/or astringency, and/or to improve overall sweet quality (e.g., sugar like taste and roundness) of the steviol glycoside aqueous solution.

In embodiments prepared via oak aging, the relative quantities of the various components that can be extracted from oak wood will vary with the species of oak, the site on which the trees of a particular species were grown and differences within the tree itself. The species effect is under genetic control and is responsible for the largest differences between the volatiles content found in various oak species such as European white oak (*Q. robur* and *Q. Sessilis*) and American white oak (*Q. alba*). However, the site at which a tree is grown can exert subtle influences on the flavor makeup of the wood since it is the microclimate of the site that determines the relative amounts of spring and summer wood. Since spring wood is more porous than summer wood, trees growing on cooler sites have less dense wood. Conversely, trees grown in warmer regions have wood of higher density. Other factors such as rainfall and soil also play a role. Oak barrels or oak chips made of less dense wood would allow a composition to penetrate the staves and extract the flavor-modifying components more readily.

In some embodiments, oak barrels or oak chips can be charred (toasted). The level of toast can vary from a light toast to a medium toast, or to heavy toast. In general, it is believed that lignin will degrade to aromatics by toasting, which provides more volatile compounds available for extraction.

In some embodiments, the flavor-modifying composition of the present disclosure can modify the taste profile of a non-nutritive sweetener to reduce bitterness and/or astringency of the non-nutritive sweetener, and/or to improve overall sweet quality (e.g., sugar like taste and roundness) of the sweetener, without imparting oak notes.

In other embodiments, the flavor-modifying composition of the present disclosure can modify the taste profile of a non-nutritive sweetener to reduce bitterness and/or astringency of the non-nutritive sweetener, and/or to improve overall sweet quality (e.g., sugar like taste and roundness) of the sweetener, and also imparts oak notes.

Thus, the taste profile of the sweetener composition of present disclosure can be modified, and/or altered by the flavor-modifying composition in a controllable manner. More specifically, the flavor-modifying effect of a flavor-modifying composition of the present disclosure can be controlled by selecting different types of oak (e.g., charred or un-charred, medium charred or heavily charred, the European or American white oak), by adjusting the amount of oak used, by changing the contacting method (e.g., oak barrel or oak chips), by varying the contacting temperature (e.g., room temperature or elevated temperature), or by regulating the contacting time (e.g., days or weeks).

An exemplary oak barrel is shown in FIG. 1. Oak barrels can be made of the European white oak, or the American white oak. Oak barrels can be un-charred, lightly charred, medium charred or heavily charred. Suitable oak barrels include those used in wine making industry, and can be purchased from online (www.buyoakbarrels.com).

Figure 2:
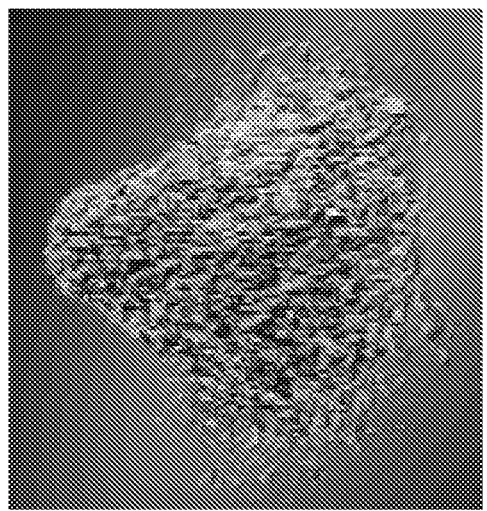
FIG. 2 depicts exemplary oak chips.

An exemplary oak chip is shown in FIG. 2. Oak chips can be made of the European white oak, or the American white oak. Oak chips can be un-charred, lightly charred, medium charred or heavily charred. Oak chips can be in any suitable sizes and shapes, e.g., flakes or spirals. Suitable oak chips can be purchased from various retail and wholesale distributors, including The Barrel Mill, Avon, Minn. 56310.

In various embodiments, the present disclosure provides a method of making a sweetener composition comprising adding to a non-nutritive sweetener one or more, or two or more, or three or more, or four or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

The adding can be effected by incorporating these compounds into a non-nutritive sweetener by any appropriate means that are known in the art. For example, a pre-mix of one or more of these compounds can be prepared by dissolving them in an appropriate medium (e.g., water or water/co-solvent), and adding the pre-mix to a non-nutritive sweetener.

Alternatively, an aqueous solution of a non-nutritive sweetener can be prepared and one of more of these compounds can be added to the solution by any appropriate techniques.

In various embodiments, the present disclosure also provides a method of making a sweetener composition, comprising adding to an aqueous solution of the non-nutritive sweetener a flavor-modifying composition comprising one or more, or two or more, or three or more, or four more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. In certain embodiments, at least one of the compounds is furfural, 4-hexen-1-ol, trans-2,4-hexadienal, 2,4-hexadien-1-ol, 5-methyl-furfural, butyl acetate, 3-methylbutanol, 2-methylbutanol, ethyl octanoate, ethyl decanoate, or ethyl hexadecanoate In some embodiments, the adding can be effected by contacting the aqueous solution of a non-nutritive sweetener with oak wood, such as an oak barrel or oak chips. Oak barrels or chips can be made of the European white oak, or the American white oak. Oak barrels or chips can be un-charred, lightly charred, medium charred or heavily charred, as described above.

In some embodiments, the aqueous solution of a non-nutritive sweetener may contain from about 1 wt % to about 60 wt %, from about 1 wt % to about 50 wt %, from about 1 wt % to about 40 wt %, from about 1 wt % to about 30 wt %, from about 1 wt % to about 25 wt %, from about 5 wt % to about 50 wt %, from about 5 wt % to about 40 wt %, from about 5 wt % to about 20 wt %, from about 5 wt % to about 15 wt %, from about 5 wt % to about 10 wt %, from about 6 wt % to about 13 wt %, or about 4 wt %, about 5 wt %, about 6 wt %, about 7 wt %, about 8 wt %, about 9 wt %, about 10 wt %, about 11 wt %, or about 12 wt %, or about 15 wt %, about 20 wt %, about 25 wt %, or about 30 wt %, about 35 wt %, about 40 wt %, about 45 wt %, about 50 wt %, about 55 wt %, or about 60 wt % of the non-nutritive sweetener.

In some embodiments, the contacting occurs by storing the aqueous solution of the non-nutritive sweetener in an oak barrel, or in an appropriate vessel containing oak chips, for a sufficient of amount of time under an appropriate temperature. For example, the contacting temperature can range from about 10° C. to about 65° C., from about 10° C. to about 50° C., from about 15° C. to about 45° C., or from about to about 40° C. In particular embodiments, the contacting temperature is room temperature (about 21° C. to about 23° C.).

The contacting time can range from a few hours to a few days, to a few months. In particular embodiments, the contacting time is at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, or at least about 6 weeks.

When the aqueous solution of the non-nutritive sweetener is contacted with oak chips, a filtration step may be employed to remove any fine oak particles, and/or certain colors or odors extracted from the oak chips. The filtration may be carried out by any suitable methods known in the art, e.g., carbon filtration or membrane filtration. An exemplary carbon filter is depicted in FIG. 8.

Non-Nutritive Sweeteners

In addition to the flavor-modifying composition, the sweetener composition of the present disclosure contains a non-nutritive sweetener, which can be a natural or artificial non-nutritive sweetener. Non-nutritive sweeteners include, but are not limited to, a steviol glycoside, Lo Han Guo sweetener, rubusoside, siamenoside, monatin, curculin, glycyrrhizic acid, neohesperidin, dihydrochalcone, glycyrrhizin, glycyphyllin, phloridzin, trilobatin, phyllodulcin, brazzein, hernandulcin, osladin, polypodoside A, baiyunoside, pterocaryoside A and B, mukurozioside, thaumatin, monellin, mabinlins I and II, phlomisoside I, periandrin I, abrusoside A, and cyclocarioside I, mogroside IV, mogroside V, or derivatives or salts thereof, or combinations thereof.

In some embodiments, the non-nutritive sweetener of the present disclosure comprises a steviol glycoside. In some embodiments, the non-nutritive sweetener comprises stevioside, rebaudioside A, rebaudioside B, rebaudioside C, rebaudioside D, rebaudioside E, rebaudioside F, rebaudioside G rebaudioside H rebaudioside I, rebaudioside J, rebaudioside K, rebaudioside L, rebaudioside M, rebaudioside N, rebaudioside O, rebaudioside P, rebaudioside Q, steviolbioside, dulcoside A, or derivatives, or combinations thereof. In some embodiments, the non-nutritive sweetener comprises rebaudioside A, rebaudioside D, stevioside, rebaudioside M, or combinations thereof.

*Stevia* plant produces a number of diterpene glycosides, commonly known as steviol glycosides. The leaves of *Stevia* are able to accumulate up to 10-20% (on dry weight basis) steviol glycosides. The major glycosides found in *Stevia* leaves are Rebaudioside A (2-10%), stevioside (2-10%), and Rebaudioside C (1-2%). Other glycosides such as Rebaudioside B, D, E, and F, steviolbioside and rubusoside are found at much lower levels (about 0-0.2%).

Steviol glycosides differ from each other by molecular structure, physical properties (e.g., water solubility) and by taste properties. In general, stevioside is found to be 110-270 times sweeter than sucrose, Rebaudioside A is between 150 and 320 times, and Rebaudioside C is between 40-60 times sweeter than sucrose. Dulcoside A is 30 times sweeter than sucrose. Rebaudioside D is one of the sweet glycosides found in *Stevia rebaudiana* plant, and possesses a very desirable taste profile, almost lacking the bitterness and lingering licorice aftertaste that are typically present in other steviol glycosides. Thus, Rebaudioside D has a better sugar character and taste profile than Rebaudioside A, but is less water soluble than Rebaudioside A.

Methods for the extraction and purification of steviol glycosides from the *Stevia rebaudiana* plant are known in the art and are described in, for example, U.S. Pat. Nos. 4,361,697; 4,082,858; 4,892,938; 5,972,120; 5,962,678; 7,838,044 and 7,862,845.

In some embodiments, the non-nutritive sweetener of the present disclosure is an aqueous steviol glycoside composition comprising rebaudioside D and a stevioside composition. The stevioside composition and rebaudioside D can be present at a ratio of from about 1:1 to about 50:1 by weight; about 1:1 to about 40:1 by weight; about 1:1 to about 30:1 by weight; about 1:1 to about 20:1 by weight, or about 1:1 to about 10:1 by weight. In particular embodiments, the weight to weight ratio of the stevioside composition to rebaudioside D can be about 1:1, about 2:1, about 3:1, about 4:1, about 5:1, about 6:1, or about 7:1.

In some embodiments, the rebaudioside D is present from about 0.5 wt % (wt % means weight percent) to about 1.5 wt %, from about 1 wt % to about 1.5 wt %, from about 1.3 wt % to about 1.4 wt %, or is present at about 1.3 wt %, about 1.4 wt % or about 1.5 wt % of the aqueous steviol glycoside composition.

The stevioside composition can be a mixture of stevioside and a second steviol glycoside selected from the group consisting of rebaudioside A, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside O, steviolbioside, rubusoside, and dulcoside A. In particular embodiments, the second steviol glycoside can be rebaudioside A or rebaudioside M.

In some embodiments, the stevioside and the second steviol glycoside can be present in the stevioside composition in a weight ratio, on a dry basis, of stevioside to second steviol glycoside from less than 95:5 to 1:99. In some embodiments, the weight ratio of stevioside to the second steviol glycoside, on a dry basis, ranges from about 1:1 to about 2:98.

In some embodiments, the second steviol glycoside can comprise from about 50 wt % to about 98 wt % of the stevioside composition, or about 55 wt %, about 60 wt %, about 65 wt %, about 70 wt %, about 75 wt %, about 80 wt %, about 85 wt %, about 90 wt %, about 95 wt %, about 96 wt %, or about 97 wt % of the stevioside composition.

In specific embodiments, the second steviol glycoside is rebaudioside A. In certain embodiments, the stevioside and rebaudioside A can be present in the stevioside composition in a weight ratio of stevioside to rebaudioside A of from less than 95:5 to 1:99. In particular embodiments, the weight ratio of stevioside to rebaudioside A ranges from about 1:1 to about 2:98. The rebaudioside A can comprise from about 50 wt % to about 98 wt % of the stevioside composition, or about 55 wt %, about 60 wt %, about 65 wt %, about 70 wt %, about 7 wt %5, about 80 wt %, about 85 wt %, about 90 wt %, about 95 wt %, about 96 wt %, or about 97 wt % of the stevioside composition.

In some embodiments, the aqueous steviol glycoside composition can also contain minor amounts of a mixture of other steviol glycosides such as rebaudioside B, rebaudioside C, rebaudioside E, rebaudioside F, rebaudioside G, rebaudioside H, rebaudioside I, rebaudioside J, rebaudioside K, rebaudioside L, rebaudioside M, rebaudioside O, steviolbioside, rubusoside, and dulcoside A.

The aqueous steviol glycoside composition of present disclosure can be prepared by dissolving the sweeteners in an appropriate amount of water, either at room temperature (e.g., about 21° C. to about 23° C.), or at an elevated temperature (e.g., about 30° C. to about 65° C.). Alternatively, the aqueous steviol glycoside composition can be prepared by suspending a known quantity of rebaudioside D in water either at room temperature, or at an elevated temperature, and subsequently adding a known quantity of the stevioside composition to the suspension. In a further alternative, the stevioside composition can be dissolved in an appropriate volume of water either at room temperature or at an elevated temperature, and subsequently be combined with an appropriate amount of rebaudioside D.

During preparation, the aqueous steviol glycoside composition can be mixed at high or low shear and at any of the identified temperatures, as necessary, to induce or aid dissolution. It is within the skill of the ordinary skill artisan to identify the appropriate shear level and/or temperature for a given mixture to obtain the results described herein.

In some embodiments, the non-nutritive sweetener of the present disclosure is an aqueous steviol glycoside composition comprising about 16 wt % rebaudioside D, about 42 wt % rebaudioside A, about 25 wt % stevioside, about 12 wt % rebaudioside C, and about 15% trace level steviol glycosides.

In other embodiments, the non-nutritive sweetener of the present disclosure is an aqueous steviol glycoside composition comprising RA50, where RA50 comprises about 50 wt % rebaudioside A, about 30 wt % stevioside, about 10 wt % rebaudioside C, and about 10 wt % trace level steviol glycosides.

In some embodiments, the non-nutritive sweetener of the present disclosure is an aqueous steviol glycoside composition comprising about 17 wt % rebaudioside D and about 83 wt % RA50, where RA50 comprises about 50 wt % rebaudioside A, about 30 wt % stevioside, about 10 wt % rebaudioside C, and about 10 wt % trace level steviol glycosides.

In other embodiments, the non-nutritive sweetener of the present disclosure is an aqueous steviol glycoside composition comprising about 1.3 wt % rebaudioside D and about 6.7 wt % SG95, where SG95 comprises about 50 wt % to about 65 wt % rebaudioside A, about 15 wt % to about 30 wt % stevioside, and about 5 wt % to about 35 wt % trace level steviol glycosides.

In certain embodiments, the water is "treated water." The terms "treated water," "purified water," "demineralized water," "distilled water," and "r-o water" are understood to be generally synonymous, which refer to water from which substantially all mineral content has been removed, typically containing no more than about 500 ppm total dissolved solids, e.g., 250 ppm total dissolved solids. Methods of producing treated water are known to those of ordinary skill in the art and include deionization, distillation, filtration and reverse osmosis ("r-o"), among others, for example, as disclosed in U.S. Pat. No. 7,052,725.

Three exemplary steviol glycoside compositions are shown in Table 2 below.

TABLE 2

Aqueous steviol glycoside compositions

|   | Rebaudioside A (wt %) | Stevioside (wt %) | Rebaudioside D (wt %) |
|---|---|---|---|
| Composition 1 | 52.6 | 24 | 15.5 |
| Composition 2 | 67.4 | 11.4 | 15.5 |
| Composition 3 | 84 | 0.9 | 14 |

Other Ingredients of Sweetener Compositions

In addition to the non-nutritive sweeteners discussed above, the sweetener composition can further comprise a nutritive sweetener. Exemplary natural nutritive sweeteners that can be combined with the non-nutritive sweeteners include any of those known in the art, for example, crystalline or liquid sucrose, fructose, glucose, dextrose, maltose, trehalose, fructo-oligosaccharides, glucose-fructose syrup from natural sources such as apple, chicory, and honey; high fructose corn syrup, invert sugar, maple syrup, maple sugar, honey, brown sugar molasses, cane molasses, such as first molasses, second molasses, blackstrap molasses, and sugar beet molasses; sorghum syrup, and mixtures thereof.

Other nutritive sweeteners suitable for use in the sweetener composition herein include, but are not limited to, sugar alcohols such as erythritol, sorbitol, mannitol, xylitol, lactitol, isomalt, malitol, tagatose, trehalose, galactose, rhamnose, cyclodextrin, ribulose, threose, arabinose, xylose, lyxose, allose, altrose, mannose, idose, lactose, maltose, isotrehalose, neotrehalose, palatinose or isomaltulose, erythrose, deoxyribose, gulose, talose, erythrulose, xylulose, psicose, turanose, cellobiose, glucosamine, mannosamine, fucose, fuculose, glucuronic acid, gluconic acid, gluconolactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, and mixtures thereof.

In particular embodiments, the sweetener composition can comprise a non-nutritive sweetener, such as a steviol glycoside selected from the group consisting of stevioside, rebaudioside A, rebaudioside B, rebaudioside C, rebaudioside D, rebaudioside E, rebaudioside F, rebaudioside G rebaudioside H rebaudioside I, rebaudioside J, rebaudioside K, rebaudioside L, rebaudioside M, rebaudioside N, rebaudioside O, rebaudioside P, rebaudioside Q, steviolbioside, dulcoside A, and combinations thereof, in combination with a nutritive sweetener. In some embodiments, the nutritive sweetener can be sucrose, high-fructose corn syrup, or a combination thereof.

In still further embodiments, the sweetener composition can comprise a non-nutritive sweetener selected from the group consisting of rebaudioside A, rebaudioside D, stevioside, rebaudioside M, and combinations thereof, in combination with a nutritive sweetener. In certain embodiments, the nutritive sweetener can be sucrose, high-fructose corn syrup, or a combination thereof.

In some embodiments, the ratio (wt/wt) of the non-nutritive sweetener (or combination of non-nutritive sweeteners) to nutritive sweetener (or combination of nutritive sweeteners) can range from about 99:1 to about 1:99. In still further embodiments, the weight ratio can range from about 90:10 to about 10:90, from about 80:20 to about 20:80, from about 70:30 to about 30:70, from about 60:40 to about 40:60; or about 1:1.

In embodiments of the sweetener composition comprising a nutritive sweetener, the nutritive sweetener can be added at any stage of preparation. That is, if the sweetener composition is prepared by aging in a wood barrel, the nutritive sweetener can be added either before, during, or after the ageing process as may be desired.

Alternatively, if the sweetener composition is prepared by adding furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof, to a non-nutritive sweetener (or vice-versa), then the nutritive sweetener can be added at any time before, during, or after the addition of these compounds.

The sweetener composition of the present disclosure can also include one or more rare sugars, such as D-allose, D-psicose (also known as D-allulose), L-ribose, D-tagatose, L-glucose, L-fucose, L-arabinose, D-turanose, D-leucrose, and mixtures thereof. In particular embodiments, the sweetener composition can comprise D-psicose.

The sweetener composition of the present disclosure can also contain other additional ingredients, such as a solubilizing or a bulking agent. Exemplary solubilizing or bulking agent includes maltodextrin, dextrose-maltodextrin blends, hydroxypropylmethyl cellulose, carboxymethyl cellulose, polyvinylpyrrolidone, and combinations thereof.

The sweetener composition of the present disclosure may also contain an artificial nutritive sweetener, a sweetness enhancer, and/or a binding or an anti-caking agent.

Exemplary artificial sweeteners include, but are not limited to, saccharin, cyclamate, aspartame, neotame, advantame, acesulfame potassium, sucralose, mixtures thereof.

Suitable sweetness enhancers include any of those known in the art. Exemplary sweetness enhancers include, but are not limited to sugar alcohol sweetness enhancer (e.g., erythritol, sorbitol, mannitol, xylitol, lactitol, isomalt, malitol, and mixtures thereof), or rare sugar sweetness enhancer (D-psicose, D-allose, L ribose, D-tagatose, L glucose, L-fucose, L-arabinose, D-turanose, D-leucrose, and mixtures thereof).

In some embodiments, the sweetness enhancer is a salt based (e.g., NaCl or potassium sorbate) or a benzoic acid based sweetness enhancer (e.g., potassium benzoate).

The sweetener composition of the present disclosure can be provided in various forms. In certain embodiments, the sweetener composition can be in a solid form, e.g., as a granular or powder composition for use as a tabletop sweetener, or alternatively for use in food products.

In some embodiments, the sweetener composition of the present disclosure can be provided as a liquid form, e.g., as a concentrate. The concentrate can contain additional other ingredients known in the art.

The sweetener composition described herein, whether in a solid form (e.g., powder or granules), or a liquid form (e.g., concentrate), can be utilized in reduced sugar, or in any food or beverage products typically including a sweetener. In some embodiments, the sweetener composition described herein is suitable for use in cooking, baking, or for preparing sweetened toppings (e.g., icings), or for use in jellies, jams, preserves, Instant QUAKER Oats, and the like. It is similarly suitable for use in frozen dairy products, such as ice cream, as well as in whipped toppings.

Beverage Products

The sweetener composition of present disclosure may be used in a beverage product. In some embodiments, the beverage product is a ready-to-drink beverage or a beverage concentrate. In some embodiments, the beverage product can have fewer than about 200 calories per 8 oz serving, fewer than about 150 calories per 8 oz serving, fewer than about 100 calories per 8 oz serving, fewer than about 70 calories per 8 oz serving, fewer than about 50 calories per 8 oz serving, fewer than about 10 calories per 8 oz serving, or fewer than about 5 calories per 8 oz serving.

Ready-to-Drink Beverages

Certain embodiments of the present disclosure are directed to ready-to-drink beverages comprising water, a sweetener composition of present disclosure, optionally an acidulant, and optionally a flavorant.

A ready-to-drink beverage comprising the sweetener composition will include the flavor-modifying composition comprising one or more, or two or more, or three or more, or four more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. These compounds, when present in a given ready-to-drink beverage, can be present in the amounts specified below.

For example, in some embodiments, furfural can be present in the ready-to-drink beverage in a concentration ranging from about 1 ppb to about 50 ppb, from about 1 ppb to about 40 ppb, from about 1 ppb to about 30 ppb, from about 1 ppb to about 20 ppb, from about 5 ppb to about 20 ppb, from about 10 ppb to about 20 ppb, from about 10 ppb to about 15 ppb, or in an amount of about 10 ppb, about 11 ppb, about 12 ppb, about 13 ppb, about 14 ppb, about 15 ppb, about 16 ppb, about 17 ppb, about 18 ppb, about 19 ppb, about 20 ppb, about 21 ppb, about 22 ppb, about 23 ppb, about 24 ppb, about 25 ppb, about 26 ppb, about 27 ppb, about 28 ppb, about 29 ppb, or about 30 ppb, about 31 ppb, about 32 ppb, about 33 ppb, about 34 ppb, about 35 ppb, about 26 ppb, about 37 ppb, about 38 ppb, about 39 ppb, or about 40 ppb. In some embodiments, the furfural can be present in the ready-to-drink beverage at a concentration of about 13 ppb.

In some embodiments, 4-hexen-1-ol can be present in the ready-to-drink beverage in a concentration ranging from about 0.1 ppb to about 10 ppb, from about 0.1 ppb to about 5 ppb, from about 0.1 ppb to about 4 ppb, from about 0.1 ppb to about 3 ppb, from about 0.5 ppb to about 3 ppb, from about 1 ppb to about 3 ppb, from about 1 ppb to about 2 ppb, or in an amount of about 1 ppb, about 1.1 ppb, about 1.2 ppb, about 1.3 ppb, about 1.4 ppb, about 1.5 ppb, about 1.6 ppb, about 1.7 ppb, about 1.8 ppb, about 1.9 ppb, or about 2 ppb. In some embodiments, the 4-hexene-1-ol can be present in the ready-to-drink beverage at a concentration of about 1.3 ppb.

In some embodiments, trans-2,4-hexadienal can be present in the ready-to-drink beverage in a concentration ranging from about 0.5 ppb to about 20 ppb, from about 0.5 ppb to about 15 ppb, from about 0.5 ppb to about 10 ppb, from about 1 ppb to about 10 ppb, from about 1 ppb to about 7.5 ppb, from about 2.5 ppb to about 7.5 ppb, or in an amount of about 2.5 ppb, about 3 ppb, about 3.5 ppb, about 4 ppb, about 4.5 ppb, about 5 ppb, about 5.5 ppb, about 6 ppb, about 6.5 ppb, about 7 ppb, or about 7.5 ppb. In some embodiments, the trans-2,4-hexadienal can be present in the ready-to-drink beverage at a concentration of about 5 ppb.

In some embodiments, 2,4-hexadien-1-ol can be present in the ready-to-drink beverage in a concentration ranging from about 0.1 ppb to about 20 ppb, from about 0.5 ppb to about 20 ppb, from about 0.5 ppb to about 15 ppb, from about 0.5 ppb to about 10 ppb, from about 1 ppb to about 10 ppb, from about 1 ppb to about 6 ppb, from about 2 ppb to about 6 ppb, or in an amount of about 0.5 ppb, about 0.6 ppb, about 0.7 ppb, about 0.8 ppb, about 0.9 ppb, about 1 ppb, about 2 ppb, about 2.5 ppb, about 3 ppb, about 3.5 ppb, about 4 ppb, about 4.5 ppb, about 5 ppb, about 5.5 ppb, or about 6 ppb. In some embodiments, the 2,4-hexadien-1-ol can be present in the ready-to-drink beverage at a concentration of about 4 ppb.

In some embodiments, 5-methyl-furfural can be present in the ready-to-drink beverage in a concentration ranging from about 0.1 ppb to about 10 ppb, from about 0.1 ppb to about 5 ppb, from about 0.1 ppb to about 4 ppb, from about 0.1 ppb to about 3 ppb, from about 0.5 ppb to about 3 ppb, from about 0.5 ppb to about 1 ppb, or in an amount of about 0.1 ppb, about 0.2 ppb, about 0.3 ppb, about 0.4 ppb, about 0.5 ppb, about 0.6 ppb, about 0.7 ppb, about 0.8 ppb, about 0.9 ppb, about 1 ppb, about 1.2 ppb, about 1.4 ppb, about 1.6 ppb, about 1.8 ppb, about 2 ppb, about 2.2 ppb, about 2.4 ppb, about 2.6 ppb, about 2.8 ppb, or about 3 ppb. In some embodiments, the 5-methyl-furfural can be present in the ready-to-drink beverage at a concentration of about 0.7 ppb.

In some embodiments, delta-tetradecalactone can be present in the ready-to-drink beverage in a concentration ranging from about 0.01 ppb to about 1 ppb, from about 0.01 ppb to about 0.5 ppb, from about 0.01 ppb to about 0.4 ppb, from about 0.01 ppb to about 0.3 ppb, from about 0.05 ppb to about 0.3 ppb, from about 0.075 ppb to about 0.3 ppb, from about 0.09 ppb to about 0.2 ppb, or in an amount of about 0.05 ppb, about 0.06 ppb, about 0.07 ppb, about 0.08 ppb, about 0.09 ppb, about 0.1 ppb, about 0.12 ppb, about 0.13 ppb, about 0.14 ppb, or about 0.15 ppb. In some embodiments, the delta-tetradecalactone can be present in the ready-to-drink beverage at a concentration of about 0.1 ppb.

In some embodiments, cis-4-methyl-5-butyldihydro-2(3H)-furanone and/or trans-4-methyl-butyldihydro-2(3H)-furanone can be present in the ready-to-drink beverage in a concentration ranging from about 0.01 ppb to about 5 ppb, from about 0.01 ppb to about 3 ppb, from about 0.01 ppb to about 1 ppb, from about 0.01 ppb to about 0.5 ppb, from about 0.1 ppb to about 0.5 ppb, or in an amount of about 0.1 ppb, about 0.15 ppb, about 0.2 ppb, about 0.25 ppb, about 0.3 ppb, about 0.35 ppb, about 0.4 ppb, about 0.45 ppb, about 0.5 ppb, about 0.6 ppb, about 0.7 ppb, about 0.8 ppb, about 0.9 ppb, about 1 ppb, about 1.1 ppb, about 1.2 ppb, about 1.3 ppb, about 1.4 ppb, about 1.5 ppb, about 1.6 ppb, about 1.7 ppb, about 1.8 ppb, about 1.9 ppb, or about 2 ppb. In some embodiments, the cis-4-methyl-5-butyldihydro-2

(3H)-furanone and/or trans-4-methyl-butyldihydro-2(3H)-furanone can be present in the ready-to-drink beverage at a concentration of about 0.3 ppb.

In some embodiments, butyl acetate can be present in the ready-to-drink beverage in a concentration ranging from about 0.1 ppb to about 10 ppb, from about 0.1 ppb to about 5 ppb, from about 0.1 ppb to about 4 ppb, from about 0.1 ppb to about 3 ppb, from about 0.5 ppb to about 3 ppb, from about 0.5 ppb to about 1 ppb, or in an amount of about 0.1 ppb, about 0.2 ppb, about 0.3 ppb, about 0.4 ppb, about 0.5 ppb, about 0.6 ppb, about 0.7 ppb, about 0.8 ppb, about 0.9 ppb, about 1 ppb, about 1.2 ppb, about 1.4 ppb, about 1.6 ppb, about 1.8 ppb, about 2 ppb, about 2.2 ppb, about 2.4 ppb, about 2.6 ppb, about 2.8 ppb, or about 3 ppb. In some embodiments, the butyl acetate can be present in the ready-to-drink beverage at a concentration of about 0.8 ppb.

In some embodiments, 3-methylbutanol can be present in the ready-to-drink beverage in a concentration ranging from about 0.1 ppb to about 50 ppb, from about 0.1 ppb to about 40 ppb, from about 0.1 ppb to about 10 ppb, from about 0.1 ppb to about 5 ppb, from about 0.1 ppb to about 4 ppb, from about 0.1 ppb to about 3 ppb, from about 0.5 ppb to about 3 ppb, from about 1 ppb to about 3 ppb, from about 1 ppb to about 2 ppb, or in an amount of about 1 ppb, about 1.1 ppb, about 1.2 ppb, about 1.3 ppb, about 1.4 ppb, about 1.5 ppb, about 1.6 ppb, about 1.7 ppb, about 1.8 ppb, about 1.9 ppb, about 2 ppb, about 3 ppb, about 4 ppb, about 5 ppb, about 6 ppb, about 7 ppb, about 8 ppb, about 9 ppb, about 10 ppb, about 15 ppb, about 20 ppb, about 25 ppb, about 30 ppb, about 35 ppb, about 40 ppb, about 45 ppb, or about 50 ppb. In some embodiments, the 3-methylbutanol can be present in the ready-to-drink beverage at a concentration of about 1.6 ppb.

In some embodiments, ethyl octanoate can be present in the ready-to-drink beverage in a concentration ranging from about 0.1 ppb to about 10 ppb, from about 0.1 ppb to about 5 ppb, from about 0.1 ppb to about 4 ppb, from about 0.1 ppb to about 3 ppb, from about 0.1 ppb to about 2 ppb, or from about 0.1 ppb to about 1 ppb, or in an amount of about 0.1 ppb, about 0.2 ppb, about 0.3 ppb, about 0.4 ppb, about 0.5 ppb, about 0.6 ppb, about 0.7 ppb, about 0.8 ppb, about 0.9 ppb, or about 1 ppb. In some embodiments, the ethyl octanoate can be present in the ready-to-drink beverage at a concentration of about 0.5 ppb.

In some embodiments, ethyl decanoate can be present in the ready-to-drink beverage in a concentration ranging from about 0.1 ppb to about 20 ppb, from about 0.5 ppb to about 20 ppb, from about 0.5 ppb to about 15 ppb, from about 0.5 ppb to about 10 ppb, from about 1 ppb to about 10 ppb, from about 1 ppb to about 6 ppb, from about 2 ppb to about 6 ppb, or in an amount of about 0.1 ppb, about 0.2 ppb, about 0.3 ppb, about 0.4 ppb, about 0.5 ppb, about 0.6 ppb, about 0.7 ppb, about 0.8 ppb, about 0.9 ppb, about 1 ppb, about 2 ppb, about 2.5 ppb, about 3 ppb, about 3.5 ppb, about 4 ppb, about 4.5 ppb, about 5 ppb, about 5.5 ppb, or about 6 ppb. In some embodiments, the ethyl decanoate can be present in the ready-to-drink beverage at a concentration of about 3 ppb.

In some embodiments, ethyl hexadecanoate can be present in the ready-to-drink beverage in a concentration ranging from about 0.1 ppb to about 10 ppb, from about 0.1 ppb to about 5 ppb, from about 0.1 ppb to about 4 ppb, from about 0.1 ppb to about 3 ppb, from about 0.5 ppb to about 3 ppb, from about 1 ppb to about 3 ppb, from about 1 ppb to about 2 ppb, or in an amount of about 1 ppb, about 1.1 ppb, 1.2 ppb, about 1.3 ppb, about 1.4 ppb, about 1.5 ppb, about 1.6 ppb, about 1.7 ppb, about 1.8 ppb, about 1.9 ppb, or about 2 ppb. In some embodiments, the ethyl hexadecanoate can be present in the ready-to-drink beverage at a concentration of about 1.3 ppb.

In some embodiments, 2-methylbutanol can be present in the ready-to-drink beverage in a concentration ranging from about 0.1 ppb to about 50 ppb, from about 0.1 ppb to about 40 ppb, from about 0.1 ppb to about 10 ppb, from about 0.1 ppb to about 5 ppb, from about 0.1 ppb to about 4 ppb, from about 0.1 ppb to about 3 ppb, from about 0.5 ppb to about 3 ppb, from about 1 ppb to about 3 ppb, from about 1 ppb to about 2 ppb, or in an amount of about 1 ppb, about 1.1 ppb, about 1.2 ppb, about 1.3 ppb, about 1.4 ppb, about 1.5 ppb, about 1.6 ppb, about 1.7 ppb, about 1.8 ppb, about 1.9 ppb, about 2 ppb, about 3 ppb, about 4 ppb, about 5 ppb, about 6 ppb, about 7 ppb, about 8 ppb, about 9 ppb, about 10 ppb, about 15 ppb, about 20 ppb, about 25 ppb, about 30 ppb, about 35 ppb, about 40 ppb, about 45 ppb, or about 50 ppb. In some embodiments, the 2-methylbutanol can be present in the ready-to-drink beverage at a concentration of about 1.6 ppb.

Suitable acidulants include, but are not limited to phosphoric acid, citric acid, malic acid, tartaric acid, lactic acid, formic acid, ascorbic acid, fumaric acid, gluconic acid, succinic acid, maleic acid, adipic acid, and mixtures thereof.

Suitable flavorants include, but are not limited to a cola flavorant, a tea flavorant, a caramel flavorant, a coffee flavorant, a citrus flavorant (e.g. a lemon flavorant, a lime flavorant, an orange flavorant, a grapefruit flavorant, a mandarin orange flavorant, a tangerine flavorant, a tangelo flavorant, or a combination of any of the foregoing), an herbal flavorant, a berry flavoring (e.g., a flavorant derived from one or more of Barbados cherry, bearberry, blackberry, blueberry, boysenberry, cherry, choke cherry, cloudberry, cranberry, current, date, dewberry, elderberry, grape, gooseberry, huckleberry, loganberry, olallieberry, mulberry, raisin, plains berry, prairie berry, raspberry, saskatoon berry, salmonberry, seabuckthorn berry, sloe berry, strawberry, thimbleberry, thornberry, wineberry, whortleberry, or a combination of any of the foregoing), a botanical flavorant (e.g. one or more flavors derived from a part of a plant other than the fruit, including flavors derived from essential oils and extracts of nuts, bark, roots and leaves along with synthetically prepared flavors made to simulate botanical flavors derived from natural sources), and mixtures thereof.

Water is a basic ingredient in beverage products, typically being the vehicle or primary liquid portion in which the remaining ingredients are dissolved, emulsified, suspended or dispersed. Purified water can be used in the manufacture of certain embodiments of the beverages disclosed here, and water of a standard beverage quality can be employed in order not to adversely affect beverage taste, odor, or appearance. The water typically will be clear, colorless, free of objectionable minerals, tastes and odors, free from organic matter, low in alkalinity and of acceptable microbiological quality based on industry and government standards applicable at the time of producing the beverage.

In certain embodiments, water can be present at a level of from about 10 wt % to about 99.9 wt % in beverage products. In certain beverage embodiments, the quantity of water can range from about 80 wt % to about 99.9 wt % of the beverage.

In certain embodiments, the ready-to-drink beverage comprises a non-nutritive sweetener in an amount ranging from about 1 ppm to about 1000 ppm (e.g., about 1 ppm, about 10 ppm, about 50 ppm, about 100 ppm, about 200 ppm, about 300 ppm, about 400 ppm, about 500 ppm, about 600 ppm, about 700 ppm, about 800 ppm, about 900 ppm, about 1000 ppm or any ranges between the recited values), depending upon the particular non-nutritive sweetener(s) being used and the desired level of sweetness in the beverage.

In certain embodiments, the ready-to-drink beverage can also include one or more salts. The salt concentration can range from about 100 ppm to about 1000 ppm, or from about 200 ppm to about 800 ppm. In particular embodiments, the salt can be sodium chloride. In certain embodiments, the beverage composition can be completely or substantially salt free.

In some embodiments, caffeine can be added to the beverage. In other embodiments, the beverage is substantially caffeine free, or is caffeine free.

In certain embodiments, the ready-to-drink beverage can further comprise other ingredients such as antioxidants, food grade acids, and food grade bases. Other beverage components such as colors, preservatives, carbon dioxide, buffering salts, and the like, can also be present.

Suitable food grade acids are water soluble organic acids and their salts and include, for example, phosphoric acid, sorbic acid, ascorbic acid, benzoic acid, citric acid, tartaric acid, propionic acid, butyric acid, acetic acid, succinic acid, glutaric acid, maleic acid, malic acid, valeric acid, caproic acid, malonic acid, aconitic acid, potassium sorbate, sodium benzoate, sodium citrate, amino acids, and combinations of any of them. Such acids are suitable for adjusting the pH of the food or beverage.

Suitable food grade bases are sodium hydroxide, potassium hydroxide, and calcium hydroxide. Such bases also are suitable for adjusting the pH of a food or beverage.

In certain embodiments, the ready-to-drink beverages can be carbonated and non-carbonated soft drinks, fountain beverages, frozen ready-to-drink beverages, coffee, tea, and other brewed beverages, dairy beverages, flavored waters, enhanced waters, juices such as fruit juice (including diluted and ready to drink concentrated juices), fruit juice-flavored drinks, sport drinks, smoothies, functionally enhanced beverages such as caffeinated energy drinks, and alcoholic products.

Beverage products can have any of numerous different specific formulations or constituents. The formulation of a beverage product can vary, depending upon such factors as the product's intended market segment, its desired nutritional characteristics, flavor profile, and the like. Thus further ingredients can be added to the formulation of a particular beverage product. Further ingredients include, but are not limited to, one or more additional sweeteners in addition to any sweetener already present, electrolytes, vitamins, flavor enhancers, carbonation, preservatives, or any combination thereof. These ingredients can be added to any of the beverage compositions to vary the taste, mouthfeel, and/or nutritional values of the beverage composition.

Preservatives may be used in certain food or beverage products. As used here, the term "preservatives" include all suitable preservatives approved for use in beverage compositions, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives may be used in amounts not exceeding mandated maximum levels under applicable laws and regulations.

In particular embodiments, the ready-to-drink beverage is a cola-flavored carbonated beverage, containing, amongst other things, water, sweetener, kola nut extract and/or other flavorings, caramel coloring, phosphoric acid, optionally caffeine, and optionally other ingredients. Additional and alternative suitable ingredients will be recognized by those skilled in the art given the benefit of this disclosure.

Carbonation in the form of carbon dioxide can be added for effervescence. Any of the techniques and carbonating equipment known in the art for carbonating beverages can be employed. Carbon dioxide can enhance beverage taste and appearance and may aid in safeguarding the beverage purity by inhibiting and/or destroying objectionable bacteria. In certain embodiments, for example, the beverage can have a $CO_2$ level up to about 4.0 volumes carbon dioxide. Other embodiments can have, for example, from about 0.5 to about 5.0 volumes of carbon dioxide. As used herein, one volume of carbon dioxide refers to the amount of carbon dioxide absorbed by a given quantity of a given liquid, such as water, at 60° F. (16° C.) and one atmospheric pressure. A volume of gas occupies the same space as does the liquid by which it is dissolved. The carbon dioxide content can be selected by those skilled in the art based on the desired level of effervescence and the impact of the carbon dioxide on the taste or mouthfeel of the beverage.

In some embodiments, the ready-to-drink beverage can have fewer than about 200 calories per 8 oz serving, fewer than about 150 calories per 8 oz serving, fewer than about 100 calories per 8 oz serving, fewer than about 70 calories per 8 oz serving, fewer than about 50 calories per 8 oz serving, fewer than about 10 calories per 8 oz serving, or fewer than about 5 calories per 8 oz serving.

Beverage Concentrates and Syrups

In some embodiments, a beverage concentrate or syrup can be prepared directly from the sweetener composition of present disclosure.

In some embodiments, the sweetener composition of present disclosure can be further diluted with water or other appropriate diluent to form a beverage concentrate or syrup.

A concentrate or syrup comprising the sweetener composition will include the flavor-modifying composition comprising one or more, or two or more, or three or more, or four more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, trans-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof. In certain embodiments, these compounds, when present in a given concentrate or syrup, can be present in the amounts specified below.

For example, in some embodiments, furfural can be present in the concentrate or syrup in an amount ranging from about 1 ppb to about 10,000 ppb, from about 1 ppb to about 7500 ppb, or from about 75 ppb to about 5000 ppb.

In some embodiments, 4-hexen-1-ol can be present in the syrup or concentrate in an amount ranging from about 0.1 ppb to about 1000 ppb, from about 0.1 to about 750 ppb, or from about 8 ppb to about 500 ppb.

In some embodiments, trans-2,4-hexadienal can be present in the concentrate or syrup in an amount ranging from about 1 ppb to about 5000 ppb, from about 10 ppb to about 2500 ppb, or from about 30 ppb to about 2000 ppb.

In some embodiments, 2,4-hexadien-1-ol can be present in the concentrate or syrup in an amount ranging from 1 ppb to about 5000 ppb, from about 10 ppb to about 2500 ppb, or from about 20 ppb to about 1500 ppb.

In some embodiments, 5-methyl-furfural can be present in the concentrate or syrup in an amount ranging from about 1 ppb to about 1000 ppb, from about 1 ppb to about 500 ppb, from about 1 ppb to about 300 ppb, or from about 4 ppb to about 250 ppb.

In some embodiments, delta-tetradecalactone can be present in the concentrate or syrup in an amount ranging from 0.1 ppb to about 100 ppb, and in certain embodiments, from about 0.1 ppb to about 20 ppb.

In some embodiments, cis-4-methyl-5-butyldihydro-2(3H)-furanone and/or trans-4-methyl-butyldihydro-2(3H)-furanone can be present in the syrup or concentrate in an amount ranging from about 1 ppb to about 1000 ppb, from about 1.5 ppb to about 300 ppb, or from about 1.5 ppb to about 100 ppb.

In some embodiments, butyl acetate can be present in syrup or concentrate in an amount ranging from about 1 ppb to about 500 ppb, or from about 200 ppb to about 450 ppb.

In some embodiments, 3-methylbutanol can be present in syrup or concentrate in an amount ranging from about 1 ppb to about 10,000 ppb, from about 1 ppb to about 5,000 ppb, from about 1 ppb to about 1000 ppb, or from about 10 ppb to about 600 ppb.

In some embodiments, ethyl octanoate can be present in the concentrate or syrup in an amount ranging from 1 ppb to about 500 ppb or from about 3 to about 200 ppb.

In some embodiments, ethyl decanoate can be present in the syrup or concentration in an amount ranging from about 10 ppb to about 2500 ppb or from about 15 ppb to about 1200 ppb.

In some embodiments, ethyl hexadecanoate can be present in the syrup or concentrate in an amount 1 ppb to about 1000 ppb or from about 8 ppb to about 500 ppb.

In some embodiments, 2-methylbutanol can be present in the syrup or concentrate in an amount ranging from about 1 ppb to about 10,000 ppb, from about 1 to about 5000 ppb, from about 1 ppb to about 1000 ppb, or from about 10 ppb to about 600 ppb.

In certain embodiments, the beverage concentrate or syrup may contain a non-nutritive sweetener in an amount up to 600,000 ppm depending upon the particular non-nutritive sweetener being used and the desired level of sweetness for the beverage concentrate.

Additional and alternative suitable ingredients for beverage concentrate can be readily recognized by those skilled in the art. For example, one or more salts can be included in the beverage concentrate in an amount ranging from about 600 ppm to about 6000 ppm, or from about 1200 ppm to about 2400 ppm. In certain embodiments, beverage concentrates can be completely or substantially salt free.

In some embodiments, ready-to-drink beverage can be prepared from a beverage concentrate by adding further volumes of water to the concentrate. For example, a ready-to-drink beverage can be prepared from a beverage concentrate by combining approximately 1 part concentrate with about 3 to about 7 parts water. In one embodiment, the ready-to-drink beverage can be prepared by combining 1 part concentrate with 5 parts water.

In certain embodiments, the present disclosure also includes a kit comprising the concentrate or syrup. In addition to the concentrate or syrup, the kit can comprise any of the additional elements required for preparing a syrup (from the concentrate) or beverage (from the concentrate or syrup), such as flavorings, acids, antioxidants, etc., exclusive of, or optionally including, any additional water that might be required to dilute the concentrate or syrup. The kit can further include instructions for preparing a syrup or a beverage. In certain embodiments the kit can be provided to a beverage bottler or to a beverage retailer.

In other embodiments, the present disclosure includes a kit comprising a syrup. In certain embodiments, the kit can include the syrup as well as instructions for preparing a beverage from the syrup. For example, when provided to a bottler, the kit can contain instructions for preparing beverages on a commercial scale. When provided to a retailer, the kit can contain instructions for preparing beverages using a post-mix delivery system, such as calibration instructions, etc.

The present disclosure further include kits comprising one or more pods, cartridges, or other containers adapted to store a sufficient quantity of the syrup to prepare a single- or multiple-serve beverage from the syrup. In some embodiments, the kit can further include a beverage-dispensing apparatus adapted to receive the one or more pods or cartridges, wherein, upon activation by a user, the beverage dispensing apparatus combines the contents of one pod or cartridge with an appropriate volume of optionally carbonated water, or other diluent, to provide a single- or multiple-serve beverage. In still further embodiments, the kit can include instructions for operating the beverage-dispensing apparatus, cleaning the apparatus, and refilling and/or recycling spent pods or cartridges. In certain embodiments, the beverage-dispensing apparatus can be suitable for use in a commercial setting, such as a retail environment. In other embodiments, the beverage dispensing apparatus can be suitable for home or "on the go" use. Pods and cartridges adapted to store syrup for preparing single- or multiple-serve beverages as well as beverage dispensing apparatuses adapted to receive pods and cartridges for preparing a single- or multiple-serve beverage, both for home and commercial use, are known to those of ordinary skill in the art.

Food Products

The sweetener composition of present disclosure can also be used in food products. The food products include, but are not limited to oatmeal, cereal, baked goods, cookies, crackers, cakes, brownies, breads, snack foods (e.g., snack bars), potato or tortilla chips, popcorn, rice cakes, and other grain-based food products.

EXAMPLES

Example 1—Preparing Sweetener Compositions Using a Charred Oak Barrel

A concentrated aqueous *stevia* composition was prepared by dissolving 8 wt % of a total steviol glycoside composition (TSG), in water. The TSG was a blend of rebaudioside A, stevioside and rebaudioside D described as "Composition 1" in Table 2. The resulting aqueous *stevia* composition was divided and stored in: a) a medium charred oak barrel; and b) a glass bottle, at an ambient temperature for 4 weeks. After 4 weeks, an aliquot from both the oak barrel and the glass bottle was taken and was diluted with a solution containing 0.1 wt % citric acid to a final concentration of 400 ppm of total steviol glycoside concentration for taste testing.

Example 2—Taste Testing

A tasting panel of 27 trained panelists conducted the taste testing of the two diluted *stevia* solutions prepared in Example 1. They were asked to compare the two solutions without being told their storage conditions. Tasters were asked not to eat at least 1 hour before tasting and to rinse with AQUAFINA water at least 5 times between tasting each sample. On a scale of 0-7 ("0" being no difference, and "7" being strongest difference), 100% of panelists found an average degree of difference of 3.33 between the two solutions, which is between "slight to moderate difference" and "moderate difference." Panelists described the *stevia* composition stored in the oak barrel as being less bitter, less astringent, and having more rounded and balanced sweetness. A score of 3.33 indicated a reduction of about 50% in bitterness and/or astringency of the oak barrel solution from example 1.

Example 3—Preparing Sweetener Compositions Using an Oak Barrel

A concentrated aqueous *stevia* composition was prepared by dissolving 8 wt % of the total steviol glycoside composition (TSG) described as Composition 1 (Table 2), in water. The resulting aqueous *stevia* composition was divided and stored in: a) a medium charred oak barrel; and b) a glass bottle, at an ambient temperature. Aliquots were taken from each of the oak barrel and glass bottle at 0.5 weeks, 1 week, 2 weeks, 3 weeks, 4 weeks, 5 weeks, 6 weeks, and 6.5 weeks. Samples were diluted with a solution containing 2.8 wt % sugar and 0.1 wt % citric acid to a final concentration of 200 ppm total steviol glycoside concentration for taste testing and analytical study.

Example 4—Barrel Ageing Study

A tasting panel of 5 subject matter experts in *stevia* conducted the taste testing of the *stevia* solutions prepared in Example 3. They were asked: a) to describe when a positive change in any one or all of bitterness, bitter linger, sweet onset, sugar like taste, roundness, and overall sugar quality was noticed as compared to the reference solution (i.e., the solution from the glass bottle storage); and b) to describe taste change over different storage time periods.

The panelists found a significant change as early as 0.5 weeks. They described changes being less sweet linger, less astringency and less bitter aftertaste.

After 1 week, the panelists found that the solution has increased sweetness and more sugar-like taste with a smoother aftertaste.

After 2 weeks, the panelists found that the oak-derived solution has increased sweetness, less astringency especially in the aftertaste and more rounded even compared to week 1.

After 3 weeks, the panelists found similar changes as observed for week 2, with an improved backend sweet taste, i.e., increased overall sweet quality.

After 4 weeks, the panelists found that the solution had an exceptional increase in sweet quality, increased upfront sweetness with a cleaner back end profile.

After 5 weeks, the panelists found that the solution had an exceptional increase in sweet quality, increased upfront sweetness with a cleaner back end profile, which was similar to week 4. The panelists also found that the solution had higher oak notes.

Finally, after 6 weeks, the panelists found that the solution had a good back end sweet taste with fruity clean finish.

Aliquots obtained from all time points as described in Example 3 were analyzed by GCMS and LCMS. Two GC chromatograms are included as FIGS. 3 and 4.

The analytical studies found that the *stevia* composition stored in an oak barrel contained higher concentration of volatile compounds, as compared to the reference composition. Also, the longer the oak barrel storing time period, the higher the concentration of these volatile compounds (see FIGS. 3 and 4).

The volatile compounds detected by GCMS included furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, and trans-4-methyl-5-butyldihydro-2(3H)-furanone.

HPLC (reversed phase) studies found that the *stevia* composition stored in an oak barrel did not contain any detectable amount of non-volatile compounds (see FIG. 5). The chromatographic conditions are shown below and in Table 3:

Instrument: Agilent 6500 QTOF
Column: Waters ACQUITY UPLC BEH C18 2.1×100 mm 1.7 µm
Column temperature: 40° C.
Column pressure: initial pressure about 700 bar.
Solvent Gradient:

TABLE 3

| Time (min) | A (%) | B (%) | Flow (mL/min) | Max. Pressure Limit (bar) |
|---|---|---|---|---|
| 0.0 | 99.0 | 1.0 | 0.6 | 1200.0 |
| 8.0 | 2.0 | 98.0 | 0.6 | 1200.0 |
| 9.5 | 2.0 | 98.0 | 0.6 | 1200.0 |
| 10.0 | 99.0 | 1.0 | 0.6 | 1200.0 |
| 12.0 | 99.0 | 1.0 | 0.6 | 1200.0 |

Mobile Phase for Positive-Mode:
A: water 0.1% formic acid; and B: acetonitrile 0.1% formic acid.
Mobile Phase for Negative-Mode:
A: water 6.5 mM ammonium bicarbonate, and B: methanol/water (95:5) 6.5 mm ammonium bicarbonate.
Solvent flow rate: 0.6 ml/min
Injection volume: 5 µL.

Example 5—Preparing Sweetener Compositions Using Oak Spirals

A concentrated aqueous *stevia* composition was prepared by dissolving 8 wt % of the total steviol glycoside composition (TSG) described as Composition 1 (Table 2), in water. 1000 mL of the resulting aqueous *stevia* composition was transferred into two 500 mL glass containers. Into the first glass container, a medium charred (toast) French Oak spiral was added. Into the second container, a medium charred (toast) American oak spiral was added. Also, some of the resulting aqueous *stevia* composition was transferred into a glass container without adding any oak spirals. The containers were stored at ambient temperature for 1 week. After 1 week, an aliquot from each container was taken and was diluted with a solution containing 2.8 wt % sugar and 0.1 wt % citric acid to a final concentration of 200 ppm of total steviol glycoside concentration for taste testing. The *stevia* solutions before dilution had a significant dark brown color and noticeable oak odor.

Example 6-Taste Testing and Analytical Study

A tasting panel of 27 expert subject matter experts in *stevia* conducted the taste testing of the *stevia* solutions prepared in Example 5. They were asked to compare the solutions to a reference solution (i.e., *stevia* solution from concentrated *stevia* that was stored in a glass container without oak spirals or other types of oak wood contact). A significant taste difference was experienced by panelists comparing the *stevia* solutions of Example 5 and the reference solution. The taste improvement was similar to those described in Examples 4 above, except that the *stevia* solutions prepared in Example 5 have significant oak flavor.

The *stevia* solutions were also analyzed by GCMS and LCMS, which confirmed that the presence of the volatile compounds in the *stevia* solution stored in oak barrels as described in Examples 3 and 4 above, along with hexanal.

Example 7—Identification and Quantification of Compounds Obtained from Aged Oak Barrels A 3 liter medium charred oak barrel was treated by filling it with deionized water at 95° C., letting it sit for 1 hour, discarding the water, and then repeating the process two additional times.

A preserved aqueous *stevia* composition was prepared by dissolving 8 wt % of a blend containing 16% rebaudioside D, 42% rebaudioside A, 25% stevioside, 12% rebaudioside C, and 15% trace level *stevia* glycosides in water with 0.32 wt % potassium sorbate.

Two liters of the preserved aqueous *stevia* composition was added to the treated oak barrel and stored at 21° C. Samples were taken weekly and analyzed by GCMS. After 6 weeks, the preserved aqueous *stevia* composition was transferred from the oak barrel into a high density polyethylene (HDPE) container, and additional samples were analyzed by GCMS. The compounds identified by GCMS after 6 weeks were quantified in parts per million. The compounds identified and quantified by GCMS are listed in Table 4 with the concentrations present in the 8 wt % preserved aqueous *stevia* composition ("*stevia* concentrate") and two beverages prepared by diluting the 8 wt % preserved aqueous *stevia* composition to either 400 ppm ("400 ppm *stevia*") or 200 ppm ("200 ppm *stevia*").

for receptor biology studies. For the first control sample ("Control 1 Base"), malic acid was added to a 0.32% aqueous potassium sorbate solution until the solution had a pH of 3.5. A second control sample ("Control 2 Base") consisting of a preserved acidified aqueous *stevia* composition ("*Stevia*") was prepared by dissolving 8 wt % of a blend containing 16% rebaudioside D, 42% rebaudioside A, 25% stevioside, 12% rebaudioside C, and 15% trace level steviol glycosides in a 0.32 wt % aqueous potassium sorbate solution and adding malic acid until the solution had a pH of 3.5.

Ten aqueous samples (Samples I-X) were prepared by adding one or more of the compounds listed in Table 4, in the concentration specified in Table 4 for the *stevia* concentrate, to the Control 2 Base ("FMP Mixture"). Table 4 lists the concentrations of compounds 3, 4, and 12 as 0.0 ppm for the *stevia* concentrate. However, compounds 3, 4, and 12 were added to the Control 2 Base at concentrations of 6.25 ppm, 1.17 ppm, and 0.1 ppm, respectively. The specific formulations are shown in Table 5.

TABLE 5

| Sample | FMP Mixture |
|---|---|
| Base solution without Stevia (Control 1 Base) | N/A |
| Base solution with Stevia (Control 2 Base) | N/A |
| I | 9 |
| II | 1, 9 |
| III | 1, 9, 10 |
| IV | 1, 9, 10, 12 |
| V | 1, 7, 9, 10, 12 |
| VI | 1, 4, 7, 9, 10, 12 |
| VII | 1, 4, 7, 8, 9, 10, 12 |
| VIII | 1, 4, 6, 7, 8, 9, 10, 12 |
| IX | 1, 3, 4, 6, 7, 8, 9, 10, 12 |
| X | 1, 2, 3, 4, 6, 7, 8, 9, 10, 12 |

TABLE 4

| Compound No. | Compound Name | Concentration in Stevia Concentrate (ppm) | Concentration in 400 ppm Stevia Beverage (ppm) | Concentration in 200 ppm Stevia Beverage (ppm) |
|---|---|---|---|---|
| 1 | Butyl Acetate | 0.43 | 0.0025 | 0.0012 |
| 2 | 3-Methylbutanol | 6.1 | 0.0349 | 0.0174 |
| 3 | (E,E)-2,4-Hexadienal | 0.0 | 0.0 | 0.0 |
| 4 | 4-Hexen-1-ol | 0.0 | 0.0 | 0.0 |
| 5 | Ethyl Octanoate | 0.03 | 0.0002 | 0.0001 |
| 6 | Furfural | 6.74 | 0.0385 | 0.0193 |
| 7 | 5-Methylfurfural | 0.49 | 0.0028 | 0.0014 |
| 8 | (E,E)-2,4-Hexadienol | 0.16 | 0.0009 | 0.0005 |
| 9 | Ethyl Decanoate | 0.04 | 0.0002 | 0.0001 |
| 10 | Trans-4-Methyl-5-butyldihydro-2(3H)-furanone | 0.29 | 0.0017 | 0.0008 |
| 11 | Cis-4-Methyl-5-butyldihydro-2(3H)-furanone | 0.0 | 0.0 | 0.0 |
| 12 | Ethyl Hexadecanoate | 0.0 | 0.0 | 0.0 |

Example 8—Receptor Biology Studies for Mixtures Containing *Stevia*

Two control samples and ten aqueous samples containing one or more compounds identified in Table 4 were prepared The control samples and samples I-X were tested for their ability to activate sweet taste receptors T1R2/T1R3, GLUT4, and Glucagon and bitter taste receptors T2R using a taste receptor internalization assay. Receptor activation and internalization was measured using images acquired by an IMAGEXPRESS Micro automated epifluorescence microscope (Molecular Devices Corporation). The images were analyzed with METAXPRESS 5.1 Workstation software, utilizing the Multiwaves Translocation Scoring analysis algorithm for nuclear and cytoplasmic segmentation. Curve fitting and parameter estimation were then analyzed with TIBCO SPOTFIRE.

Taste Receptor Internalization General Procedure:

The two control samples and Samples I-X were each serially diluted eight times at a ratio of 1:1 in water (1 part sample to 2 parts water) and dose response was determined by conducting a receptor internalization assay ("Ring Assay") on an H716 cell line with an HCl platform using the methods disclosed in PCT Patent Application Publication No. WO 2014/183041. Receptor internalization was measured at 5 and 15 minutes. $EC_{50}$ values and Maximum-Minimum ("Max-Min") values were calculated using SPOTFIRE software. Sweet, aftertaste, glucagon, and bitterness scoring were calculated using analysis of variance (ANOVA). A median value was then calculated by dividing the Max-Min value by the $EC_{50}$ value for all time points. The median values, which represent receptor activity, were then plotted on radar graphs, as shown in FIGS. 9A-9B, 10A-10B, 11A-11B, 12A-12B, 13, 14A-14B, 15A-15B, 16A-16B, 17A-17B, 18A-18B, and 19.

For ease of visualization, two samples are included in each graph to show the effect of certain "key" compounds. As shown in FIG. 9A, the Control 2 Base (base solution with stevia) resulted in an expected increase in activation of the sweet, aftertaste, and bitter receptors and decreased activation of the glucagon receptor as compared with the Control 1 Base (base solution without stevia). FIGS. 9A-9B, 10A-10B, 11A-11B, 12A-12B, 13, 14A-14B, 15A-15B, 16A-16B, 17A-17B, 18A-18B, and 19 show the effects of individual compounds and combinations of compounds on receptor activation. For example, FIG. 10A compares the receptor activity of an aqueous sample containing 10 of the compounds from Table 4 and stevia (Sample X) to the receptor activity of an aqueous sample containing 9 of the compounds from Table 4 and stevia (Sample IX). The differences in receptor responses for Sample IX and Sample X demonstrated the effect of compound 2 (3-methylbutanol), which was not present in Sample IX, on the taste profile of stevia. In particular, FIG. 10A indicates that compound 2 is a sweet/glucagon enhancer.

FIGS. 10B, 11A-11B, 12A-12B, and 13 show similar comparisons between Samples containing progressively one less compound from Table 4 (Sample IX through Sample I). For example, FIGS. 10B, 11A-11B, 12A-12B, and 13 contain radar graphs showing comparisons of the receptor activity between Sample IX and Sample VIII, Sample VIII and Sample VII, etc.

FIGS. 14A-14B, 15A-15B, 16A-16B, 17A-17B, 18A-18B, and 19 show the effect of each individual compound on receptor activity as compared to the effect of the compound in conjunction with one or more additional compounds.

The receptor activity for each of Samples I-X was also compared to the base solutions. The receptor activity for the Control 2 Base solution was first compared to the receptor activity of the Control 1 Base solution. Then, the receptor activity for each aqueous sample containing a specified combination of compounds was compared to the receptor activity of the Control 2 Base solution. The specific combination of compounds in each aqueous sample and the results are shown in Table 6.

TABLE 6

| Sample | FMP Mixture | Sweet T1R2/T1R3 | Glucagon | Aftertaste (GLUT4) | Bitter (25T2R) |
|---|---|---|---|---|---|
| Base solution without Stevia (Control 1 Base) | N/A | +/− | +/+ | +/− | +/− |
| Base solution with Stevia (Control 2 Base) | N/A | +/+ | +/− | +/+ | +/+ |
| I | 9 | +/+ | −/− | +/+ | +/+ |
| II | 1, 9 | +/− | +/+ | +/− | +/− |
| III | 1, 9, 10 | +/+ | +/+ | +/− | +/− |
| IV | 1, 9, 10, 12 | +/+ | +/− | +/+ | +/− |
| V | 1, 7, 9, 10, 12 | +/+ | −/− | +/− | +/+ |
| VI | 1, 4, 7, 9, 10, 12 | +/− | +/+ | +/+ | −/− |
| VII | 1, 4, 7, 8, 9, 10, 12 | +/− | −/− | +/+ | −/− |
| VIII | 1, 4, 6, 7, 8, 9, 10, 12 | +/+ | +/− | +/− | −/− |
| IX | 1, 3, 4, 6, 7, 8, 9, 10, 12 | −/− | −/− | +/− | −/− |
| X | 1, 2, 3, 4, 6, 7, 8, 9, 10, 12 | +/+/+ | +/+ | +/− | −/− |

Table 6 shows a comparison of the level of activation of the sweet, aftertaste, bitter, and glucagon receptors between the second control sample and the aqueous samples. The symbol "+/+" indicates that the tested sample exhibited the same receptor activity, or median value, as the control. The symbol "+/+/+" indicates that the tested sample exhibited greater than 1.5 times the receptor activity as the control, while "+/−" indicates that the tested sample exhibited less receptor activity than the control. Finally, the symbol "−/−" indicates that the receptor activity of the tested sample is equal to zero.

Overall, FIGS. 9A-9B, 10A-10B, 11A-11B, 12A-12B, 13, 14A-14B, 15A-15B, 16A-16B, 17A-17B, 18A-18B, and 19 show comparisons of receptor activity between different aqueous samples as well as the individual compounds listed in Table 4.

Example 9—Receptor Biology Studies with Sugar and Steviol Glycosides 100 mM samples of sucrose, sucralose, and high fructose corn syrup (HFCS) were prepared in Dulbecco's phosphate-buffered saline (D-PBS). An aqueous sample containing a *stevia* blend RA50 comprising 50% rebaudioside A, 30% stevioside, 10% rebaudioside C, and 10% trace level glycosides ("*stevia* blend 2"), and an aqueous sample containing 97% pure rebaudioside A were each prepared in DMSO at a concentration of 10 mM. These five samples were serially diluted at a ratio of 1:1 in water (1 part sample to 1 part water) and tested for their ability to activate the sweet taste receptors T1R2, T1R3, Glucagon, and GLUT4 in accordance with the procedures described in Example 8. The results are shown in FIG. 20.

Example 10—Receptor Biology Studies with Selected Compounds to Illicit a Target Response A base solution was prepared by dissolving 8 wt % of a blend containing 17 wt % rebaudioside D and 83 wt % RA50 (50% rebaudioside A, 30% stevioside, 10% rebaudioside C, and 10% trace level glycosides) ("*stevia* blend 3") in water and heating the mixture to between 70° C. and 99° C. for 5-50 minutes. The mixture was cooled to room temperature, followed by addition of 0.32 wt % potassium sorbate. Malic acid was then added until the solution had a pH of 3.5. A base solution without *stevia* was also prepared by adding malic acid to a 0.32 wt % aqueous potassium sorbate solution until the solution had a pH of 3.5.

Eleven aqueous samples were then prepared by combining the *stevia* blend 3 base solution with one or more of the compounds listed in Table 4. Sample XI contained a mixture of compounds 1, 2, 3, 4, 6, 7, 8, 9, 10, and 12 (referred to as "M10") at the same concentrations as in Example 8. The specific combinations of compounds for Samples XII-XXI are shown in Table 7 along with the concentrations of each compound.

The eleven aqueous samples and the two base solutions were tested for their ability to activate the sweet taste receptors T1R2/T1R3, GLUT4, and Glucagon and the bitter taste receptors T2R in accordance with the procedures described in Example 8. The results are shown in FIGS. 21, 22, 23, 24, 25, 26, and 27.

FIGS. 21, 22A-22B, 23A-23B, 24A-24B, 25A-25B, 26A-26B, and 27A-27B show that aqueous samples containing compounds 1 and 10, compounds 1, 2, and 10, and compounds 2, 6, and 10 exhibited a high sweetness response, no bitterness response, and some aftertaste. FIGS. 22A-22B, 23A-23B, 24A-24B, 25A-25B, 26A-26B, and 27A-27B contain graphs showing that the aqueous sample containing compounds 2, 6, and 10 resulted in the highest sweetness response. FIGS. 22B and 27A also indicate that the aqueous sample containing compounds 2 and 6 exhibited a similar receptor response to the aqueous sample containing all 10 compounds from Table 4.

Ten of the eleven aqueous samples were then tested for their ability to activate the sweet taste receptors T1R2/T1R3, GLUT4, and Glucagon in accordance with the procedures described in Example 8. The receptor responses were then compared with the responses of sucrose, sucralose, HFCS, RA50 (50% rebaudioside A, 30% stevioside, 10% rebaudioside C, and 10% trace level glycosides), and rebaudioside A. The results are shown in FIGS. 28A-28B, 29A-29B, 30A-30B, 31A-31B, 32A-32B, 33, and 34.

FIG. 31B contains a graph showing that the aqueous sample containing compounds 2, 6, and 10 exhibited a similar receptor response as sucrose, while FIGS. 32B and 33 show that the aqueous samples containing compounds 1 and 10 and compounds 2 and 6 exhibited a similar receptor response as HFCS. FIG. 34 overlays the receptor responses of the sweet taste receptors T1R2/T1R3, GLUT4, and Glucagon and the bitter taste receptors T2R for sugar, *stevia*, the aqueous sample containing compounds 1 and 10, and the aqueous sample containing compounds 2, 6, and 10. FIG. 34 shows that the taste of *stevia* can be modulated toward a sugar-like taste profile by using specific combinations of compounds identified in Example 7.

TABLE 7

| Sample | Compounds Present | Compound 1 Concentration (ppm) | Compound 2 Concentration (ppm) | Compound 6 Concentration (ppm) | Compound 10 Concentration (ppm) |
|---|---|---|---|---|---|
| XII | 2 | | 6.1 | | |
| XIII | 1, 2 | 0.43 | 6.1 | | |
| XIV | 2, 6 | | 6.1 | 6.74 | |
| XV | 6, 10 | | | 6.74 | 0.29 |
| XVI | 1, 10 | 0.43 | | | 0.29 |
| XVII | 1, 2, 6 | 0.43 | 6.1 | 6.74 | |
| XVIII | 1, 2, 10 | 0.43 | 6.1 | | 0.29 |
| XIX | 2, 6, 10 | | 6.1 | 6.74 | 0.29 |
| XX | 1, 6, 10 | 0.43 | | 6.74 | 0.29 |
| XXI | 1, 2, 6, 10 | 0.43 | 6.1 | 6.74 | 0.29 |

Example 11—Effect of Compound Concentration on Receptor Response

A base solution without *stevia* and an 8 wt % *stevia* blend 3 base solution were prepared in accordance with the procedures described in Example 10. A 0.2 wt % *stevia* blend 3 base solution was then prepared in accordance with the procedures described in Example 10, except that 0.2 wt % of *stevia* blend 3 was used. Eight aqueous samples were prepared by separately adding one or more of the compounds listed in Table 4, or 2-methylbutanol (referred to as "iso2"), to the 8 wt % *stevia* blend 3 base solution and to the 0.2 wt % *stevia* blend 3 base solution. Samples XXII and XXIII contained a mixture of compounds 1, 2, 3, 4, 6, 7, 8, 9, 10, and 12 (referred to as "M10") at the same concentrations as in Example 8. The specific combinations of compounds for Samples XXIV-XXIX are shown in Table 8 with the concentrations of each respective compound.

TABLE 8

| Sample | Compounds and Stevia Blend | Compound Concentration (ppm) | | | | |
|---|---|---|---|---|---|---|
| | | 1 | 2 | 6 | 10 | iso2 |
| XXIV | 2 + 8% Stevia Blend 3 | | 6.1 | | | |
| XXV | 2 + 0.2% Stevia Blend 3 | | 6.1 | | | |
| XXVI | 1, 2, 6, 10 + 8% Stevia Blend 3 | 0.43 | 6.1 | 6.74 | 0.29 | |
| XXVII | 1, 2, 6, 10 + 0.2% Stevia Blend 3 | 0.43 | 6.1 | 6.74 | 0.29 | |
| XXVIII | iso2 + 8% Stevia Blend 3 | | | | | 6.1 |
| XXIX | iso2 + 0.2% Stevia Blend 3 | | | | | 6.1 |

The eight aqueous samples and the three base solutions were tested for their ability to activate the sweet taste receptors T1R2/T1R3, GLUT4, and Glucagon and the bitter taste receptors T2R in accordance with the procedures described in Example 8. The results are shown in FIGS. 35, 36, 37A-37B, 38A-38B, 39A-39B, 40A-40B, 41A-41B, 42A-42B, 43A-43B, and 44A-44B.

FIGS. 35, 40A-40B, 41A-41B, 42A-42B, 43A-43B, and 44A-44B show a comparison between the receptor responses for each combination of compounds combined with either the 8% *stevia* blend 3 base solution or a 0.2% *stevia* blend 3 base solution. In particular, the aqueous sample containing all 10 compounds from Example 7 and the 8% *stevia* blend 3 base solution exhibited high sweet and low bitterness receptor response, while the same combination with 0.2% *stevia* blend 3 base solution exhibited high sweet and aftertaste, but no bitterness. Also, the aqueous sample containing 2-methylbutanol and the 8% *stevia* blend 3 base solution exhibited low sweet and no bitterness receptor response, but the same combination with 0.2% *stevia* blend 3 base solution exhibited high sweet and bitterness receptor response.

FIGS. 36, 37A-37B, 38A-38B, and 39A-39B contain graphs showing the effect on receptor response when compound 2 from Example 7 is exchanged with 2-methylbutanol (or "iso2"). According to FIGS. 36, 37A-37B, 38A-38B, and 39A-39B, the aqueous sample comprising 2-methylbutanol and the 8% *stevia* blend 3 base solution exhibited significantly lower sweet and glucagon receptor response as compared to the sample with compound 2 and the 8% *stevia* blend 3 base solution. Also, the aqueous sample comprising 2-methylbutanol in the presence of compounds 1, 6 and 10 showed significant bitterness blocking.

Example 12—Modulating the Receptor Response of *Stevia*

An 8% *stevia* solution was prepared by dissolving in water 8 wt % of a blend containing 1.3 wt % rebaudioside D, 6.7 wt % SG95 (95% total steviol glycosides comprising 50-65% rebaudioside A, 15-30% stevioside, and 5-35% trace level glycosides) ("*stevia* blend 4"), and 0.32 wt % potassium sorbate. Malic acid was added to the solution until the pH was 3.5. Two aqueous samples were then prepared by combining the 8 wt % *stevia* blend 4 solution with the specific compounds and concentrations listed in Table 9.

TABLE 9

| Sample | Compounds Present | Compound 1 Concentration (ppm) | Compound 2 Concentration (ppm) | Compound 6 Concentration (ppm) | Compound 10 Concentration (ppm) |
|---|---|---|---|---|---|
| XXX | 1, 10 | 0.43 | | | 0.29 |
| XXXI | 2, 6, 10 | | 6.1 | 6.74 | 0.29 |

A 7% sucrose solution, prepared by dissolving 7 wt % sucrose in water, was separated into first and second portions. Potassium sorbate (0.32 wt %) was added to the first portion followed by malic acid until the pH was 3.5. Compounds 2, 6, and 10 were added next in the concentrations listed in Table 4 for the *stevia* concentrate.

The 8% *stevia* blend 4 solution, the second portion of the sucrose solution, the first portion of the sucrose solution containing compounds 2, 6, and 10, and the two aqueous samples (XXX and XXXI) were tested for their ability to activate sweet taste receptors T1R2/T1R3, GLUT4, and Glucagon and bitter taste receptors T2R in accordance with the procedures described in Example 8. The results are shown in FIGS. 45A-45B, 46, and 47, which contain graphs showing that the aqueous sample containing *stevia* with compounds 1 and 10 exhibited increased sweetness and blocked bitterness. This response was similar to the response for the sucrose (sugar) solution. As such, this combination of compounds was considered a bitter blocker and sweet enhancer for *stevia*.

The graphs in FIGS. 45A-45B, 46, and 47 further indicate that the aqueous sample with compounds 2, 6, and 10 with the 8% *stevia* blend 4 exhibited increased sweetness and partial blocking of bitterness. Also, when added to sugar, compounds 2, 6, and 10 exhibited increased sweetness, bitterness, and aftertaste. Thus, this combination of compounds was considered a sweet enhancer for both *stevia* and sugar.

Example 13—Sensory Differences Between a Barrel Aged *Stevia* Solution and a Non-Barrel Aged *Stevia* Solution A sensory test was conducted to show that barrel aged *stevia* blend 4 has an improved taste profile as compared to non-barrel aged *stevia* blend 4. A barrel aged *stevia* blend 4 sample was prepared by dissolving in water 8 wt % of the *stevia* blend 4 (1.3 wt % rebaudioside D and 6.7 wt % SG95) and 0.32 wt % potassium sorbate. Malic acid was added to the solution until the pH was 3.5. An oak barrel was treated in accordance with the procedures described in Example 7. The 8% *stevia* blend 4 solution was added to the treated oak barrel and stored at 21° C. for 6 weeks. After 6 weeks, the *stevia* blend 4 solution was diluted to 400 ppm TSG in 0.1% citric acid. A non-barrel aged *stevia* blend 4 sample was prepared by dissolving in water 8 wt % of the *stevia* blend 4 (1.3 wt % rebaudioside D and 6.7 wt % SG95) and 0.32 wt % potassium sorbate. Malic acid was added to the solution until the pH was 3.5. The solution was diluted to 400 ppm TSG in 0.1% citric acid.

Sensory tests were conducted with the two *stevia* blend 4 samples using targeted descriptive analysis (TDA) with 10 expert tasters and 2 replications. The samples were presented in a sequential monadic manner and the serving order was rotated and balanced across the tasters. Data was analyzed by mixed model ANOVA using XLstat 2014 with Dinnett's HSD post-hoc versus a control at a 90% significant difference confidence level. The results are shown in FIG. 48 and FIG. 49.

As shown in FIGS. 48 and 49, the barrel aged and non-barrel aged *stevia* blend 4 samples exhibited significantly different taste profiles, where the barrel aged *stevia* blend 4 sample was less bitter and less artificial tasting than the non-barrel aged *stevia* blend 4 sample.

Example 14—Sensory Studies Between a Barrel Aged *Stevia* Solution and a *Stevia* Solution Containing Specific Compounds Isolated from an Oak Barrel A sensory test was conducted to show that a barrel aged *stevia* blend 4 solution has a similar taste profile as a *stevia* blend 4 solution containing specific compounds identified in Example 7. An 8% *stevia* blend 4 sample was prepared by dissolving in water 8 wt % of the *stevia* blend 4 (1.3 wt % rebaudioside D and 6.7 wt % SG95) and 0.32 wt % potassium sorbate. Malic acid was added to the solution until the pH was 3.5. The 8% *stevia* blend 4 solution was split into two equal batches. The first batch was added to an oak barrel treated in accordance with the procedures described in Example 7 and stored at 21° C. for 6 weeks. After 6 weeks, the barrel aged *stevia* blend 4 solution was diluted to 400 ppm TSG in 0.1% citric acid. One or more of the compounds listed in Table 4 were added to samples of the second batch of the *stevia* blend 4 solution in the concentrations specified in Table 4 for the *stevia* concentrate. The solution was then diluted to 400 ppm TSG in 0.1% citric acid to provide the nine samples with the composition and concentrations shown in Table 10.

TABLE 10

| Sample No. | Compounds Present | Compound 1 Concentration | Compound 2 Concentration | Compound 6 Concentration | Compound 10 Concentration |
|---|---|---|---|---|---|
| XXXII | 1, 2, 6, 10 | 2.5 ppb | 34.9 ppb | 38.5 ppb | 1.66 ppb |
| XXXIII | 1, 2, 6 | 2.5 ppb | 34.9 ppb | 38.5 ppb | |
| XXXIV | 1, 2, 10 | 2.5 ppb | 34.9 ppb | | 1.66 ppb |
| XXXV | 2, 6, 10 | | 34.9 ppb | 38.5 ppb | 1.66 ppb |
| XXXVI | 1, 6, 10 | 2.5 ppb | | 38.5 ppb | 1.66 ppb |
| XXXVII | 1, 6 | 2.5 ppb | | 38.5 ppb | |
| XXXVIII | 1, 10 | 2.5 ppb | | | 1.66 ppb |
| XXXIX | 2, 6 | | 34.9 ppb | 38.5 ppb | |
| XL | 2, 10 | | 34.9 ppb | | 1.66 ppb |

Ten expert tasters were presented with water to rinse and cleanse their palate prior to tasting each sample. The tasters were presented with a control and one coded sample at room temperature and asked to taste the control, rinse their palate with water, and then taste the coded sample. The tasters were then asked to compare the coded sample to the control and rate the overall liking on a scale from +5 to −5, where a positive score indicated a higher overall liking and a negative score indicated lower overall liking. The tasters considered sweetness, bitterness, and aftertaste when determining overall liking. The tasters were allowed to re-taste multiple times and were required to cleanse their palate with water between each tasting. The same process was repeated with the remaining samples. The results for each sample were averaged together and graphed in FIG. 50.

As shown in FIG. 50, regardless of the specific combination of compounds, the tasters found no significant difference between the barrel aged *stevia* blend 4 and the *stevia* blend 4 containing specific compounds identified in Example 7.

Example 15—The Effect of Compound Concentration on Receptor Response

Several sets of aqueous samples were prepared to study the dose response for the sweet taste receptors. One set of samples was prepared by adding the *stevia* blend 4 (1.3 wt % rebaudioside D and 6.7 wt % SG95) to water and adding 0.32 wt % potassium sorbate. Malic acid was added to the solution until the pH was 3.5. Eleven sets of aqueous samples were prepared by separately combining the same *stevia* 4 blend with either 2-methylbutanol or one of the compounds listed in Table 4. Another set of samples was prepared by adding sugar to water. Four additional sets of aqueous samples were prepared by separately combining each of the *stevia* blend 4, above, and sugar with either compounds 1 and 10 or compounds 2, 6, and 10 from Table 4. One final set of aqueous samples was prepared by combining the *stevia* blend 4, above, with compounds 1, 2, 3, and 10 from Table 4. Each set of samples were serially diluted and had concentrations ranging from about 0.001 nM to about 100 μM.

The aqueous samples were tested at varying concentrations for their ability to activate the sweet taste receptors in accordance with the procedures described in Example 8. Dose response curves were generated for the *stevia* 4 blend, sugar, and each compound-*stevia* 4 blend combination. The dose response curves are shown in FIGS. 51-68.

An ideal taste modulator, or sweet enhancer, exhibits good receptor activation, which is indicated by a large taste enhancement, shown by a large Max-Min value, at a relatively low concentration, shown by a low $EC_{50}$ value. As shown in FIG. 57, compound 2 is a sweet enhancer for the *stevia* 4 blend, because it has a low $EC_{50}$ value. FIGS. 53 and 59 show that while the combination of compounds 1 and 10 and compounds 2, 6, and 10 enhanced sweetness for sugar with a low $EC_{50}$ value, the Max-Min values, or enhancement, were small, indicating the limitation of those compounds to modulate sugar's taste profile. However, the same compounds exhibited a high Max-Min value when combined with the *stevia* blend 4 indicating larger sweet enhancement in that sweetener system despite the higher $EC_{50}$ values.

FIGS. 51-68 also show that the compounds identified in Example 7 can exhibit a synergistic effect when added to the *stevia* 4 blend in certain combinations. For example, the dose response curve for compounds 1 and 10 with the *stevia* 4 blend from FIG. 52 is different than expected based on the individual dose response curves for compound 1 with the *stevia* 4 blend and compound 10 with the *stevia* 4 blend shown in FIGS. 51 and 55, respectively. In particular, the curves for the individual compounds with the *stevia* 4 blend exhibit smaller slopes and $EC_{50}$ values than the curve for the combination of the two compounds.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A sweetener composition, comprising:
   (1) a non-nutritive sweetener;
   (2) trans-4-methyl-5-butyldihydro-2(3H)-furanone; and
   (3) two or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

2. The sweetener composition of claim 1, which is substantially free of any compounds having a molecular weight of greater than 500 daltons, greater than 1000 daltons or greater than 2000 daltons.

3. A sweetener composition, comprising:
   (1) a non-nutritive sweetener; and
   (2) a flavor-modifying composition comprising trans-4-methyl-5-butyldihydro-2(3H)-furanone and two or more compounds selected from the group consisting of furfural, 4-hexen-1-ol, trans-2,4-hexadienal, 2,4-hexadien-1-ol, 5-methyl-furfural, delta-tetradecalactone, cis-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

4. The sweetener composition of claim 3, wherein the flavor-modifying composition is substantially free of any compounds having a molecular weight of greater than 500 daltons, greater than 1000 daltons or greater than 2000 daltons.

5. The sweetener composition of claim 1, wherein
   a) the compound furfural is present in an amount from about 6 ppb to about 10 ppm, from about 13 ppb to about 5 ppm, or from about 80 ppb to about 5 ppm;
   b) the compound 4-hexen-1-ol is present in an amount from about 0.6 ppb to about 1 ppm, from about 1.3 ppb to about 0.5 ppm, or from about 8 ppb to about 0.5 ppm;
   c) the compound trans-2,4-hexadienal is present in an amount from about 2.5 ppb to about 4 ppm, from about 5 ppb to about 2 ppm, or from about 30 ppb to about 2 ppm;
   d) the compound 2,4-hexadien-1-ol is present in an amount from about 0.4 ppb to about 4 ppm, from about 2 ppb to about 3 ppm, from about 4 ppb to about 1.5 ppm, or from about 24 ppb to about 1.5 ppm;
   e) the compound 5-methyl-furfural is present in an amount from about 0.3 ppb to about 1 ppm, from about 0.5 ppb to about 0.5 ppm, from about 0.7 ppb to about 0.25 ppm, or from about 4 ppb to about 0.25 ppm;
   f) the compound delta-tetradecalactone is present in an amount from about 0.1 ppb to about 0.04 ppm, from about 0.1 ppb to about 0.02 ppm, or from about 0.3 ppb to about 0.02 ppm;
   g) the compound cis-4-methyl-5-butyldihydro-2(3H)-furanone is present in an amount from about 0.1 ppb to about 0.5 ppm, from about 0.2 ppb to about 0.3 ppm, from about 0.3 ppb to about 0.1 ppm, or from about 1.6 ppb to about 0.1 ppm;
   h) the compound 3-methylbutanol is present in an amount from about 0.8 ppb to about 10 ppm, from about 1 ppb to about 5 ppm, from about 1.2 ppb to about 1.2 ppm, from about 1.6 ppb to about 0.6 ppm, or from about 9.5 ppb to about 0.6 ppm;

i) the compound ethyl octanoate is present in an amount from about 0.1 ppb to about 0.4 ppm, from about 0.5 ppb to about 0.2 ppm, or from about 3.2 ppb to about 0.2 ppm;

j) the compound ethyl decanoate is present in an amount from about 0.1 ppb to about 2.4 ppm, from about 0.3 ppb to about 1.2 ppm, or from about 1.6 ppb to about 1.2 ppm; and k) the compound ethyl hexadecanoate is present in an amount from about 0.6 ppb to about 1 ppm, from about 1.3 ppb to about 0.5 ppm, or from about 7.9 ppb to about 0.5 ppm.

6. The sweetener composition of claim 1, wherein the non-nutritive sweetener comprises a steviol glycoside, Lo Han Guo sweetener, rubusoside, siamenoside, monatin, curculin, glycyrrhizic acid, neohesperidin, dihydrochalcone, glycyrrhizin, glycyphyllin, phloridzin, trilobatin, phyllodulcin, brazzein, hernandulcin, osladin, polypodoside A, baiyunoside, pterocaryoside A and B, mukurozioside, thaumatin, monellin, mabinlins I and II, phlomisoside I, periandrin I, abrusoside A, and cyclocarioside I, mogroside IV, mogroside V, or derivatives or salts thereof, or combinations thereof.

7. The sweetener composition of claim 6, wherein the non-nutritive sweetener comprises a steviol glycoside selected from the group consisting of stevioside, rebaudioside A, rebaudioside B, rebaudioside C, rebaudioside D, rebaudioside E, rebaudioside F, rebaudioside G rebaudioside H rebaudioside I, rebaudioside J, rebaudioside K, rebaudioside L, rebaudioside M, rebaudioside N, rebaudioside O, rebaudioside P, rebaudioside Q, steviolbioside, dulcoside A, or derivatives, or combinations thereof.

8. The sweetener composition of claim 1, wherein the non-nutritive sweetener comprises an aqueous steviol glycoside composition comprising rebaudioside D and a stevioside composition.

9. The sweetener composition of claim 8, wherein the rebaudioside D is present from about 0.5 wt % to about 1.5 wt %, from about 1 wt % to about 1.5 wt %, from about 1.3 wt % to about 1.4 wt %, or is present at about 1.3 wt %, about 1.4 wt % or about 1.5 wt % of the aqueous steviol glycoside composition.

10. The sweetener composition of claim 8, wherein the stevioside composition and the rebaudioside D are present in a ratio of from about 1:1 to about 10:1, from about 2:1 to about 7:1, or about 2:1, about 3:1, about 5:1 or about 6:1.

11. The sweetener composition of claim 8, wherein the stevioside composition comprises stevioside and a second steviol glycoside selected from the group consisting of rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside O, steviolbioside, rubusoside, and dulcoside A.

12. A ready-to-drink beverage comprising:
a) water;
b) a sweetener composition of claim 1;
c) optionally an acidulant selected from the group consisting of phosphoric acid, citric acid, malic acid, tartaric acid, lactic acid, formic acid, ascorbic acid, fumaric acid, gluconic acid, succinic acid, maleic acid, adipic acid, and mixtures thereof; and
d) optionally a flavorant.

13. The ready-to-drink beverage of claim 12, wherein the flavorant comprises a cola flavorant, a tea flavorant, a caramel flavorant, and a coffee flavorant.

14. The ready-to-drink beverage of claim 12, further comprising caffeine.

15. The ready-to-drink beverage of claim 12, wherein the beverage has fewer than about 200 calories per 8 oz serving.

16. The ready-to-drink beverage of claim 12, wherein the beverage further comprises a nutritive sweetener.

17. A beverage concentrate comprising water and the sweetener composition of claim 1.

18. A method of making the sweetener composition of claim 1, comprising:
adding to the non-nutritive sweetener trans-4-methyl-5-butyldihydro-2(3H)-furanone and two or more compounds selected from the group consisting of furfural, 4-hexen-1-ol, trans-2,4-hexadienal, 2,4-hexadien-1-ol, 5-methyl-furfural, delta-tetrade calactone, cis-4-methyl-5-butyldihydro-2(3H)-furanone, butyl acetate, 3-methylbutanol, 2-methylbutanol, ethyl octanoate, ethyl decanoate, ethyl hexadecanoate, and combinations thereof.

19. A method of making a sweetener composition, comprising:
adding to an aqueous solution comprising a non-nutritive sweetener a flavor-modifying composition comprising trans-4-methyl-5-butyldihydro-2(3H)-furanone and two or more compounds selected from the group consisting of furfural, 4-hexen-1-ol, trans-2,4-hexadienal, 2,4-hexadien-1-ol, 5-methyl-furfural, delta-tetradecalactone, cis-4-m ethyl-5-butyldihydro-2(3H)-furanone, butyl acetate, 3-methylbutanol, 2-methylbutanol, ethyl octanoate, ethyl decanoate, ethyl hexadecanoate, and combinations thereof.

20. The method of claim 19, wherein said adding comprises contacting the aqueous solution of the non-nutritive sweetener in an oak barrel or with oak chips.

21. The method of claim 20, wherein said contacting occurs at from about 10 ° C. to about 50 ° C., or from 21 ° C. to 40 ° C., for at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, or at least about 6 weeks.

22. The method of claim 20, further comprising filtering the aqueous solution of the non-nutritive sweetener after the adding.

23. The method of claim 19, wherein the aqueous solution comprises from about 1 wt % to about 25 wt %, from about 5 wt % to about 15 wt %, from about 6 wt % to about 13 wt %, or about 7 wt %, about 8 wt %, about 9 wt %, about 10 wt %, about 11 wt % or about 12 wt % of the non-nutritive sweetener.

24. The method of claim 18, wherein the non-nutritive sweetener comprises a steviol glycoside, Lo Han Guo sweetener, rubusoside, siamenoside, monatin, curculin, glycyrrhizic acid, neohesperidin, dihydrochalcone, glycyrrhizin, glycyphyllin, phloridzin, trilobatin, phyllodulcin, brazzein, hernandulcin, osladin, polypodoside A, baiyunoside, pterocaryoside A and B, mukurozioside, thaumatin, monellin, mabinlins I and II, phlomisoside I, periandrin I, abrusoside A, and cyclocarioside I, mogroside IV, mogroside V, or derivatives or salts thereof, or combinations thereof.

25. The method of claim 24, wherein the non-nutritive sweetener comprises a steviol glycoside selected from the group consisting of stevioside, rebaudioside A, rebaudioside B, rebaudioside C, rebaudioside D, rebaudioside E, rebaudioside F, rebaudioside G rebaudioside H rebaudioside I, rebaudioside J, rebaudioside K, rebaudioside L, rebaudioside M, rebaudioside N, rebaudioside O, rebaudioside P, rebaudioside Q, steviolbioside, dulcoside A, or derivatives, or combinations thereof.

26. The method of claim 18, wherein the non-nutritive sweetener comprises an aqueous steviol glycoside composition comprising rebaudioside D and a stevioside composition.

27. The method of claim 26, wherein the rebaudioside D is present from about 0.5 wt % to about 1.5 wt %, from about 1 wt % to about 1.5 wt %, from about 1.3 wt % to about 1.4 wt %, or is present at about 1.3 wt %, about 1.4 wt % or about 1.5 wt % of the aqueous steviol glycoside composition.

28. The method of claim 26, wherein the stevioside composition and the rebaudioside D are present in a ratio of from about 1:1 to about 10:1, from about 2:1 to about 7:1, or about 2:1, about 3:1, about 5:1 or about 6:1.

29. The method of claim 26, wherein the stevioside composition comprises stevioside and a second steviol glycoside selected from the group consisting of rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside O, steviolbioside, rubusoside, and dulcoside A.

30. The sweetener composition of claim 1, wherein the sweetener composition further comprises a nutritive sweetener.

* * * * *